US010219492B2

(12) United States Patent
Bao et al.

(10) Patent No.: US 10,219,492 B2
(45) Date of Patent: Mar. 5, 2019

(54) COMPOUNDS AND METHODS FOR ALTERING RSV REPLICATION RATE

(71) Applicants: Xiaoyong Bao, Galveston, TX (US); Yong Sun Lee, League City, TX (US)

(72) Inventors: Xiaoyong Bao, Galveston, TX (US); Yong Sun Lee, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/550,399

(22) Filed: Nov. 21, 2014

(65) Prior Publication Data
US 2015/0152420 A1    Jun. 4, 2015

Related U.S. Application Data

(60) Provisional application No. 61/907,734, filed on Nov. 22, 2013.

(51) Int. Cl.
| | |
|---|---|
| *A61K 31/70* | (2006.01) |
| *C12N 15/63* | (2006.01) |
| *A01K 67/027* | (2006.01) |
| *A61K 31/713* | (2006.01) |
| *A61K 45/06* | (2006.01) |
| *C12N 15/113* | (2010.01) |
| *A01K 67/00* | (2006.01) |

(52) U.S. Cl.
CPC ........ *A01K 67/0271* (2013.01); *A61K 31/713* (2013.01); *A61K 45/06* (2013.01); *C12N 15/113* (2013.01); *C12N 2310/11* (2013.01); *C12N 2310/315* (2013.01); *C12N 2310/321* (2013.01); *C12N 2760/18511* (2013.01)

(58) Field of Classification Search
CPC .. A01K 67/0271; A61K 31/713; A61K 45/06; C12N 15/113
See application file for complete search history.

(56) References Cited

U.S. PATENT DOCUMENTS

| | | | | |
|---|---|---|---|---|
| 8,258,288 | B2 * | 9/2012 | McSwiggen ..... | A61K 47/48023 536/24.5 |
| 8,586,726 | B2 * | 11/2013 | Califano ............... | C12N 15/113 536/23.1 |
| 2009/0093026 | A1 | 4/2009 | Dowdy et al. | |
| 2013/0197067 | A1 * | 8/2013 | Anderson ............... | C12N 15/11 514/44 R |
| 2013/0211380 | A1 * | 8/2013 | Cabrera Aquino ... | A61M 5/178 604/508 |

OTHER PUBLICATIONS

Agnello et al., "Hepatitis C virus and other Flaviviridae virsues enter cells via low density lipoprotein receptor," *Proc. Natl. Acad. Sci. U.S.A.*, 1999; 96(22):12766-12771.
Akaike et al., "Nitric oxide and virus infection," *Immunology*, 2000; 101:300-308.
Altschul et al., "Basic local alignment search tool," *J. Mol. Biol.*, 1990; 215(3):403-410.
Altshul et al., "Gapped BLAST and PSI-BLAST: a new generation of protein database search programs," *Nucleic Acids Res.*, 1997; 25(17):3389-3402.
Ardelt et al., "Amino Acid Sequence of an Anti-tumor Protein from *Rana pipiens* Oocytes and Early Embryos," *J. Biol. Chem.*, 1991; 266(1):245-251.
Asirvatham et al., "miRNA regulation of cytokine genes." *Cytokine*, 2009; 45(2):58-69.
Bannister et al., "Use of a highly sensitive strand-specific quantitative PCR to identify abortive replication in the mouse model of respiratory syncytial virus disease," *Virology Journal*, 2010; 7;250; 11 pgs.
Bao et al., "Airway epithelial cell response to human metapneumovirus infection," *Virology*, 2007; 368:91-101.
Bao et al., "Human Metapneumovirus Glycoprotein G Inhibits Innate Immune Responses," *PLoS Pathogens*, May 2008; 4(5):e1000077; 12 pgs.
Bawage et al., "Recent Advances in Diagnosis, Prevention, and Treatment of Human Respiratory Syncytial Virus," *Advances in Virology*, 2013; 2013: 1-26.
Bern et al., "Animal models of human respiratory syncytial virus disease," *Am. J. Physiol. Lung Cell Mol. Physiol.*, 2011; 301:L148-L156.
Bitko et al., "An Endoplasmic Reticulum-Specific Stress-Activated Caspase (Caspase-12) is Implicated in the Apoptosis of A549 Epithelial Cells by Respifatory Syncytial Virus," *J. Cell. Biol.*, 2001; 80:441-451.
Bitko et al., "Inhibition of respiratory viruses by nasally administered siRNA," *Nature Medicine*, 2005; 11(1):50-55.
Boss et al., "Viral miRNAs; tool for immune evasion," *Curr. Opin. Microbiol.*, 2010; 13(4):540-545.
Cabili et al., "Integrative annotation of human large intergenic noncoding RNAs reveals global properties and specific subclasses," *Genes & Development*, 2011, 25:1915-1927.
Castelli et al., "The 2-5A system in viral infection and apoptosis," *Biomed Pharmacother*, 1998; 52(9):386-390.
Cole et al., "Filtering of deep sequencing data reveals the existence of abundant Dicer-dependent small RNAs derived from tRNAs," *RNA*, 2009; 15:2147-2160.
Collins et al., "Viral and Host Factors in Roman Respiratory Syncytial Virus Pathogenosis," *J. Virol.*, Mar. 2008; 82(5)2040-2055.
Deng et al., "Respiratory Syncytial Virus Utilizes a tRNA Fragment to Suppress Antiviral Responses Through a Novel Targeting Mechanism," *Molecular Therapy*, 2015, 23(10):1622-1629.

(Continued)

*Primary Examiner* — Quang Nguyen
(74) *Attorney, Agent, or Firm* — Nueting, Raasch and Gebhardt, P.A.

(57) ABSTRACT

Provided herein are methods for altering respiratory syncytial virus (RSV) replication in a cell using oligonucleotides derived from tRNAs, also referred to as tRFs (tRNA-derived RNA Fragments). The oligonucleotides may be used to decrease or increase replication of RSV. Also provided herein are methods for treating a subject having or at risk of having an RSV infection, and animal models for evaluating viral and host factors in RSV pathogenesis.

22 Claims, 32 Drawing Sheets

Specification includes a Sequence Listing.

(56) References Cited

OTHER PUBLICATIONS

DeVincenzo et al., "A randomized, double-blind, placebo-controlled study of an RNAi-based therapy directed against respiratory syncytial virus," *PNAS USA*, 2010; 107:8800-8805.

Dölken et al., "Cytomegalovirus microRNAs," *Virus Genes*, 2009; 38:355-364.

Eguchi et al., "Efficient siRNA delivery into primary cells by a peptide transduction domain-dsRNA binding domain fusion protein," *Nature Biotechnology*, 2009; 27:567-571.

Eiland, L., "Respiratory Syncytial Virus: Diagnosis, Treatment and Prevention," *J. Pediatr. Pharmacol. Ther.*, 2009, 14(2):75-85.

Emara et al., "Angiogenin-induced tRNA-derived Stress-induced RNAs Promote Stress-induced Stress Granule Assembly," *J. Biol. Chem.*, 2010; 285:10959-10968.

Esteller, "Non-coding RNAs in human disease," *Nature Reviews Genetics*, 2011; 12:861-874.

Falsey et al., "Respiratory Syncytial Virus Infection in Elderly and High-Risk Adults," *New England Journal of Medicine*, 2005; 352:1749-1759.

Franzen et al., "The Short Non-Coding Transcirptome of the Protozoan Parasite *Trypanosoma cruzi*," *PLoS. Negl. Trop. Dis.*, 2011; 5(8):e1283.

Fujishima et al., "Sequence Evidence in the Archaeal Genomes that tRNAs Emerged Through the Combination of Ancestral Genes as 5' and 3' tRNA Halves," *PLoS One*, 2008; 3:e1622.

Gait et al., "Peptide-mediated cellular delivery of antisense oligonucleotides and their analogues," *Cell. Mol. Life Sci.*, 2003; 61:1-10.

Garofalo et al., "Upregulation of class 1 major histocompatibility complex (MHC) molecules on respiratory syncytial virus (RSV)-infected airway epithelial cells," *Am. J. Respir. Crit Care Med*, 1994; 149:A987.

Gebetsberger et al., "Slicing tRNAs to boost functional ncRNA diversity," *RNA Biology*, 2014, 10(12):1798-1806.

Gerlier et al., "Interplay between Innate Immunity and Negative-Strand RNA Viruses: towards a Rational Model," *Microbiol. Mol. Biol. Rev.*, 2011; 75:468-490.

Glezen et al., "Risk of Primary Infection and Reinfection with Respiratory Syncytial Virus," *Am J Dis Child*, 1986; 140(6):543-546.

Gomez et al., "NeST, a long noncoding RNA, controls microbial susceptibility and epigenetic activation of the Ifng locus," *Cell*, 2013, 152(4):743-754.

Gong et al., "Compartmentalized, function role of angiogenin during spotted fever group rickettsia-induced endothelial barrier dysfunction: evidence of possible medication by host tRNA-derived small noncoding RNAs," *BMC Infectious Diseases*, 2013, 13:285-300.

Guerrero-Plata et al., "Human Metapneumovirus Induces a Profile of Lung Cytokines Distinct from That of Respiratory Syncytial Virus," *J. Virol.*, Dec. 2005; 79(23):14992-14997.

Haasnoot et al., "RNAi and cellular miRNAs in infections by mammalian viruses," *Methods Mol. Biol.*, 2011; 721:23-41.

Haeberle et al., "Inducible Expression of Inflammatory Chemokines in Respiratory Syncytial Virus-Infected Mice: Role of MIP-lα in Lung Pathology," *Journal of Virology*, 2001; 75(2):878-890.

Haiser et al., "Developmentally regulated cleavage of tRNAs in the bacterium *Streptomyces coelicolor*," *Nucleic Acids Research*, 2008; 36(3):732-741.

Haussecker et al., "Human tRNA-derived small RNAs in the global regulation of RNA silencing," *RNA*, 2010; 16:673-695.

Hermos et al., "Human Metapneumovirus," *Clin Lab Med*, 2010; 30:131-148.

Hess et al., "Small RNA profiling of Dengue virus-mosquito interactions implicates the PIWI RNA pathway in anti-viral defense," *BMC Microbiology*, 2011; 11:45; 12 pgs.

Hsieh et al., "Uncovering Small RNA-Mediated Responses to Phosphate Deficiency in Arabidopsis by Deep Sequencing[1][W][OA]," *Plant Physiol.*, 2009; 151:2120-2132.

Hsieh et al., "Abundance of tRNA-derived small RNAs in phosphate-starved Arabidopsis roots," *Plant Signal Behav.*, 2010; 5(5):537-539.

Ideue et al., "Efficient oligonucleotide-mediated degradation of nuclear noncoding RNAs in mammalian cultured cells," *RNA*, 2009; 15:1578-1587.

Josset et al., "Annotation of long non-coding RNAs expressed in Collaborative Cross founder mice in response to respiratory virus infection reveals a new class of interferon-stimulated transcripts," *RNA Biol.*, 2014; 11(7):875-890.

Kaufmann, "Anticodon nucleases," *Trends Biochem. Sci.*, 2000; 25(2):70-74.

Kolb et al., "Gene Therapy for Pulmonary Diseases" *Chest*, 2006; 130:879-884.

Krüger et al., "RNAhybrid: microRNA target prediction easy, fast and flexible," *Nucleic Acids Res.*, 2006; 34 (Web Server Issue):W451-W454.

Lee et al., "Distinct Roles for *Drosophila* Dicer-1 and Dicer-2 in the siRNA/miRNA Silencing Pathways," *Cell*, 2004; 117:69-81.

Lee et al., "Starvation-induced Cleavage of the tRNA Anticodon Loop in *Tetrahymena thermophile*," *J. Biol. Chem.*, 2005; 280(52):42744-42749.

Lee et al., "A novel class of small RNAs: tRNA-derived RNA fragments (tRFs)," *Genes Dev.*, 2009, 23;2639-2649.

Lee et al., "Precursor miR-886, a novel noncoding RNA repressed in cancer, associates with PKR and modulates its activity," *RNA*, 2009; 17;1076-1089.

Li et al., "The Sequence Alignment/Map format and SAMtools," *Bioinformatics*, 2009: 25(16):2078-2079.

Lindsay et al., "Peptide-mediated cell delivery: application in protein target validafion," *Curr. Opin. Pharmacol.*, 2002; 2:581-591.

Liu et al., "Systematic identification of microRNA and messenger RNA profiles in hepatitis C virus-infected human hepatoma cells," *Virology*, 2010; 398:57-67.

Loss-Morais et al., "Description of plant tRNA-derived RNA fragments (tRFs) associated with argonaute and identification of their putative targets," *Biol. Direct.*, 2013; 8:6-10.

Martin et al., "Births: Final Data for 2005," *National Viral Statistics Reports*, 2007; 56(6):1-104.

Papenburg et al., "The distinguishing features a human metapneumovirus and respiratory syncytial virus," *Rev Med Virol*, 2010; 20:245-260.

Peng et al., "A novel class of tRNA-derived small RNAs extremely enriched in mature mouse sperm," *Cell Res.*, 2012; 22(11):1609-1612.

Peng et al., "Unique signature of long noncoding RNA expression in response to virus infection and altered innate immune signaling," *mBio.*, 2010; 1(5):e001206-e001210.

Pfeffer et al., "Identification of Virus-Encoded MicroRNAs," *Science*, 2004; 304(5671):734-736.

Phan et al., "Identification of functional tRNA-derived RNA fragments (tRFs) in Respiratory Syncytial Virus infection," American Society for Microbiology Texas Branch 2014 Fall Meeting, Nov. 6-8, Houston, Texas.

Reese et al., "Identification of Novel MicroRNA-Like Molecules Generated from Herpesvirus and Host rRNA Transcripts," *J. Virol.*, 2010; 84(19):10344-10353.

Rehmsmeier et al., "Fast and effective prediction of microRNA/target duplexes," *RNA*, 2004; 10(10):1507-1517.

Ren et al., "Human metapneumovirus M2-2 protein inhibits innate cellular signaling by targeting MAVS," *J. Virol.*, 2012; 86(23):13049-13061.

Ren et al., "A novel mechanism for the inhibition of interferon regulatory factor-3-dependent gene expression by human respiratory syncytial virus NS1 protein," *J. Gen. Virol.*, 2011; 92:2153-2159.

Ren et al., "Human Metapneumovirus Inhibits IFN-β Signaling by Downregulating Jak1 and Tyk2 Cellular Levels," *PLosONE*, 2011; 6:e24496.

Ren et al., "Human Metapneumovirus M2-2 Protein Inhibits Innate Immune Response in Monocyte-Derived Dendritic Cells," *PLoS One*; 2014; 9(3):091865.

(56) References Cited

OTHER PUBLICATIONS

Ruggero et al., "Small noncoding RNAs in cells transformed by human T-cell leukemia virus type 1: a role for a tRNA fragment as a primer for reverse transcriptase," *J. Virol.*, 2014; 88(7):3612-3622.
Sambrook et al., (Eds.), *Molecular Cloning: A Laboratory Manual*, Cold Spring Harbor Laboratory Press: Cold Spring Harbor, NY; 1989. Title page, publisher's page, and table of contents, 30 pgs.
Skalsky et al., "Viruses, microRNAs, and Host Interactions," *Ann. Rev. Microbiol.*, 2010; 64:123-141.
Sobala et al., "Transfer RNA-derived fragments: origins, processing, and fuctions," *Wiley Interdisciplinary Reviews: RNA*, 2011; 2(6):853-862.
Suhasini et al., "Transfer RNA Cleavages by Onconase Reveal Unusual Cleavage Sites," *J. Biol. Chem.*, 2006; 281:12201-12209.
Thompson et al., "tRNA cleavage is a conserved response to oxidative stress in eukaryotes," *RNA*, 2008; 14:2095-2103.
Thompson et al., "The Rnase Rny 1p cleaves tRNA and promotes cell death during oxidative stress in *Saccharomyces cerevisiae*," *J. Cell Biol.*, 2009; 185:43-50.
Tuck et al., "RNA in pieces," *Trends in Genetics*, 2011; 27(10):422-432.
Turner et al., "Respiratory syncytial virus: current and emerging treatment options," *ClinicoEconomics and Outcomes Research*, 2014, 6:217-225.
Wadia et al., "Protein transduction technology," *Curr. Opin. Biotechnol.*, 2002; 13(1):52-56.
Wang, Q.; Lee, I.; Ren, J.; Ajay, S. S.; Lee, Y. S.; Bao, X. Identification Functional Characterization of tRNA-derived RNA Fragments (tRFs) in Respiratory Syncytial Virus Infection. *Mol. Ther.* 2012.
Wang et al., "Identification and Functional Characterization of tRNA-derived RNA Fragments (tRFs) in Respiratory Syncytial Virus Infection," *Molecular Therapy*, 2013, 21(2):368-379.
Yamasaki et al., "Angiogenin cleaves Trna and promotes stress-induced translational repression," *J. Cell Biol.*, 2009; 185:35-42.
Yoo et al., "2'-O-methyl-modified phosphorothioate antisense oligonucleotides have reduced non-specific effects in vitro," *Nucleic Acids Research*, 2004; 32(6):2008-2016.
Zhang et al., "Expression of Respiratory Syncytial Virus-Induced Chemokine Gene Networks in Lower Airway Epithelial Cells Revealed by cDNA Microarrays," *J. Virol.*, 2001; 75(19):9044-9058.
Zhang et al., "Inhibition of respiratory syncytial virus infection with intranasal siRNA nanoparticles targeting the viral NS1 gene," *Nature Medicine*, 2005; 11(1):56-62.
Zhang et al., "The Phloem-Delivered RNA Pool Contains Small Noncoding RNAs and Interferes with Translation," *Plant Physiol.*, 2009; 150:378-387.
Robertson et al., "Specificity and functionality of microRNA inhibitors," *Silence*, 2010; 1(1):10.

\* cited by examiner

Figure 25

COMPOUNDS AND METHODS FOR ALTERING RSV REPLICATION RATE

CROSS-REFERENCE TO RELATED APPLICATIONS

This application claims the benefit of U.S. Provisional Application Ser. No. 61/907,734, filed Nov. 22, 2013, which is incorporated by reference herein.

GOVERNMENT FUNDING

The present invention was made with government support under R21 AI113771, KAI074829A and 1 R56 AI107033-01A1, awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "US14550399_SequenceListing_ST25.txt" having a size of 25 kilobytes and created on Feb. 11, 2015. The information contained in the Sequence Listing is incorporated by reference herein.

BACKGROUND

During the last decade, significant attention has been directed towards identification of small non-coding RNAs (sncRNAs) and their biological functions (for review, see Esteller, (2011) Nat Rev Genet 12:861-874), references cited herein are detailed at the end of the Examples]. sncRNAs are 16-35 nucleotides (nts) long and of several classes including microRNA (miRNA), small interfering RNA (siRNA), piwi-interacting RNA (piRNA), etc. Among them, miRNA and siRNA are the most extensively studied, and both suppress gene expression by complementary binding to target mRNAs. The role of sncRNAs in regulating antiviral innate immune responses has just emerged and is largely unexplored (Skalsky et al., (2010) Annu Rev Microbiol 64:123-141).

Discovery of new types of sncRNAs has been greatly facilitated by the development of ultra-throughput sequencing (also called next generation sequencing or deep sequencing) technologies. Numerous sncRNAs have been captured and mapped to various origins, such as mRNA (messenger), rRNA (ribosomal), tRNA (transfer), and sncRNA (small nucleolar RNA), indicating that they are derived from these long RNAs. However, their biological significance remains largely unknown. Although a substantial fraction of sncRNAs might be simply degradation intermediates or by-products during RNA turnover, recent studies have demonstrated that some sncRNAs are actually functional molecules with specific biogenesis (reviewed in Tuck et al., (2011) Trends Genet 27:422-432).

sncRNAs derived from tRNAs, also called tRNA-derived RNA Fragments (tRFs), have been recently identified by several research groups (reviewed in Sobala et al., (2011) Wiley, Interdiscip Rev RNA 2:853-862). There is increasing evidence that they are not by-products from random degradation, but functional molecules. First, tRFs are produced through specific cleavage of tRNA by endonucleases such as angiogenin (ANG), Dicer, and ELAC2 (Emara et al., (2010) J Biol Chem 285:10959-10968, Yamasaki et al., (2009) J Cell Biol 185:35-42, Cole et al., (2009) RNA 15:2147-2160, Lee et al., (2009) Genes Dev 23:2639-2649). Second, tRF expression is regulated either by cellular stresses (Emara et al., (2010) J Biol Chem 285:10959-10968, Yamasaki et al., (2009) J Cell Biol 185:35-42) or cell proliferation (Lee et al., (2009) Genes Dev 23:2639-2649). Third, some tRFs are functional, having trans-silencing activity or being necessary for cell proliferation (Lee et al., (2009) Genes Dev 23:2639-2649, Haussecker et al., (2010) RNA 16:673-695).

Respiratory tract infections (RTIs) are the second leading cause of death worldwide in children less than 5 years old. The majority of RTIs are caused by viruses, among which a paramyxovirus called respiratory syncytial virus (RSV) figures prominently (reviewed in Hermos et al., (2010) Clin Lab Med 30:131-148, Papenburg et al., (2010) Rev Med Virol 20:245-260). Nearly all children have had RSV infection by 2-3 years of age (Glezen et al., (1986) Am J Dis Child 140:543-546). RSV infection also increases the morbidity and mortality rate in immunocompromised patients and the elderly, resulting in a substantial health burden (Falsey et al., (2005) N Eng J Med 352:1749-1759). There is currently no specific treatment or vaccine for RSV infection. Although a prevention strategy has been developed using a humanized monoclonal antibody directed to an epitope of the F protein of RSV, less than 3% of the at-risk infant population has access to this kind of prevention (Martin et al., (2007) Natl Vital Stat Rep 56:1-103).

The role of sncRNAs, especially miRNAs, in host-virus interaction has been documented (Liu et al., (2010) Virology 398:57-67, Hess et al., (2011) BMC Microbiol 11:45). Upon viral infection, host cells alter their sncRNA expression profile as a defense mechanism. On the other hand, viruses can circumvent host defense and promote their propagation by altering cellular sncRNA expression or by expressing their own sncRNAs (Boss et al., (2010) Curr Opin Microbiol 13:540-545, Dolken et al., (2009) Virus Genes 38:355-364, Pfeffer et al., (2004) Science 304:734-736, Reese et al., (2010) J Virol 84:10344-10353). Nonetheless, most of these studies have focused on the role of miRNAs in viral infection, while other types of sncRNAs remain largely unexplored.

SUMMARY OF THE APPLICATION

As described herein, we have analyzed the global expression profile of sncRNAs in RSV-infected airway epithelial cells by Illumina ultra-high-throughput sequencing in order to identify functionally important sncRNAs. RSV led to tRNA cleavage, resulting in an abundant induction of tRFs. By further investigating the biogenesis and function of RSV-induced tRFs, tRFs were found to be important molecules controlling RSV replication. This is the first report on the role of tRFs in viral replication. This study also provides therapeutic targets to control RSV replication, by regulating tRF induction.

Provided herein are methods for altering RSV replication in a cell. In one embodiment, the method includes decreasing RSV replication in a cell. In one embodiment, such a method includes introducing a polynucleotide into a cell to result in decreased RSV replication within the cell compared to replication of RSV within a control cell that does not include the polynucleotide.

In one embodiment, the polynucleotide includes a nucleotide sequence that is substantially identical to the complement of a reference sequence, or identical to the complement of the reference sequence. The reference sequence is at least 20 consecutive nucleotides selected from first 31 nucleotides at the 5' end of a mature tRNA, wherein the mature tRNA is selected from a tRNA that specifies glutamine and has the anticodon CTG or TTG, glutamic acid and has the anticodon CTC or TTC, glycine and has the anticodon TCC or CCC or GCC, histidine and has the anticodon GTG, leucine and has the anticodon TAA, lysine and has the anticodon CTT or TTT, methionine and has the anticodon CAT, phenylalanine and has the anticodon GAA, serine and has the anticodon GCT, or valine and has the anticodon AAC or CAC. In one embodiment, at least 2 polynucleotides are introduced into the cell. The polynucleotide may be RNA, DNA, or both RNA and DNA. In one embodiment, the introducing includes introducing a vector into the cell, wherein the vector encodes the polynucleotide.

In one embodiment, the cell includes RSV when the polynucleotide is introduced into the cell. In another embodiment, the method further includes introducing into the cell an RSV. Introducing the RSV into the cell may occur before, at the same time as, or after introducing the polynucleotide into the cell. The cell may be an ex vivo cell, such as a primary cell or a cultured cell. The cell may be an in vivo cell, such as a cell is present in an animal selected from a human, a chimpanzee, a cow, a sheep, a cotton rat, and a mouse. In one embodiment, the in vivo cell is present in a human that is between 0 and 24 months of age.

Also provided herein are methods for treating a subject. In one embodiment, the method includes administering to a subject in need thereof an effective amount of a composition that includes a polynucleotide. In one embodiment, the subject has or is at risk of having an RSV infection. In one embodiment, the administering includes administering the composition to the respiratory tract of the subject. In one embodiment, the subject is an animal selected from a human, a chimpanzee, a cow, a sheep, a cotton rat, and a mouse. In one embodiment, the subject is a human between 0 and 24 months of age. In one embodiment, the human has symptoms of bronchiolitis, pneumonia, or the combination thereof The polynucleotide may include a nucleotide sequence that is substantially identical to the complement of a reference sequence, or identical to the complement of the reference sequence. The reference sequence is at least 20 consecutive nucleotides selected from first 31 nucleotides at the 5' end of a mature tRNA, wherein the mature tRNA is selected from a tRNA that specifies glutamine and has the anticodon CTG or TTG, glutamic acid and has the anticodon CTC or TTC, glycine and has the anticodon TCC or CCC or GCC, histidine and has the anticodon GTG, leucine and has the anticodon TAA, lysine and has the anticodon CTT or TTT, methionine and has the anticodon CAT, phenylalanine and has the anticodon GAA, serine and has the anticodon GCT, or valine and has the anticodon AAC or CAC.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The presence of APOER2 mRNAs in the tRF5-GluCTC complex was confirmed by RT-PCR.

Figure 17:
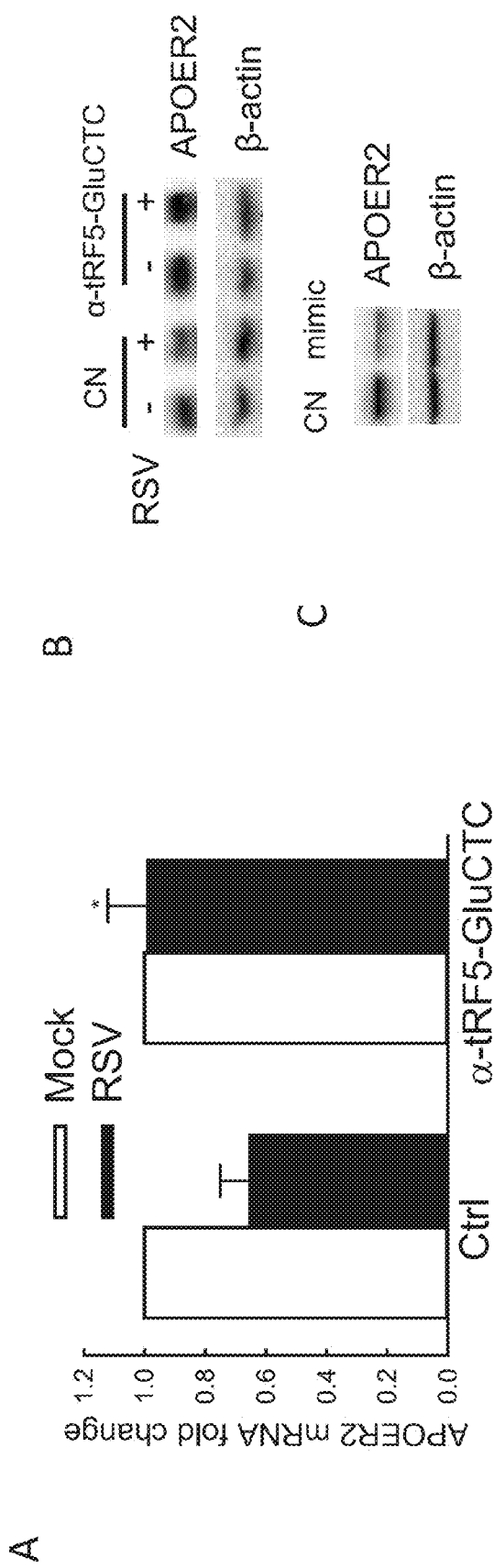

FIG. 17. The regulatory effect of tRF5-GluCTC on the expression of APOER2. A549 cells in 6-well plate were co-transfected with 120 nmol/l antisense oligos, anti-tRF5-GluCTC or anti-control (CN). After 2 hours post-transfection, cells were mock- or RSV-infected, then harvested at 15 hours post-infection to harvest total RNAs or cellular proteins to measure the APOER2's mRNA by qRT-PCR (A) and protein by Western Blot (B) respectively. (C). A549 cells were transfected with 25 nM tRF5-GluCTC oligo or CN oligo. At 15 h post transfection. Total cell lysate was harvested, followed by Western Blot to measure the expression of APOER2.

Figure 18:
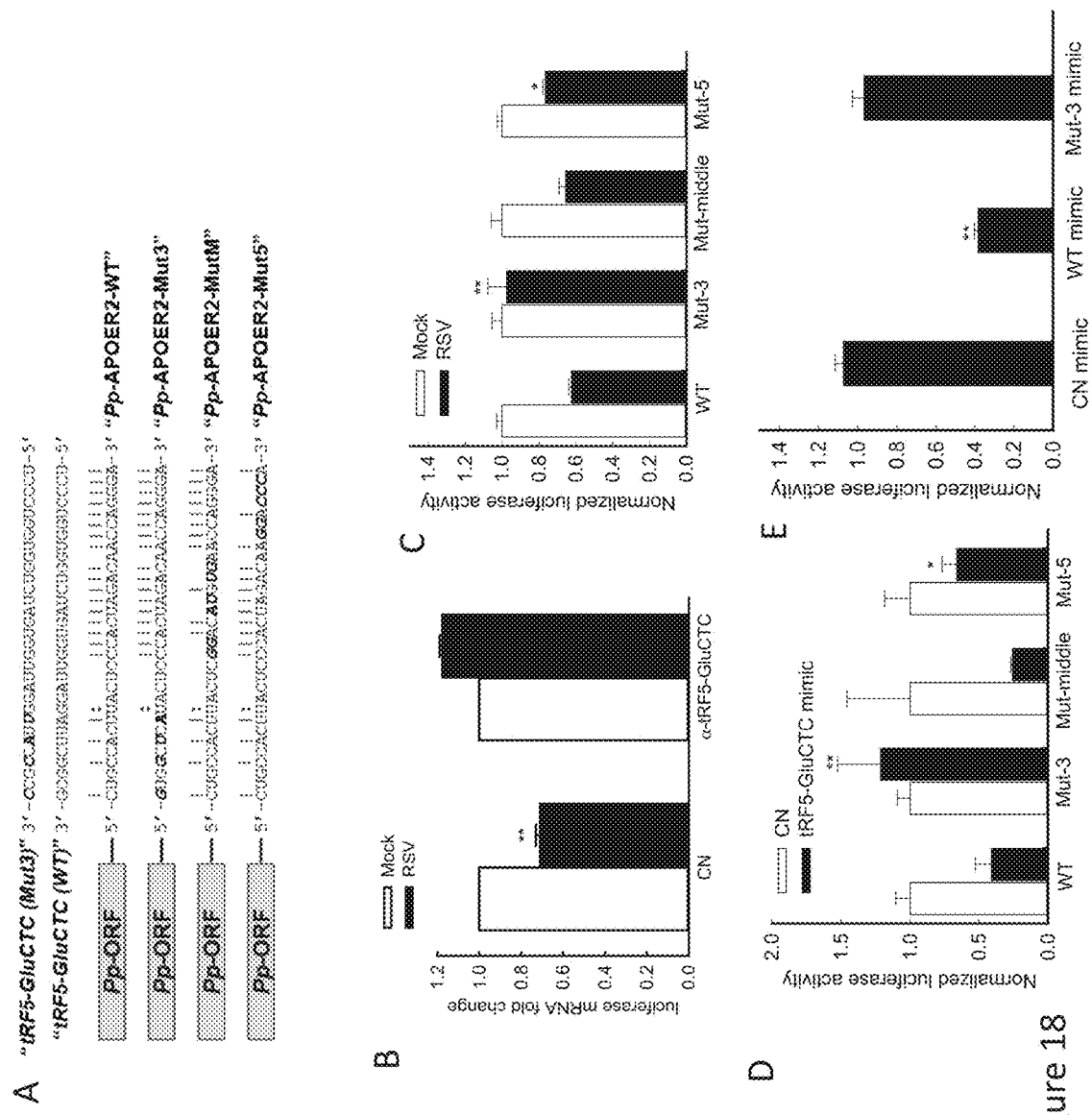

FIG. 18. Sequence elements necessary for target to interact with tRF5-GluCTC. (A) Illustration on the firefly luciferase Pp plasmid construction containing the complementary targeting sequence, WT or mutants, of APEOER2, to identify the motif(s) critical for tRF5-GluCTC targeting. Sequence alignment of Pp-APOER2-WT (SEQ ID NO:122) with three mutant luciferase sensor plasmids (SEQ ID NOs:123, 124, and 125). tRF5-GluCTC, SEQ ID NO:121; tRF5-GluCTC, SEQ ID NO:6; tRF5-GluCTC-mimic (WT), SEQ ID NO:121; tRF5-GluCTC-mimic (Mut3), SEQ ID NO:126. (B). A549 cells were co-transfected with a firefly (Pp) luciferase reporter plasmid carrying complementary sequence of an APOER2 region, which is predicted to be targeted by tRF5-GluCTC, and a plasmid expressing renilla Rr luciferase, and 120 nmol/l antisense oligos, anti-tRF5-GluCTC or CN. After 2 hours post-transfection, cells were mock- or RSV-infected. At 15 h post infection, cells were lysed to measure the luciferase activity. Pp values were first normalized by Rr values yielding relative Pp/Rr values (y-axis). * denotes P value<0.05 respective, relative to first white bar. (C) A549 cells in hexaplicate were transfected with luciferase plasmids, Pp-APOER2-WT, Mut-3, Middle, or Mut-5 (0.1 μg/well), and a Rr luciferase plasmid, were infected with RSV (B) or co-transfected with the tRF5-GluCTC mimic oligonuleotide (D). Mock infection or the control mimic was used as a control for B and C respectively. At 15 h post infection or 30 h post-transfection, cells were lysed for luciferase assays. Values at y-axis (Pp/Rr) are a representative of three independent experiments and are expressed as mean±SE. * or  on the bars denotes P value<0.05 or <0.01 respectively, relative to the black bar (WT Pp and RSV infected samples). (E). A549 cells in hexaplicate were co-transfected with Pp-APOER2-WT plasmid (0.1 μg/well of 24-well plate), a Rr plasmid, and  nmol/l mimic oligos (WT or Mut-3, please see illustration in A). After 15 hours post-transfection, cells were harvested to measure luciferase activities. Values at y-axis (Pp/Rr) are a representative of three independent experiments and are expressed as mean±SE. **On the second bar (tRF5-GluCTC WT mimic transfected) denotes P value<0.01, relative to the first bar (CN mimic transfected).

Figure 19:
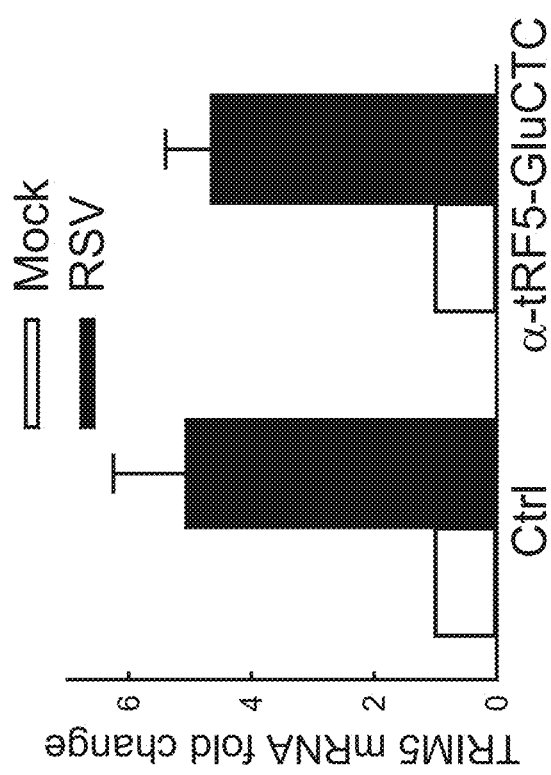

FIG. 19. tRF5-GluCTC does not regulate the expression of TRIM5. A549 cells in 6-well plate were co-transfected with 120 nmol/l antisense oligos, anti-tRF5-GluCTC or anti-control (CN). After 2 hours post-transfection, cells were mock- or RSV-infected, then harvested at 15 hours post-infection to harvest total RNAs to measure the mRNA level of TRIM5 by qRT-PCR. The data were from 3 independent experiments.

Figure 20:
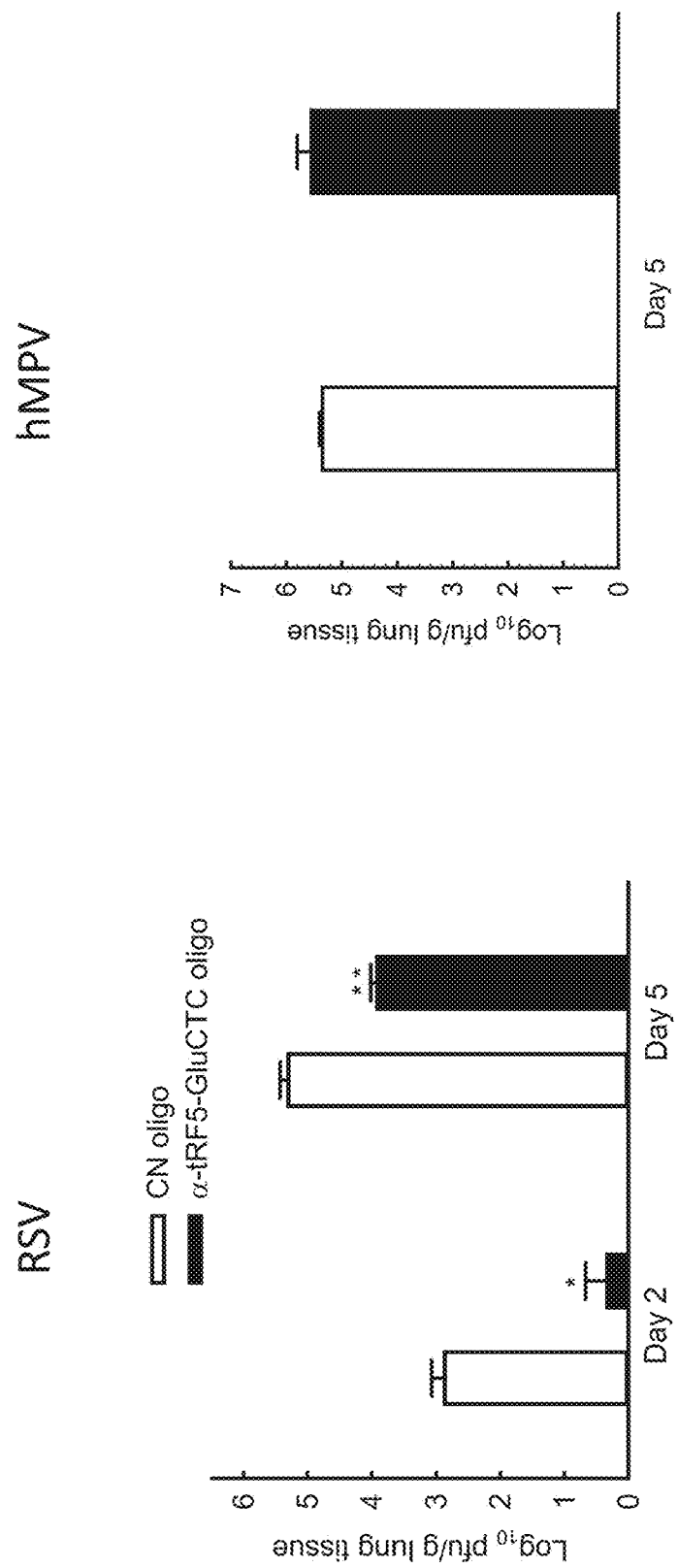

FIG. 20. tRF5-GluCTC promotes RSV replication in vivo. Anti-tRF5-GluCTC (anti-GluCTC) or CN oligo (5 nmol/mice) was mixed with 5 μl TransIT-TKO transfection reagent (Minis, Madison, Wis.) in 50 μl Opti-MEM (Invitrogen), followed by intranasal inoculation into BALB/c mice (n=3/group). After 4 h, mice were mock-infected or infected with RSV (A) or hMPV (B) at $10^7$ pfu/mouse. RSV replication in the lungs was determined on day 2 and/or day 5 p.i. * denotes p<0.05, relative to anti-CN-treated mice. Lung RNAs were also extracted, followed by Northern blotting (NB) to confirm the decrease in tRF5-GluCTC with its antisense oligo.

Figure 21:
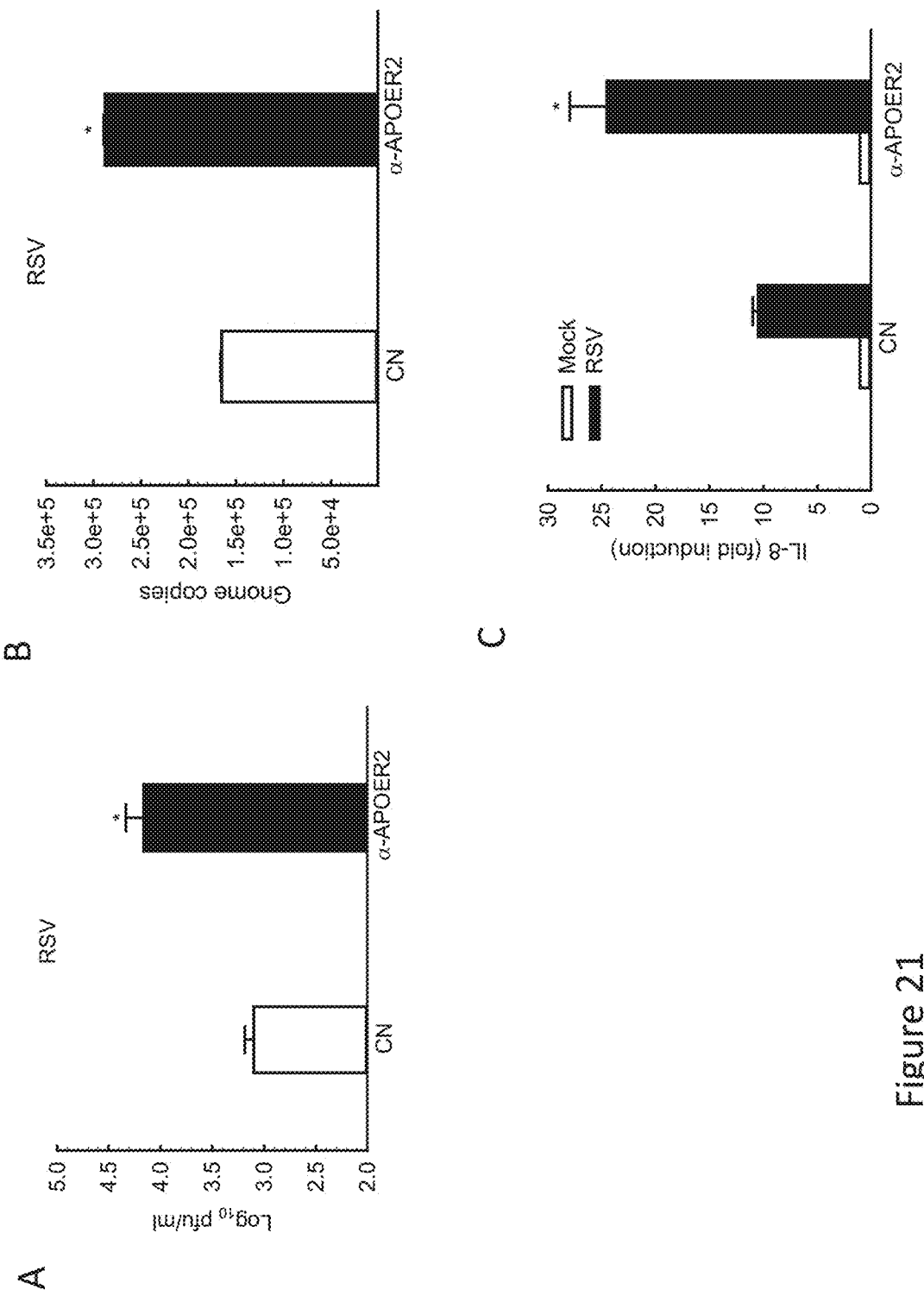

FIG. 21. The effect of APOER2 silencing on RSV replication. A549 cells were transfected with 100 nM APOER2 siRNA (α-APOER2) or control siRNA (CN) using lipofectamine 2000. At 48 h post transfection, cells were mock-infected or infected with RSV at MOI of 1 for 15 h. (A) Total infectious particles were measured by immunostaining and the values expressed as pfu/ml. (B) Genome copies were measured by qRT-PCR. (C) Induced IL-8 was tested by ELISA. * and ** denotes p<0.05 and <0.01 respectively, relative to its CN.

Figure 22:
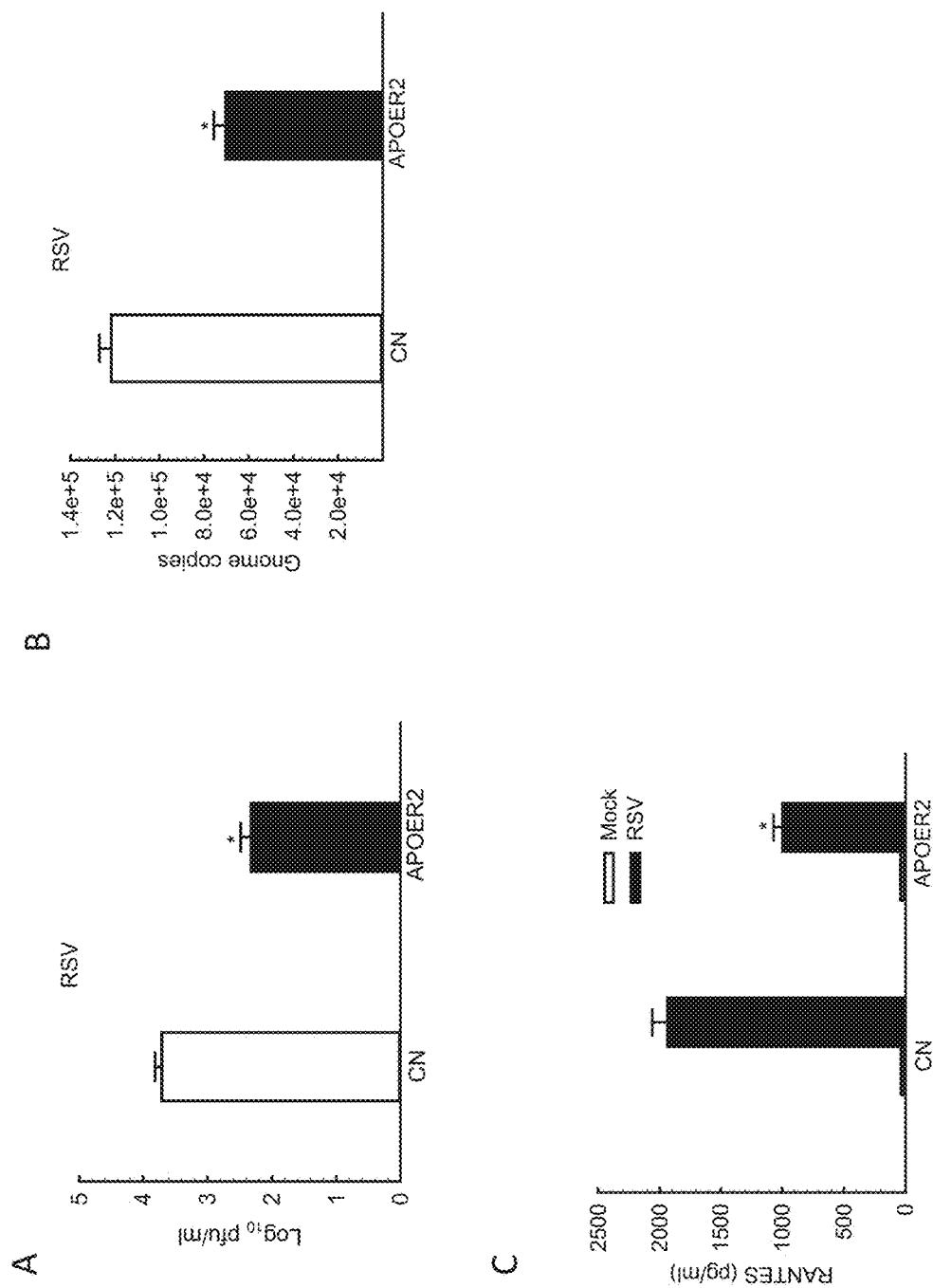

FIG. 22. The effect of APOER2 overexpression on RSV replication. A549 cells were transfected with a plasmid encoding Flag-tagged APOER2 or a control plasmid for 30 h, followed by mock infection or RSV infection (MOI of 1) for 15 h. Total infectious particles (A), genome copies of RSV (B) and the induction of RANTES (C) were measured similarly to FIG. 4. * and ** denotes p<0.05 and <0.01 respectively, relative to its CN.

Figure 23:
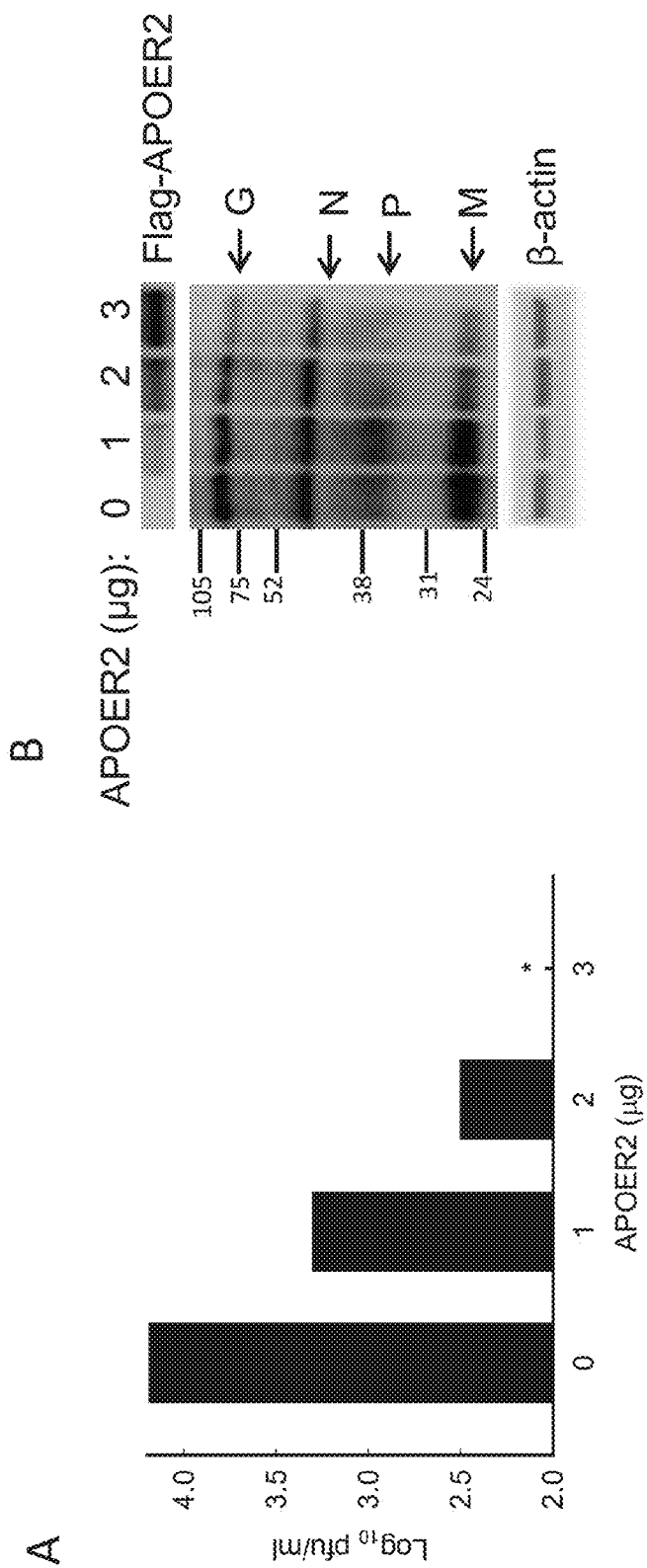

FIG. 23. The inhibitory effect of APOER2 on RSV replication is dose dependent. A549 cells were transfected with a plasmid expressing flag-tagged APOER2 with increasing dose as indicated. At 30 h post transfection, the cells were mock infected or infected with RSV at MOI of 1. At 15 h p.i., the viral particles (A) or total cellular protein (B) were harvested, and measured by immune staining and Western blot using anti-RSV Ab respectively.

Figure 24:
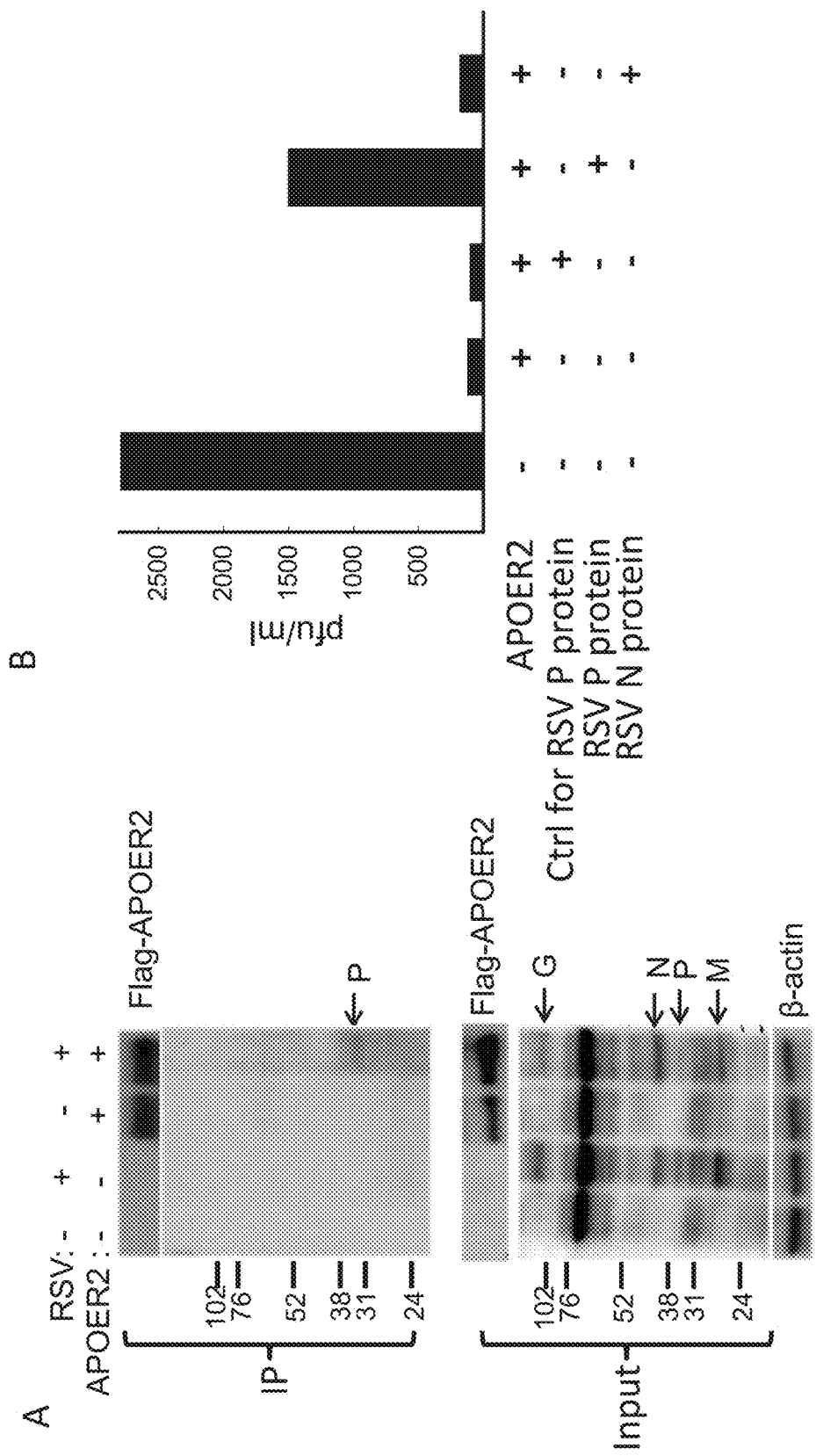

FIG. 24. APOER2 interacts with RSV P protein. (A) APOER2 forms a complex with RSV P protein. A549 cells were transfected with plasmids encoding Flag-tagged APOER2 or it control vectors. At 30 h post transfection, cells were mock infected or infected with RSV at MOI of 1. At 6 h p.i., total cell lysates were immunoprecipitated with an anti-flag antibody followed by Western blotting using an anti-RSV antibody to detect associated RSV protein(s). A small aliquot was also prepared before the IP for a Western blot for equal input for IP. (B) Overexpressed RSV P protein prevents APOER2-inhibited RSV replication. A549 or 293 cells at 50% confluence were transfected with a plasmid encoding VS-tagged RSV P or N (negative control) or their common control vector. After 30 h, cells were mock infected or infected with RSV at MOI of 1 for 15 h. The viral particles in the supernatant were titrated by immune staining (B) and viral protein expression was measured by WB using an anti-RSV Ab. A small aliquot was also prepared to ensure the proper overexpression of RSV P and N.

Figure 25:
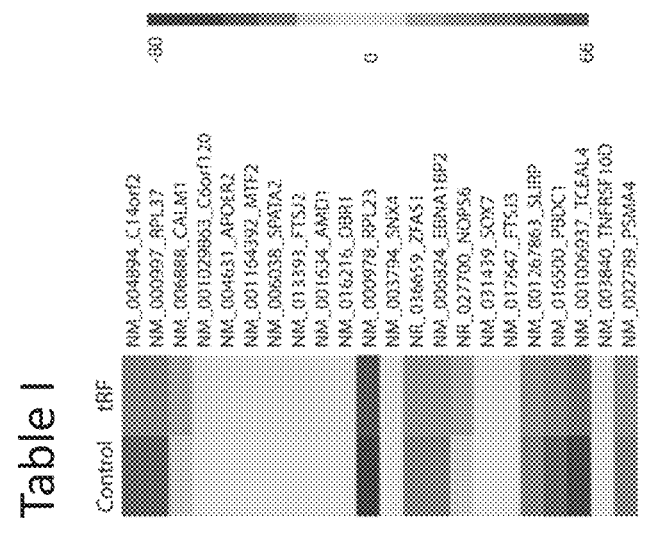

FIG. 25. mRNAs with decreased expression>9 by RSV infection (RSV vs mock infection) from previous microarray data and enhanced binding to tRF5-GluCTC in a log FC>1 (tRF5-GluCTC vs control oligo) (P<0.05).

Figure 26:
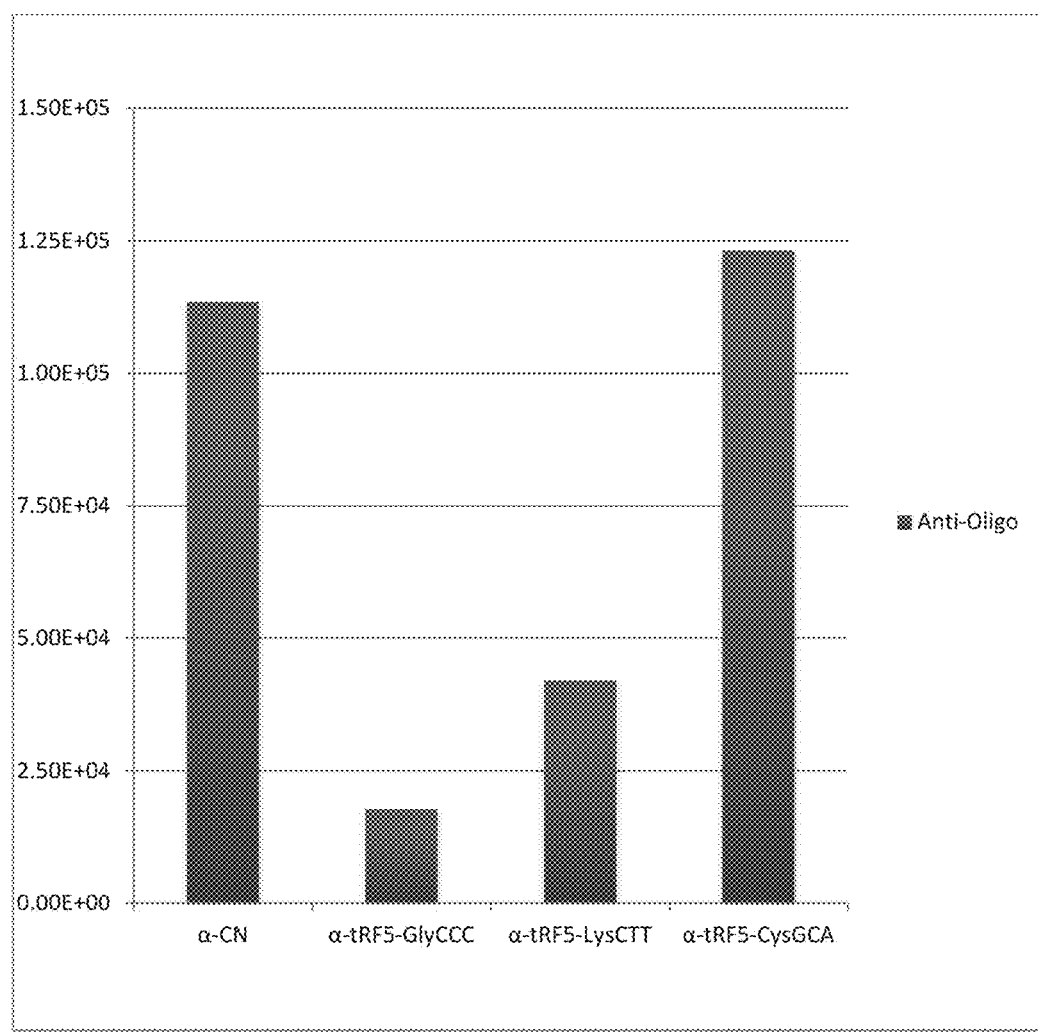

FIG. 26. Anti-Sense oligos and Their Effect on Viral Replication (Total Sonication). α-CN, scrambled control oligo; α-tRF5-GlyCCC, α-tRF5-LysCTT, and α-tRF5-CysGCA, the oligos introduced into the cells.

Figure 27:
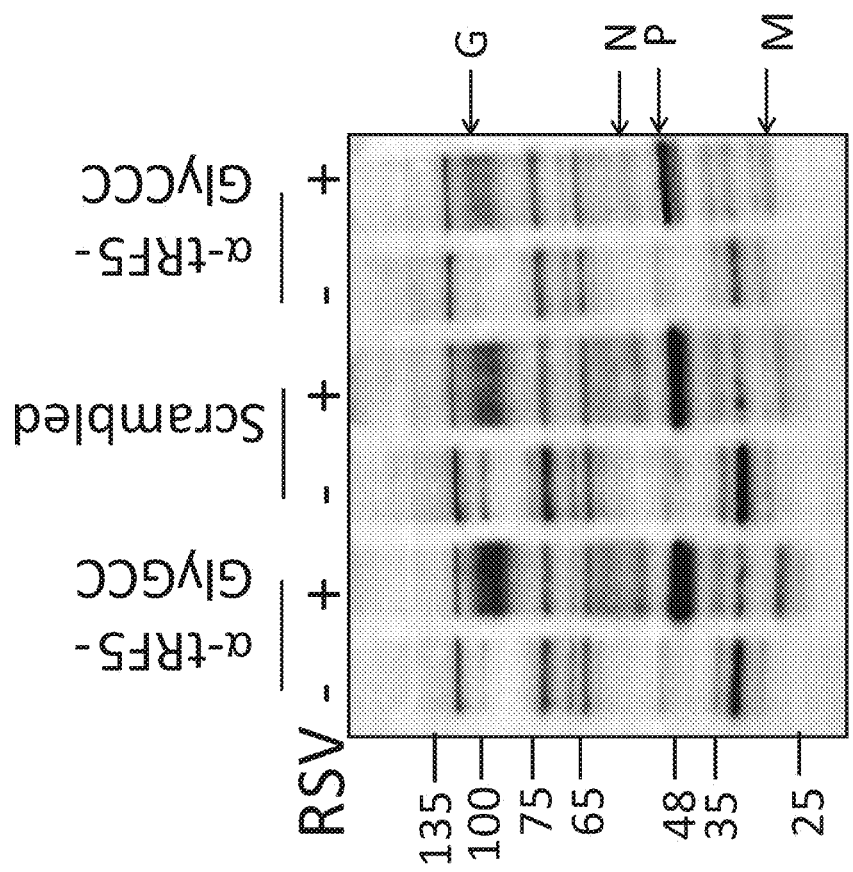

FIG. 27. tRF5-GlyCCC specifically inhibits Viral Protein Production. Bands representing RSV-specific proteins G (viral attachment glycoprotein), N (nucleoprotein), P (polymerase phosphoprotein), and M (matrix protein) are labeled. MOI=3. tRF5-GlyCCC, (SEQ ID NO:12); tRF5-GlyGCC, (SEQ ID NO:11).

Figure 28:
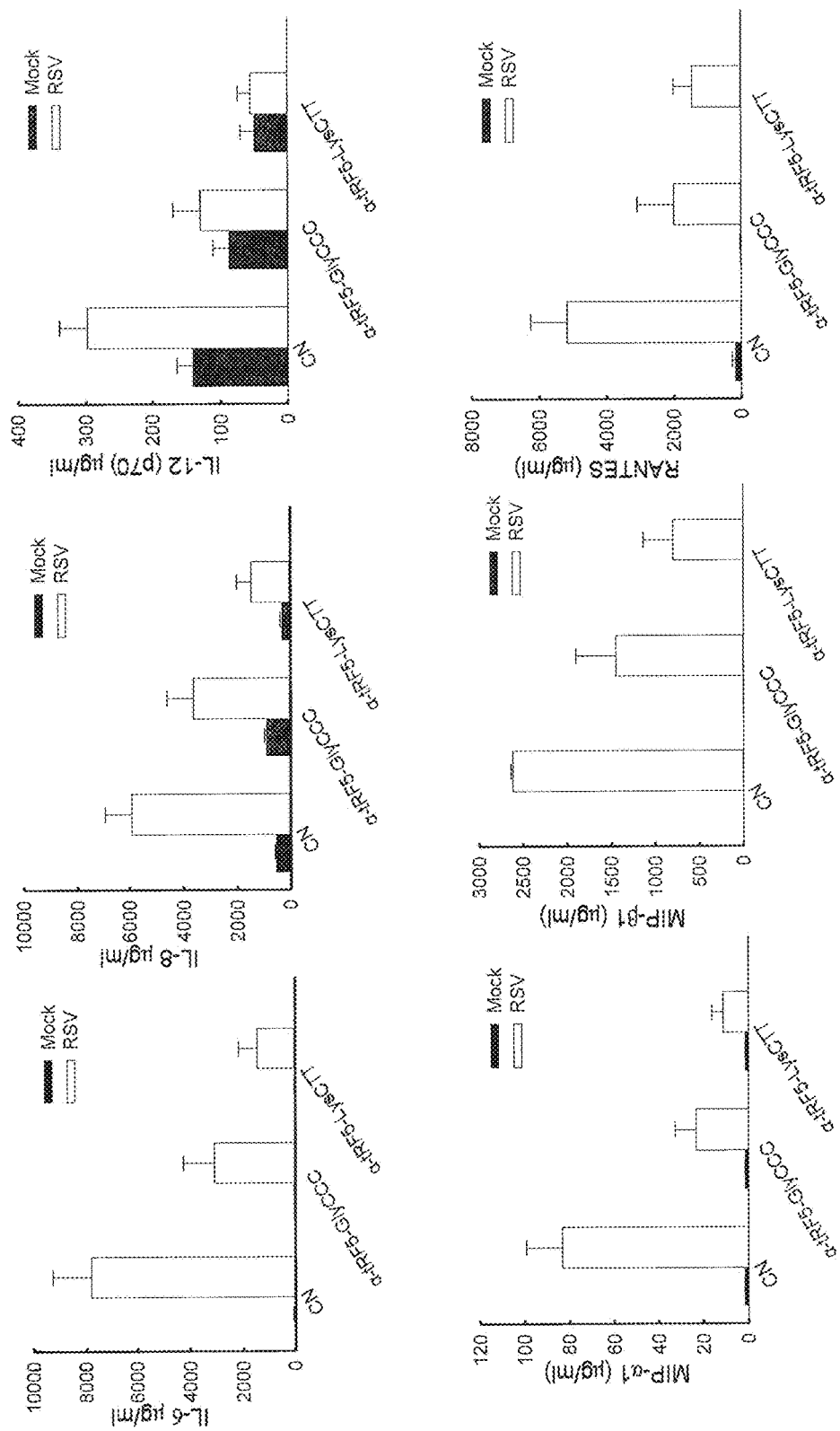

FIG. 28. The effects of tRF5-GlyCCC and LysCTT on the induction of cytokines and chemokines.

Figure 29:
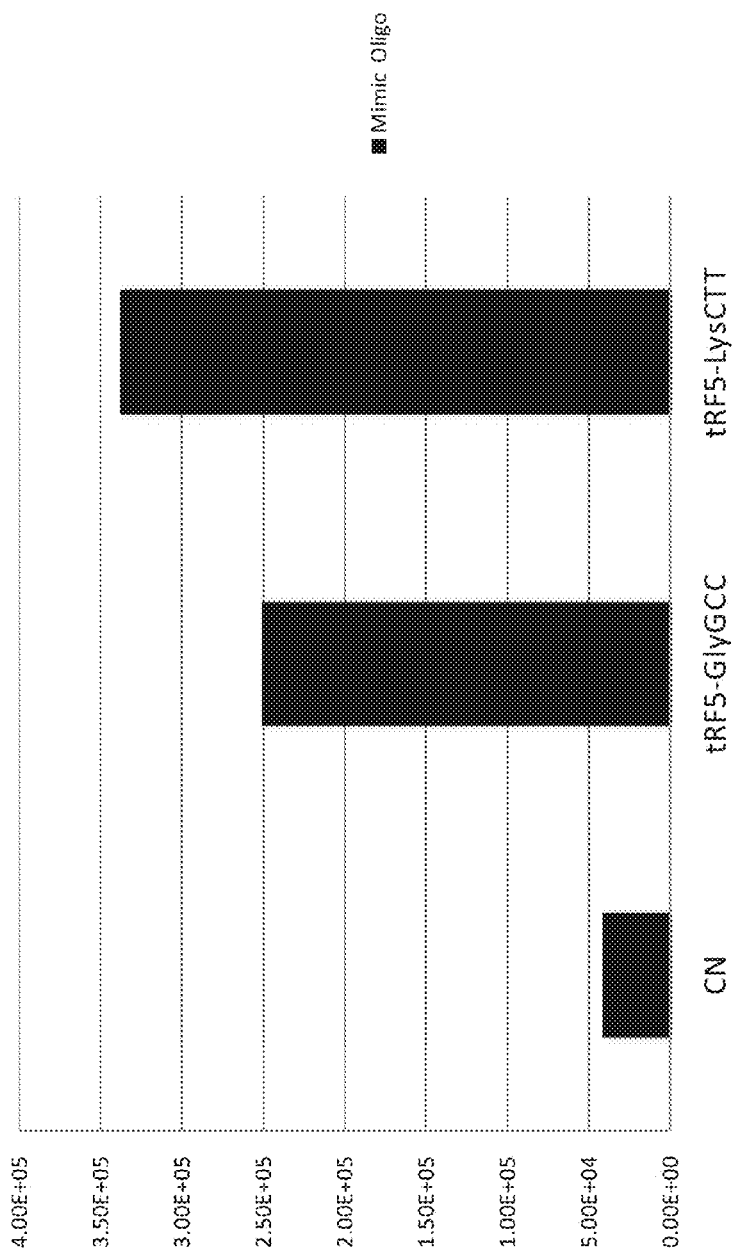

FIG. 29. tRF5-GlyCCC and tRF5-LysCTT mimic promote on the induction of cytokines and Chemokines.

Figure 30:
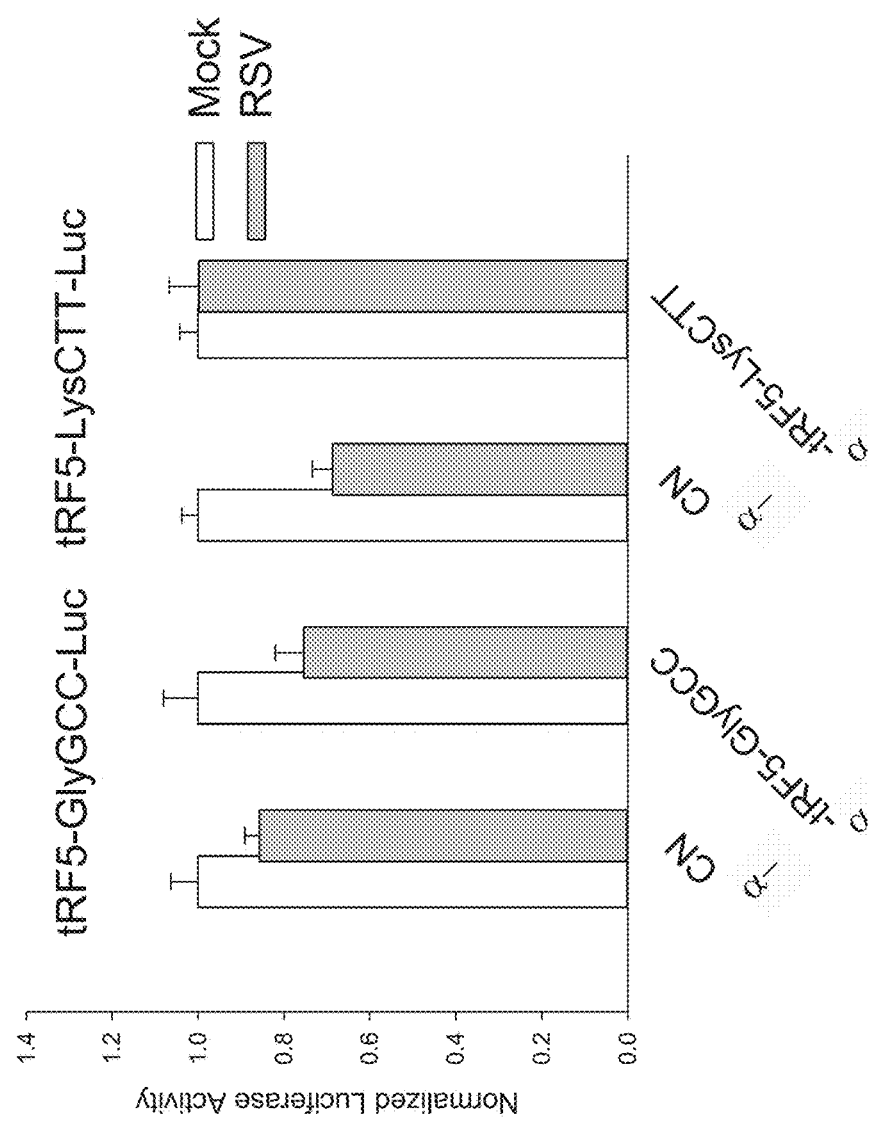

FIG. 30. tRF5-LysCTT has a gene trans-silencing function.

DETAILED DESCRIPTION OF ILLUSTRATIVE EMBODIMENTS

Polynucleotides

The invention described herein is based on observations that certain tRNA-derived RNA fragments (tRFs) are increased in a cell infected with a Respiratory Syncytial Virus (RSV). It was observed that one of the tRFs represses target mRNA in the cytoplasm and promotes RSV replication. It was also observed that an RNA that is an antisense to a portion of a tRF supresses the effect of the tRF, e.g., the antisense oligonucleotide reversed the suppression effect of the tRF on its target mRNA and inhibited RSV replication. As used herein, the term "Respiratory Syncytial Virus" and "RSV" refer to human respiratory syncytial virus, which causes respiratory tract infections in humans mainly during infancy and childhood as well as the elderly.

Provided herein are polynucleotides and methods for using the polynucleotides. As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. A polynucleotide described herein may be isolated. An "isolated" polynucleotide is one that has been removed from its natural environment. Polynucleotides that are produced by recombinant, enzymatic, or chemical techniques are considered to be isolated and purified by definition, since they were never present in a natural environment. It should be understood that sequences disclosed herein as DNA can be converted from a DNA sequence to an RNA sequence by replacing each thymidine nucleotide with a uridine nucleotide. Likewise, RNA sequences disclosed herein can be converted from an RNA sequence to a DNA sequence by replacing each uridine nucleotide with a thymidine nucleotide In one embodiment, a polynucleotide provided herein includes a sequence that is identical to a reference sequence selected from any one of SEQ ID NO:1-27, or a portion of a reference sequence. As used herein, the term "identical" means the nucleotide sequence of the polynucleotide includes the same nucleotide sequence as a reference sequence, or a portion of a reference sequence. In one embodiment, a polynucleotide provided herein is substantially identical to one of the reference sequences SEQ ID NO:1-27, or a portion of a reference sequence. As used herein, the term "substantially identical" means a certain number of nucleotides of the polynucleotide differ from a reference sequence, and the remaining nucleotides are identical to the reference sequence, or a portion of the reference sequence. The number of differences between the polynucleotide and the reference strand may be, may be at least, or may be no greater than 1, 2, 3, 4, 5, 6, 7, 8, 9 or 10 nucleotides. The difference may be a transversion mutation (substitution of a purine for a pyrimidine, or a pyrimidine for a purine) or a transition mutation (substitution of a purine for a purine, or a pyrimidine for a pyrimidine).

In one embodiment, a polynucleotide provided herein includes a sequence that is identical to the complement of a reference sequence selected from any one of SEQ ID NO:1-27. The complement of a reference sequence is also referred to herein as the antisense of that reference sequence. In this context, the term "identical" means the nucleotide sequence of the polynucleotide includes the same nucleotide sequence as the complement of a reference sequence, or a portion of the reference sequence. In one embodiment, a polynucleotide provided herein is substantially identical to the complement of one of the reference sequences SEQ ID NO:1-27. In this context, the term "substantially identical" means a certain number of nucleotides of the antisense strand differ from the complement of a reference sequence, and the remaining nucleotides are identical to the complement of the reference sequence, or a portion of the reference sequence. The number of differences between the antisense strand and the complement of the reference strand may be, may be at least, or may be no greater than 1, 2, 3, 4, 5, 6, 7, 8, 9 or 10 nucleotides. The difference may be a transversion mutation or a transition mutation.

In one embodiment, a polynucleotide is selected from a tRT that is derived from a tRNA that specifies the amino acid cysteine and has the anticodon GCA. An example of one such polynucleotide is SEQ ID NO:1, and the complement thereof.

In one embodiment, a polynucleotide is selected from a tRT that is derived from a tRNA that specifies the amino acid glutamine. In one embodiment, the anticodon may be CTG, and examples of such polynucleotide include SEQ ID NO:2, 3, and/or 4, and the complements thereof. In one embodiment, the anticodon may be TTG, and an example of such a polynucleotide includes SEQ ID NO:5, and the complement thereof.

In one embodiment, a polynucleotide is selected from a tRT that is derived from a tRNA that specifies the amino acid glutamic acid. In one embodiment, the anticodon may be CTC, and examples of such polynucleotides include SEQ ID NO:6 and/or 7, and the complements thereof. In one embodiment, the anticodon may be TTC, and examples of such polynucleotides include SEQ ID NO: 8, 9, and or 10, and the complements thereof.

In one embodiment, a polynucleotide is selected from a tRT that is derived from a tRNA that specifies the amino acid glycine. In one embodiment, the anticodon may be GCC, and examples of such polynucleotides include SEQ ID NO: 11, 13, and/or 14, and the complements thereof. In one embodiment, the anticodon may be TCC, and examples of such polynucleotides include SEQ ID NO: 15 and/or 16, and the complements thereof. In one embodiment, the anticodon may be CCC, and an example of such a polynucleotide includes SEQ ID NO: 12, and the complement thereof.

In one embodiment, a polynucleotide is selected from a tRT that is derived from a tRNA that specifies the amino acid histidine and has the anticodon GTG. An example of one such polynucleotide is SEQ ID NO:17, and the complement thereof.

In one embodiment, a polynucleotide is selected from a tRT that is derived from a tRNA that specifies the amino acid leucine and has the anticodon TAA. An example of one such polynucleotide is SEQ ID NO:18, and the complement thereof.

In one embodiment, a polynucleotide is selected from a tRT that is derived from a tRNA that specifies the amino acid lysine. In one embodiment, the anticodon may be CTT, and examples of such polynucleotides include SEQ ID NO: 19, 20, and/or 21, and the complements thereof. In one embodiment, the anticodon may be TTT, and examples of such polynucleotides include SEQ ID NO:22, and the complement thereof.

In one embodiment, a polynucleotide is selected from a tRT that is derived from a tRNA that specifies the amino acid methionine and has the anticodon CAT. An example of one such polynucleotide is SEQ ID NO:23, and the complement thereof.

In one embodiment, a polynucleotide is selected from a tRT that is derived from a tRNA that specifies the amino acid phenylalanine and has the anticodon GAA. An example of one such polynucleotide is SEQ ID NO:24, and the complement thereof.

In one embodiment, a polynucleotide is selected from a tRT that is derived from a tRNA that specifies the amino acid serine and has the anticodon GCT. An example of one such polynucleotide is SEQ ID NO:25, and the complement thereof.

In one embodiment, a polynucleotide is selected from a tRT that is derived from a tRNA that specifies the amino acid valine. In one embodiment, the anticodon may be AAC, and an example of such a polynucleotide includes SEQ ID NO:26, and the complements thereof. In one embodiment, the anticodon may be CAC, and an example of such a polynucleotide includes SEQ ID NO:27, and the complements thereof.

A polynucleotide provided herein may be, may be at least, or may be no greater than 20, 21, 22, 23, 24, 25, 26, 27, 28, 29, 30, or 31 nucleotides in length. In one embodiment, the polynucleotide is selected from any 20 to 31 consecutive nucleotides of a reference sequence. In those embodiments where the polynucleotide is an antisense, the polynucleotide is selected from any 20 to 31 consecutive nucleotides of the complement of a reference sequence. Thus, non-limiting examples of a polynucleotide based on a reference sequence of 28 nucleotides (SEQ ID NO:23) may be at least nucleotides 1-20, 2-21, 3-22, 4-23, 5-24, 6-25, 7-26, 8-27, or 9-28 of the reference sequence, or the complement thereof non-limiting examples of a polynucleotide based on a reference sequence of 29 nucleotides (SEQ ID NOs:1, 3, 4, 11, 12, 13, 14, 16, 26, or 27) may be at least nucleotides 1-20, 2-21, 3-22, 4-23, 5-24, 6-25, 7-26, 8-27, 9-28, or 10-29 of the reference sequence, or the complement thereof non-limiting examples of a polynucleotide based on a reference sequence of 30 nucleotides (SEQ ID NOs:5, 7, 9, 19, 21, or 22) may be at least nucleotides 1-20, 2-21, 3-22, 4-23, 5-24, 6-25, 7-26, 8-27, 9-28, 10-29, or 11-30 of the reference sequence, or the complement thereof and non-limiting examples of a polynucleotide based on a reference sequence of 31 nucleotides (SEQ ID NOs:2, 6, 8, 10, 17, 18, 20, or 24) may be at least nucleotides 1-20, 2-21, 3-22, 4-23, 5-24, 6-25, 7-26, 8-27, 9-28, 10-29, 11-30, or 12-31 of the reference sequence, or the complement thereof.

By way of example and not intended to be limiting, examples of polynucleotides that are identical to the reference SEQ ID NO:6 include, but are not limited to, 5'-TCCCTGGTGGTCTAGTGGTTA (nucleotides 1-21 of SEQ ID NO:6), 5'-TGGTCTAGTGGTTAGGATTCGGC (nucleotides 8-30 of SEQ ID NO:6), and 5'-TGGTGTCTAGTGGTTAGGATTCGGCG (nucleotides 5-31 of SEQ ID NO:6). Each of these non-limiting examples may be substantially identical to SEQ ID NO:6 through the inclusion of 1, 2, 3, 4, 5, 6, 7, 8, 9, or 10 differences compared to SEQ ID NO:6. A polynucleotide that is identical to a reference sequence but is less than the full length of the reference sequence may be referred to as a mimic. Also by way of example and not intended to be limiting, examples of polynucleotides that are the antisense of the reference SEQ ID NO:6 include, but are not limited to, 5'-TAACCACTAGACCACCAGGGA (SEQ ID NO:73, which is the antisense of nucleotides 1-21 of SEQ ID NO:6), 5'-GCGAATCCTAACCACTAGACCA (SEQ ID NO:74, which is the antisense of nucleotides 8-30 of SEQ ID NO:6), and 5'-CGCCGAATCCTAACCACTAGACCACCA (SEQ ID NO:75, which is the antisense of nucleotides 5-31 of SEQ ID NO:6). Each of these non-limiting examples may be substantially identical to the complement of SEQ ID NO:6 through the inclusion of 1, 2, 3, 4, 5, 6, 7, 8, 9, or 10 differences compared to the complement of SEQ ID NO:6.

MicroRNAs (miRNA) of eukaryotic cells have a seed region of 6 to 8 nucleotides in length at the 5' end that is thought to be an important determinant of target specificity. In contrast, the polynucleotides described herein may have a determinant of target specificity that includes nucleotides located at the 3' end of a reference polynucleotide. As used herein, the "3' domain" of a reference polynucleotide refers to the last 10 nucleotides of a reference sequence. For instance, when the reference sequence is SEQ ID NO:6, the 3' domain is GGATTCGGCG (nucleotides 22-31 of SEQ ID NO:6), and when the reference sequence is SEQ ID NO:23, the 3' domain is AAGCGTGCTG (nucleotides 19-28 of SEQ ID NO:23). In one embodiment, a polynucleotide described herein may include nucleotides that correspond to, or are the complement of, the 3' domain of a reference sequence. For instance, a polynucleotide may include, may include at least, or may include no greater than 9, 8, 7, 6, 5, 4, 3, 2, or 1 nucleotide that corresponds to, or are the complement of, the 3' domain of a reference sequence. As used herein, the "5' domain" of a reference polynucleotide refers to the nucleotides that are at the 5' end of the sequence and do not include the last 10 nucleotides (the 3' domain) of a reference sequence selected from any one of SEQ ID NO:1-27. Thus, a 5' domain includes between 18 and 21 nucleotides. For instance, the 5' domain of the reference polynucleotide SEQ ID NO:6 is TCCCTGGTGGTCTAGTGGTTA (nucleotides 1-21 of SEQ ID NO:6), and the 5' domain of the reference polynucleotide SEQ ID NO:23 is AGCAGAGTGGCGCAGCGG (nucleotides 1-18 of SEQ ID NO:23). In one embodiment, a polynucleotide described herein may include nucleotides that correspond to, or are the complement of, the 5' domain of a reference sequence. For instance, a polynucleotide may include, may include at least, or may include no greater than 21, 20, 19, 18, 17, 16, 15, 14, 13, 12, 11, or 10 nucleotides that correspond to, or are the complement of, the 5' domain of a reference sequence.

When a polynucleotide is substantially identical to a reference sequence or the antisense of a reference sequence, the differences between the polynucleotide and the reference sequence may be localized to a specific region. In one embodiment, the differences between the polynucleotide and the reference sequence are localized to those nucleotides that are located in the 5' domain of the reference polynucleotide. In one embodiment, a polynucleotide described herein may have a sequence that differs from the reference sequence at 1, 2, 3, 4, 5, 6, 7, 8, 9 or 10 nucleotides that correspond to, or are the complement of, the 5' domain of the reference sequence. In one embodiment, the differences between the polynucleotide and the reference sequence are localized to those nucleotides that are located in the 3' domain of the reference polynucleotide. A polynucleotide described herein may have a sequence that differs from the reference sequence at 1 or 2 nucleotides that correspond to the 3' domain of the reference sequence.

In one embodiment, the nucleotide sequence of a polynucleotide is selected from consecutive nucleotides of a reference sequence to optimize the formation of a duplex. In one embodiment, the duplex formed is similar to the D-loop present in the tRNA from which the tRF is derived.

Polynucleotides described herein are biologically active. A biologically active polynucleotide causes alteration of replication of a Respiratory Syncytial Virus (RSV) in a cell. The alteration may be an increase in replication, or a decrease in replication. Without intending to be limited by theory, in one embodiment, after introduction into a cell a polynucleotide described herein is believed to hybridize with a target mRNA in the cytoplasm, repress the target mRNA, and promote RSV replication. Again without intending to be limited by theory, in another embodiment, after introduction into a cell a polynucleotide described herein (e.g., an antisense polynucleotide described herein) is believed to hybridize with a target tRF in the cytoplasm, repress the effect of the target tRF, and inhibit RSV replication. Whether the replication of an RSV in a cell is altered can be determined using methods known and routine in the art. In one embodiment, measuring RSV replication includes infecting cells with RSV, and incubating the cells under conditions suitable for replication of the virus. Suitable cells include epithelial cells, such as A549 (a human alveolar type II-like epithelial cell line), 293 (a human embryonic kidney epithelial cell line), and other cells such as Hep-2. RSV used to infect the cells may be at any suitable multiplicity of infection (MOI), and in one embodiment the MOI is 3. After a suitable time, the titer of virus in the supernatant is determined. Methods for determining RSV titers include the use of commercially available anti-RSV antibody and immunostaining, as described by Ren et al. (2011, J Gen Virol., 92(Pt 9):2153-2159). In one embodiment, replication is considered to be increased when the number of virus (typically referred to a plaque-forming units, or pfu) resulting from infected cells increase by at least 150%, at least 200% (two-fold), at least 300% (three-fold), at least 400% (four-fold), or at least 500% (five-fold), compared to an appropriate control cell. In one embodiment, replication is considered to be decreased when the number of virus resulting from infected cells decrease by at least 150%, at least 200% (two-fold), at least 300% (three-fold), at least 400% (four-fold), or at least 500% (five-fold), compared to an appropriate control cell.

Polynucleotides described herein may be modified. Such modifications can be useful to increase stability of the polynucleotide in certain environments. Modifications can include a nucleic acid sugar, base, or backbone, or any combination thereof. The modifications can be synthetic, naturally occurring, or non-naturally occurring. A polynucleotide of the present invention can include modifications at one or more of the nucleic acids present in the polynucleotide. Examples of backbone modifications include, but are not limited to, phosphonoacetates, thiophosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. In one embodiment the modification results in a morpholino. For instance, in one embodiment, the bases or a polynucleotide are bound to morpholine rings instead of deoxyribose rings, and linked through phosphorodiamidate groups instead of phosphates. Polynucletotides can be obtained commercially synthesized to include such modifications (for instance, Dharmacon Inc., Lafayette, Colo.).

Vectors

A polynucleotide described herein can be encoded by a vector. A vector is a replicating polynucleotide, such as a plasmid, phage, or cosmid, to which another polynucleotide may be attached so as to bring about the replication of the attached polynucleotide. Construction of vectors encoding a polynucleotide described herein employs standard ligation techniques known in the art. See, e.g., Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, transposon vectors, and artificial chromosome vectors. Examples of viral vectors include, for instance, adenoviral vectors, adeno-associated viral vectors, lentiviral vectors, retroviral vectors, and herpes virus vectors. A vector may result in integration into a cell's genomic DNA. A vector may be capable of replication in a bacterial host, for instance *E. coli*. A vector may be capable of introducing a polynucleotide into a eukaryotic cell. A polynucleotide present in a vector may include a coding region that encodes a polynucleotide described herein. A "coding sequence" as used herein refers to a polynucleotide that encodes an RNA and, when placed under the control of appropriate regulatory sequences, expresses the encoded RNA.

Selection of a vector depends upon a variety of desired characteristics in the resulting construct, such as a selection marker, vector replication rate, type of cell in which it is to be introduced and optionally replicate, and the like. Suitable host cells for cloning or expressing the vectors herein are prokaryotic or eukaryotic cells. Suitable eukaryotic cells include mammalian cells, such as murine cells and human cells. Suitable prokaryotic cells include eubacteria, such as gram-negative organisms, for example, *E. coli.*

An expression vector optionally includes regulatory sequences operably linked to a sequence encoding a polynucleotide described herein. A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

In one embodiment, a vector may include operably linked RNA regulatory sequences, such as a binding site for an RNA polymerase I promoter, an RNA polymerase II promoter, or an RNA polymerase III promoter, that results in the production of an RNA polynucleotide.

In another embodiment, a vector may include constitutive, inducible, and/or tissue specific promoters for expression of a polynucleotide described herein in a particular tissue or intracellular environment, examples of which are known to one of ordinary skill in the art. Constitutive mammalian promoters include, but are not limited to, polymerase promoters as well as the promoters for the following genes: hypoxanthine phosphoribosyl transferase (HPTR), adenosine deaminase, pyruvate kinase, and β-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art.

Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include, but are not limited to, tissue-specific expression elements for the lung such as, but are not limited to, the cystic fibrosis transmembrane conductance regulator gene promoter, and the lung epithelial cell-specific surfactant protein B (SPB) gene promoter.

Methods of Making

Polynucleotides described herein can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are well known. Methods for in vitro synthesis also include, for instance, in vitro transcription using a circular or linear expression vector in a cell free system, such as a cell lysate. Expression vectors can also be used to produce a polynucleotide described herein in a cell, and the polynucleotide may then be isolated from the cell.

Whether a polynucleotide alters RSV replication may be determined by the use of ex vivo and/or in vivo cells. A candidate polynucleotide is the polynucleotide that is being tested to determine if it alters RSV replication. In general, candidate polynucleotides are individually tested by introducing a candidate polynucleotide into a cell that contains RSV. The candidate polynucleotides may be prepared in vitro and then introduced into a cell. The candidate polynucleotides may also be prepared by introducing into a cell a vector that encodes the candidate polynucleotide.

A cell that can be used to evaluate a candidate polynucleotide is a cell that supports the replication of RSV. A cell can be ex vivo or in vivo. As used herein, the term "ex vivo" refers to a cell that has been removed from the body of a subject. Ex vivo cells include, for instance, primary cells (e.g., cells that have recently been removed from a subject and are capable of limited growth in tissue culture medium), and cultured cells (e.g., cells that are capable of extended culture in tissue culture medium). Examples of primary cells include cells normally present in an animal's respiratory tract. A cell may be obtained from a subject by, for example, bronchioalveolar lavage. As used herein, the term "in vivo" refers to a cell that is within the body of a subject. For instance, an in vivo cell may be a cell present in the respiratory tract of a subject.

Examples of readily available cells useful for replication of RSV and evaluating the biological activity of a candidate polynucleotide include cultured cells such as, but not limited to, A549 cells, 293 cells, and HEp-2 cells, all of which are available from the ATCC. Sources of other suitable cells include primary cells obtained from biopsy, such as cells present in a the respiratory tract including, but not limited to, superficial cells of the respiratory epithelium, ciliated cells of the small bronchioles, and type 1 pneumocytes of the alveoli.

Candidate polynucleotides may also be tested in animal models. The study of RSV infection in animal models (for instance, chimpanzees, cattle, sheep, cotton rats, and mice) is a commonly accepted practice for the study of RSV pathogenesis (see, for instance, Collins and Graham, 2008, J. Virol., 82:2040-2055, and Bem et al., 2011, Am, J. Physiol. Lung Cell. Mol. Physiol., 301(2):L148-156). Candidate polynucleotides can be used in these and other animal models to determine if a candidate polynucleotide decreases replication of RSV, and/or decreased one or more symptoms and/or signs associated with disease.

Methods for introducing a candidate polynucleotide into a cell, including a vector encoding a candidate polynucleotide, are known in the art and routine. Transfection and transduction refer to the introduction of a polynucleotide into a cell. Transfection can occur by physical or chemical methods. Many transfection techniques are known to the skilled person including, but not limited to, calcium phosphate DNA co-precipitation, DEAE-dextrin DNA transfection, electroporation, naked plasmid adsorption, cationic liposome-mediated transfection (commonly known as lipofection). Transduction refers to the process of introducing a polynucleotide into a cell using a DNA or RNA virus.

A polynucleotide described herein may be used in combination with other agents assisting the cellular uptake of polynucleotides, or assisting the release of polynucleotides from endosomes or intracellular compartments into the cytoplasm or cell nuclei by, for instance, conjugation of those other agents to the polynucleotide. The agents may be, but are not limited to, peptides, especially cell penetrating peptides, protein transduction domains, cholesterol moiety, and/or dsRNA-binding domains which enhance the cellular uptake of polynucleotides (Dowdy et al., US Published Patent Application 2009/0093026, Eguchi et al., 2009, *Nature Biotechnology* 27:567-571, Lindsay et al., 2002, Curr. Opin. Pharmacol., 2:587-594, Wadia and Dowdy, 2002, Curr. Opin. Biotechnol. 13:52-56. Gait, 2003, Cell. Mol. Life Sci., 60:1-10). The conjugations can be performed at an internal position at the polynucleotide or at a terminal position at either the 5'-end or the 3'-end.

Toxicity and therapeutic efficacy of a polynucleotide can be determined by standard pharmaceutical procedures in cell cultures or experimental animals, e.g., for determining the $ED_{50}$ (the dose therapeutically effective in 50% of the population).

The data obtained from cell culture assays and animal studies can be used in formulating a range of dosage for use in humans. The dosage of such active compounds lies preferably within a range of concentrations that include the $ED_{50}$ with little or no toxicity. The dosage may vary within this range depending upon the dosage form employed and the route of administration utilized. For a polynucleotide used in the methods described herein, it may be possible to estimate the therapeutically effective dose initially from cell culture assays. A dose may be formulated in animal models to achieve a concentration range that includes the $IC_{50}$ (i.e., the concentration of the test compound which achieves a half-maximal inhibition of signs and/or symptoms) as determined in cell culture. Such information can be used to more accurately determine useful doses in humans.

Compositions

Also provided are compositions including one or more polynucleotides described herein. Such compositions typically include a pharmaceutically acceptable carrier. As used herein "pharmaceutically acceptable carrier" includes, but is not limited to, saline, solvents, dispersion media, coatings, antibacterial and antifungal agents, isotonic and absorption delaying agents, and the like, compatible with pharmaceutical administration. Additional compounds can also be incorporated into the compositions. Additional compounds include, for instance, antiviral agents such as ribavirin, corticosteroids, bronchodilators, palivizumab, tumor necrosis factor alpha, interferon beta, type I, II and III interferons, and the like.

A composition may be prepared by methods well known in the art of pharmacy. In general, a composition can be formulated to be compatible with its intended route of administration. A formulation may be solid or liquid. Administration may be systemic or local. In some aspects local administration may have advantages for site-specific, targeted disease management. Local therapies may provide high, clinically effective concentrations directly to the treatment site, with less likelihood of causing systemic side effects.

Examples of routes of administration include parenteral (e.g., intravenous, intradermal, subcutaneous, intraperitoneal, intramuscular), enteral (e.g., oral), and topical (e.g., epicutaneous, inhalational, transmucosal) administration. Appropriate dosage forms for enteral administration of a polynucleotide may include tablets, capsules or liquids. Appropriate dosage forms for parenteral administration may include intravenous administration. Appropriate dosage forms for topical administration may include nasal sprays, metered dose inhalers, dry-powder inhalers or by nebulization.

Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., a polynucleotide described herein) in the required amount in an appropriate solvent with one or a combination of ingredients such as those enumerated above, as required, followed by filtered sterilization. Generally, dispersions are prepared by incorporating the active compound into a sterile vehicle, which contains a dispersion medium and other ingredients such as from those enumerated above. In the case of sterile powders for the preparation of sterile injectable solutions, methods of preparation that may be used include vacuum drying and freeze-drying which yields a powder of the active ingredient plus any additional desired ingredient from a previously sterile-filtered solution thereof.

For administration by inhalation, the active compounds may be delivered in the form of an aerosol spray, a nebulizer, or an inhaler, such as a nasal spray, metered dose inhaler, or dry-powder inhaler.

Oral compositions may include an inert diluent or an edible carrier. For the purpose of oral therapeutic administration, the active compound can be incorporated with excipients and used in the form of tablets, troches, or capsules. Oral compositions can also be prepared using a fluid carrier. Pharmaceutically compatible binding agents can be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds may be formulated into ointments, salves, gels, or creams as generally known in the art. An example of transdermal administration includes iontophoretic delivery to the dermis or to other relevant tissues.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially. Liposomal suspensions can also be used as pharmaceutically acceptable carriers. These can be prepared according to methods known to those skilled in the art. Delivery reagents such as lipids, cationic lipids, phospholipids, liposomes, nanoparticles, and microencapsulation may also be used.

In one embodiment, an active compound may be associated with a targeting group. As used herein, a "targeting group" refers to a chemical species that interacts, either directly or indirectly, with the surface of a cell, for instance with a molecule present on the surface of a cell, e.g., a receptor. The interaction can be, for instance, an ionic bond, a hydrogen bond, a Van der Waals force, or a combination thereof. Examples of targeting groups include, for instance, saccharides, polypeptides (including hormones), polynucleotides, fatty acids, and catecholamines. Another example of a targeting group is an antibody. The interaction between the targeting group and a molecule present on the surface of a cell, e.g., a receptor, may result in the uptake of the targeting group and associated active compound.

When a polynucleotide is introduced into cells using a suitable technique, the polynucleotide may be delivered into the cells by, for example, transfection or transduction procedures. A polynucleotide described herein may be used in combination with other agents assisting the cellular uptake of polynucleotides, or assisting the release of polynucleotides from endosomes or intracellular compartments into the cytoplasm or cell nuclei by, for instance, conjugation of those to the polynucleotide. Introduction of a polynucleotide into a cell may further include the use of methods to permeabilize the glycocalyx and epithelium of the respiratory tract, such as temporary water-induced hypoosmotic shock (Kolb et al., 2006, Chest, 130:879-884).

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polynucleotide can include a single treatment or can include a series of treatments.

Methods of Use

The present invention includes methods for using the polynucleotides disclosed herein. In one embodiment, a method includes contacting a cell with an effective amount of at least one polynucleotide described herein. In one embodiment, the contacting is under conditions suitable for introduction of at least one polynucleotide into the cell. The polynucleotide introduced into a cell may be single stranded RNA, single stranded DNA, or a single stranded molecule that is a hybrid, e.g., made up of some nucleotides that are DNA and some that are RNA. In one embodiment, the polynucleotide is introduced into a cell as a vector that encodes the single stranded RNA or DNA molecule. The polynucleotide may be present in a composition.

In one embodiment, the polynucleotide introduced into a cell includes a nucleotide sequence that is substantially identical, or identical, to a reference sequence. In one embodiment, the polynucleotide introduced into a cell includes a nucleotide sequence that is substantially identical, or identical, to the complement of a reference sequence. In one embodiment, the reference sequence is at least 20 consecutive nucleotides selected from first 28 to 31 nucleotides at the 5' end of a mature tRNA. Examples of such 28 to 31 nucleotide sequences are shown at SEQ ID NO:1-27. In one embodiment, the mature tRNA is selected from a tRNA that specifies cysteine and has the anticodon GCA (SEQ ID NO:1), specifies glutamine and has the anticodon CTG (SEQ ID NOs:2, 3, or 4) or TTG (SEQ ID NO:5), specifies glutamic acid and has the anticodon CTC (SEQ ID NOs:6 or 7) or TTC (SEQ ID NOs:8, 9, or 10), specifies glycine and has the anticodon GCC (SEQ ID NOs:11, 13, or 14), TCC (SEQ ID NO:15), or CCC (SEQ ID NO:12), specifies histidine and has the anticodon GTG (SEQ ID NO:17), specifies leucine and has the anticodon TAA (SEQ ID NO:18), specifies lysine and has the anticodon CTT (SEQ ID NOs:19, 20, or 21) or TTT (SEQ ID NO:22), specifies methionine and has the anticodon CAT (SEQ ID NO:23), specifies phenylalanine and has the anticodon GAA (SEQ ID NO:24), specifies serine and has the anticodon GCT (SEQ ID NO:25), specifies valine and has the anticodon AAC (SEQ ID NO:26) or CAC (SEQ ID NO:27), or a combination thereof.

Conditions that are "suitable" for an event to occur, such as introduction of a polynucleotide into a cell, or "suitable" conditions are conditions that do not prevent such events from occurring. Thus, these conditions permit, enhance, facilitate, and/or are conducive to the event. As used herein, an "effective amount" relates to a sufficient amount of a polynucleotide to provide the desired effect. For instance, in one embodiment an "effective amount" is an amount effective to alter the replication of RSV in a cell. The method may result in decreasing replication of RSV, or increasing replication of RSV. In one embodiment, replication is considered to have increased or decreased if there is a statistically significant change compared to a control cell not contacted with the polynucleotide. In one embodiment, replication is considered to be increased when the number of virus resulting from infected cells increase by at least 150%, at least 200% (two-fold), at least 300% (three-fold), at least 400% (four-fold), or at least 500% (five-fold), compared to an control cell not contacted with the polynucleotide. In one embodiment, replication is considered to be decreased when the number of virus resulting from infected cells decrease by at least 150%, at least 200% (two-fold), at least 300% (three-fold), at least 400% (four-fold), or at least 500% (five-fold), compared to an appropriate control cell not contacted with the polynucleotide. A cell that may be used in the methods described herein may be ex vivo or in vivo.

In one embodiment, the methods are for altering RSV replication in a cell. In one embodiment RSV replication is increased, and in one embodiment RSV replication is decreased. The method includes contacting a cell with an effective amount of a polynucleotide described herein. In embodiments where RSV replication is to be increased, the polynucleotide includes a nucleotide sequence that is substantially identical, or identical, to a reference sequence. In embodiments where RSV replication is to be decreased, the polynucleotide includes a nucleotide sequence that is substantially identical, or identical, to the complement of a reference sequence. In one embodiment, the cell already includes RSV when the polynucleotide is introduced into the cell. In one embodiment, the method also includes introducing into the cell at least one RSV. The introduction of the RSV may be before, during, or after the polynucleotide is introduced. The cell may be an ex vivo cell, such as a primary cell or a cultured cell. In one embodiment, the cell is an in vivo cell. The cell, whether ex vivo or in vivo, may be a human cell, a chimpanzee cell, a cow cell, a sheep cell, a cotton rat cell, or a mouse cell. In embodiments where the in vivo cell is present in a human, the human is between 0 and 24 months of age.

Also provided herein are methods for treating an infection in an animal, including a human, caused by RSV. In one embodiment, a human that is the subject of a method described herein may be an age between 0 and 2 years, such as an age after birth and before 1 year. The method includes administering an effective amount of polynucleotide described herein to an animal having, or at risk of having, an infection caused by an RSV. Optionally, the method also includes determining whether the number of virus causing the infection has decreased. As used herein, the term "infection" refers to the presence of RSV an animal's body, which may or may not be clinically apparent. An animal with an infection by RSV that is not clinically apparent is often referred to as an asymptomatic carrier.

In another aspect, the present invention is directed to methods for treating one or more symptoms or clinical signs of an RSV infection in an animal, such as a human. The method includes administering an effective amount of a polynucleotide described herein to a subject having or at risk of having a condition, or exhibiting symptoms and/or clinical signs of a condition. Optionally, the method also includes determining whether at least one symptom and/or clinical sign of the condition is changed, preferably, reduced. Examples of conditions and/or clinical signs caused by an RSV infection include, for instance, listlessness, poor or diminished appetite, possible fever, bronchiolitis, and pneumonia. A symptom and/or sign may be localized to, for instance, a subject's upper and/or lower respiratory tract.

Treatment of an infection, symptoms and/or clinical signs associated with an RSV infection can be prophylactic or, alternatively, can be initiated after the development of an RSV infection. As used herein, the term "symptom" refers to subjective evidence of the infection experienced by the subject and caused by virus. As used herein, the term "clinical sign" or, simply, "sign" refers to objective evidence of disease or condition caused by an RSV infection. Symptoms and/or clinical signs associated with an RSV infection and the evaluations of such symptoms are routine and known in the art. Treatment that is prophylactic, for instance, initiated before a subject manifests symptoms or signs of an RSV infection, is referred to herein as treatment of a subject that is "at risk" of developing the infection. Thus, typically, an animal "at risk" of developing an RSV infection is an animal present in an area where animals having the condition have been diagnosed and/or is likely to be exposed to the virus causing the condition even if the animal has not yet manifested symptoms or signs of any condition caused by the virus. Accordingly, administration of a composition can be performed before, during, or after the subject has first contact with the virus, or the occurrence of the conditions described herein. Treatment initiated after the subject's first contact with the virus may result in decreasing the infection by the virus, completely removing the infection, and/or decreasing the likelihood of experiencing a clinically evident infection (e.g., symptoms and/or signs) compared to an animal to which the polynucleotide is not administered. Treatment initiated after the development of a condition may result in decreasing the severity of the symptoms of the infection, or completely removing the symptoms.

The polynucleotides described herein may also be administered to a subject in combination with other therapeutic compounds to increase the overall therapeutic effect. Therapeutic compounds useful for the treatment of an RSV infection are known and used routinely. Therapeutic compounds may include antiviral agents such as ribavirin, corticosteroids, bronchodilators, palivizumab, and the like.

Also provided herein are methods for reducing replication of RSV in a cell through the use of APOER2 (also known in the art as LRP-8. The method includes introducing into a cell APOER2 protein, or a polynucleotide encoding APOER2. In one embodiment, the cell already includes RSV when the APOER2 is introduced into the cell. In one embodiment, the method also includes introducing into the cell at least one RSV. The introduction of the RSV may be before, during, or after the APOER2 is introduced. The cell may be an ex vivo cell, such as a primary cell or a cultured cell. In one embodiment, the cell is an in vivo cell. The cell, whether ex vivo or in vivo, may be a human cell, a chimpanzee cell, a cow cell, a sheep cell, a cotton rat cell, or a mouse cell. In embodiments where the in vivo cell is present in a human, the human is between 0 and 24 months of age.

Also provided herein are methods for making RSV. The methods include incubating a cell that contains RSV and at least one polynucleotide described herein that promotes RSV replication. The incubating occurs under conditions that are suitable for replication of the virus, and the cell used in one that is permissive for RSV replication. After a suitable amount of time the virus particles that have been released from the cell can be removed from the cells using routine methods.

Animal models are commonly accepted models for the study of human disease caused by RSV; however, a disadvantage of studying RSV in animal models is the limited replication of the virus in the animal tissues. The polynucleotides described herein that promote RSV replication may increase the usefulness of animal models in the study of RSV. Accordingly, further provided herein are animal models and methods for using the animal models in evaluating viral and host factors in human RSV pathogenesis. The animal may be, but is not limited to, chimpanzees, cattle, sheep, cotton rats, and mice. The animal includes a polynucleotide that promotes RSV replication, and RSV. The polynucleotide that promotes RSV replication may be administered to the animal, or the animal may be modified to include cells that express the polynucleotide. This used to study, for instance, host risk factors, protective and pathogenic features of the host response, pathogenic features of the virus, and the like, thus, also provided herein are methods for using the animal model, including using it to evaluate viral and host factors in RSV pathogenesis.

Also provided herein is a kit for treating RSV infection. The kit includes at least one polynucleotide described herein in a suitable packaging material in an amount sufficient for at least one administration. Optionally, other reagents such as buffers and solutions needed to practice the invention are also included. Instructions for use of the packaged polynucleotide are also typically included.

As used herein, the phrase "packaging material" refers to one or more physical structures used to house the contents of the kit. The packaging material is constructed by known methods, preferably to provide a sterile, contaminant-free environment. The packaging material has a label which indicates that the polynucleotide can be used for treating an RSV infection. In addition, the packaging material contains instructions indicating how the materials within the kit are employed to treat an RSV infection. As used herein, the term "package" refers to a solid matrix or material such as glass, plastic, paper, foil, and the like, capable of holding within fixed limits a polynucleotide. "Instructions for use" typically include a tangible expression describing the reagent concentration or at least one administration parameter, such as the amount of sample to be administered.

The present invention is illustrated by the following examples. It is to be understood that the particular examples, materials, amounts, and procedures are to be interpreted broadly in accordance with the scope and spirit of the invention as set forth herein.

EXAMPLE 1

The discovery of small non-coding RNAs (sncRNAs) with regulatory functions is a recent breakthrough in biology. Among sncRNAs, microRNA (miRNA), derived from host or virus, has emerged as elements with high importance in control of viral replication and host responses. However, the expression pattern and functional aspects of other types of sncRNAs, following viral infection, are unexplored. In order to define expression patterns of sncRNAs, as well as to discover novel regulatory sncRNAs in response to viral infection, we applied deep sequencing to cells infected with human respiratory syncytial virus (RSV), the most common cause of bronchiolitis and pneumonia in babies. RSV infection leads to abundant production of tRNA-derived RNA fragments (tRFs) that are ~30 nucleotides (nts) and correspond to the 5'-half of mature tRNAs. At least one tRF, which is derived from tRNA-Glu-CTC, represses target mRNA in the cytoplasm and promotes RSV replication. This demonstrates that this tRF is not a random by-product of tRNA degradation but a functional molecule. The biogenesis of this tRF is also specific, as it is mediated by the endonuclease angiogenin, not by other nucleases. In summary, our study presents novel information on the induction of a functional tRF by viral infection.

Materials and Methods

Cell lines and virus. HEp-2 cells (ATCC, Manassas, Va.) were maintained in Minimal Essential Medium (MEM) (Invitrogen GIBCO, Carlsbad, Calif.) supplemented with 10% fetal bovine serum (FBS) and penicillin and streptomycin (100 U/ml). A549, human alveolar type II-like epithelial cells, and 293, a human embryonic kidney epithelial cell line (both from ATCC, Manassas, Va.), were maintained in F12K and MEM medium respectively, containing 10% (v/v) FBS, 10 mM glutamine, 100 IU/ml penicillin and 100 µg/ml streptomycin. Primary cultured SAE cells were grown according to the company instructions (ATCC). RSV A2 strain was grown in HEp-2 cells and purified by sucrose-gradient as described (Guerrero-Plata et al., (2005) J Virol 79:14992-14997). Viral titer was determined by immunostaining in HEp-2 cells using polyclonal biotin-conjugated goat anti-RSV antibody (Ad direct, Barberton, Ohio) and streptavidin peroxidase polymer (Sigma, St. Louis, Mo.) sequentially, as described (Ren et al., (2011) J Gen Virol 92:2153-2159).

Viral infection. A549 or 293 cells were infected with RSV or hMPV, at multiplicity of infection (MOI) of 3. An equivalent amount of sucrose solution was added to uninfected cells, as control (mock infection). After initial absorption, viral inoculum was removed and cells were supplied with fresh medium with 2% FBS. Infected cells were scrapped into the medium, followed by sonication and centrifugation. Viruses in the supernatant were harvested and viral titer was determined by immunostaining in HEp-2 cells as described above.

RNA extraction, deep sequencing, RNA mapping, and expression confirmation of tRFs by Northern blot. Total cellular RNA was extracted by TRIzol® Reagents according to manufacturer's instruction (Invitrogen). The RNAs were delivered to Eureka Genomics (Houston Tex.) for small RNAs isolation, directional adaptor ligation, cDNA library construction, and sequencing using a Genome Analyzer IIx (Illumina). About 485 Mb of sequence data with a total of 32,332,590 sequence reads was generated for mock- and RSV-infected samples, using 36b single-end sequencing reads. The sequence reads≥10 after adaptor sequence removal were sent back for further classification. Small RNAs were mapped using Novoalign software (Novocraft Technologies, Selangor, Malaysia) allowing two mismatches (Li et al., (2009) Bioinformatics 25:2078-2079). After initial alignment, further processing was performed using in-house programs and SAMtools. First, uniquely aligned reads and sequences aligned to more than one genome location (ambiguously aligned reads) were separated. The ambiguously aligned reads were then randomly assigned to one location and combined with uniquely aligned reads for the downstream analysis shown in FIG. 1.

Northern hybridization for sncRNAs were performed as described (Lee et al., (2009) Genes Dev 23:2639-2649). Briefly, RNA was separated in 15% denaturing polyacrylamide gel with 7M urea and then transferred to a positively charged nylon membrane (Amersham Biosciences, Piscataway, N.J.). The membrane was hybridized with $^{32}$P-labeled probes in ULTRAhyb®-Oligo solution (Life Technologies, Grand Island, N.Y.), followed by washing according to the manufacturer's instruction.

Construction of luciferase sensor plasmids and luciferase assays. The sensor plasmid "Pp-anti_GluCTC_WT" was constructed by inserting an oligonucleotide, which was complementary to tRF5-GluCTC, into EcoRI/XhoI sites of pcDNA3.1-Zeo(+)-Pp as described (Lee et al., (2011) RNA 17:1076-1089). Paired primers used for insertion were: 5'-AATTCGCCGAATCCTAACCACTAGACCACCA-GGGA (SEQ ID NO:76) and 5'-TCGATCCCTGGTG-GTCTAGTGGTTAGGATTCGGCG (SEQ ID NO:77) (bold letters represent extra nts to generate EcoRI/XhoI overhangs). Three mutant plasmids were constructed in the same manner (their mutated sequences shown in FIG. 4A). An empty pcDNA3.1-Zeo(+)-Pp vector was used as a control (designated as "Pp-vector").

Figure 4:
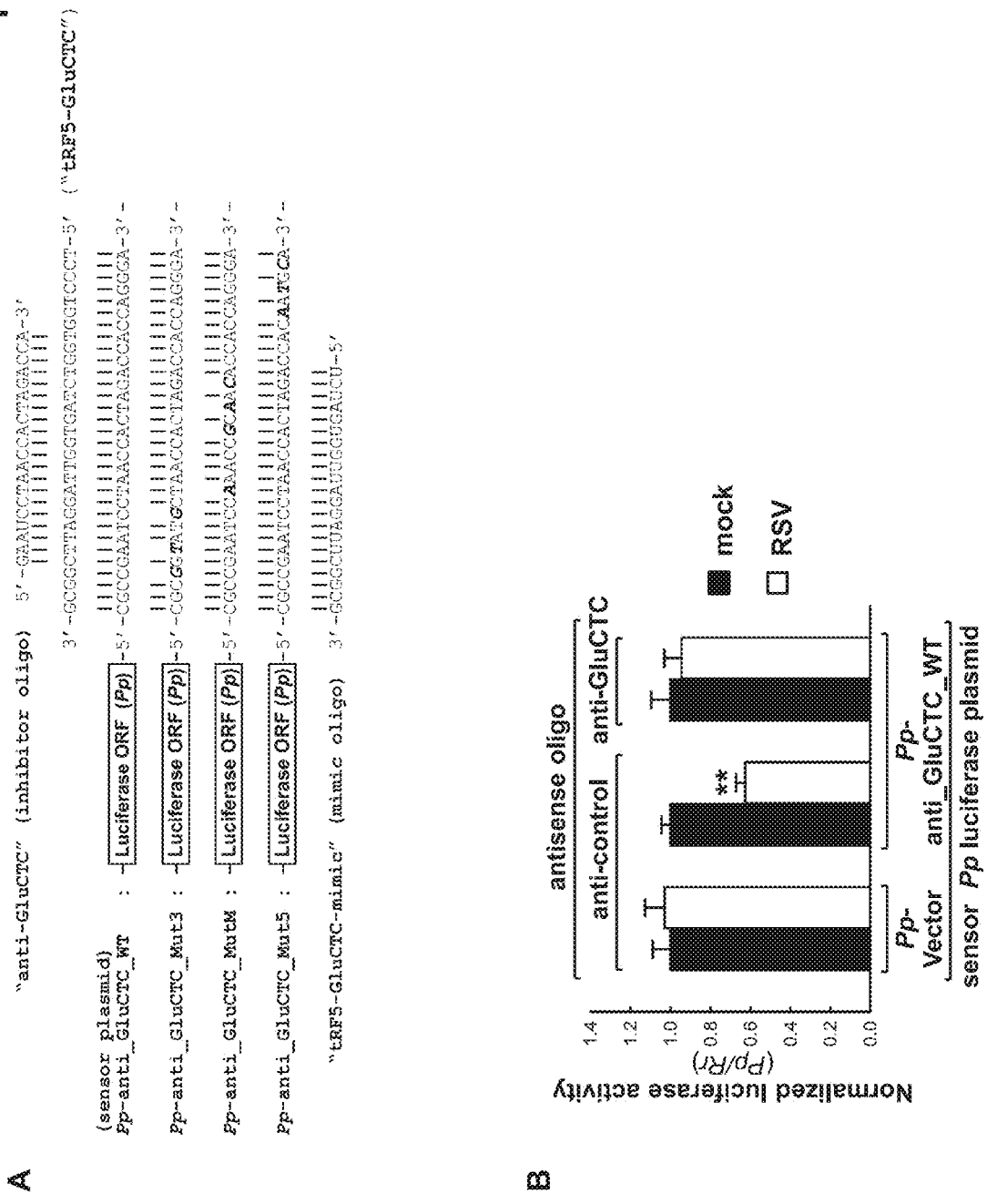
FIG. 4. tRF5-GluCTC exhibits miRNA-/siRNA-like trans-silencing capacity. A. Sequence alignment of Pp-anti_GluCTC_WT (SEQ ID NO:91) with three mutant luciferase sensor plasmids (SEQ ID NOs: 92, 93, and 94). Mutated nts are in bold and italic. The sequence of tRF5-GLuCTC inhibitor and mimic are also present. B. A549 cells in hexaplicate were co-transfected with a firefly (Pp) luciferase reporter plasmid (cognate "Pp-anti_G-luCTC_WT" plasmid or "Pp-vector" plasmid, 0.1 µg/well of 24-well plate), a plasmid expressing renilla (Rr) luciferase, and 120 nM anti-sense oligos ("anti-GluCTC" or "anti-control"). After 2 h post-transfection, cells were mock- or RSV-infected, then harvested at 6 h p.i. to measure luciferase activities. In all experiments, Pp luciferase values were normalized to renilla (Rr) luciferase values from co-transfected pRL-CMV. Values at y-axis (Pp/Rr) are a representative of three independent experiments and are expressed as mean±standard error (SE).  on the second plain bar (RSV-infected and Pp-anti_GluCTC transfected) denotes p value<0.01, relative to the second black bar (mock-infected and Pp-anti_GluCTC transfected). C. A549 cells were treated as described in panel B and total RNA was subjected to Northern hybridization as described at B in FIG. 3 (upper panel). Densitometric analysis of tRF5-GluCTC band intensity, quantified using VisionWorksLS image acquisition and analysis software from UVP (Upland, Calif.) is shown after normalization to 5S rRNA. Data are summarized from three independent experiments (lower panel). D. A549 cells in hexaplicate were transfected with indicated Pp luciferase reporter plasmids. After 24 h post-transfection, cells were mock- or RSV-infected, then harvested at 15 h p.i. to measure luciferase activities. All other descriptions are the same as panel B. E. A549 cells in hexaplicate were transfected with indicated tRF-mimic oligos. Luciferase plasmids, Pp-anti_GluCTC_WT or _Mut3 (0.1 µg/well), with a plasmid expressing Rr luciferase, were co-transfected. After 40 h post-transfection, cells were lysed for luciferase assays. Pp values were first normalized by Rr values, and then the Pp/Rr values of "Pp-anti_GluCTC_WT" were normalized to those of "Pp-anti_GluCTC_Mut3", yielding relative Pp/Rr values (y-axis).  denotes p value<0.01, relative to control-mimic (black bars) in respective concentration. All other descriptions are the same as panel B. miRNA, microRNA; nts, nucleotides; ORF, open reading frame; RSV, respiratory syncytial virus; sieRNA, small-interfering RNA; tRF, tRNA-derived RNA fragment; tRNA, transfer RNA; WT, wild-type. anti-GluCTC, SEQ ID NO:90; tRF5-GluCTC, SEQ ID NO:6; tRF5-GluCTC-mimic, SEQ ID NO:95.
Figure 4:
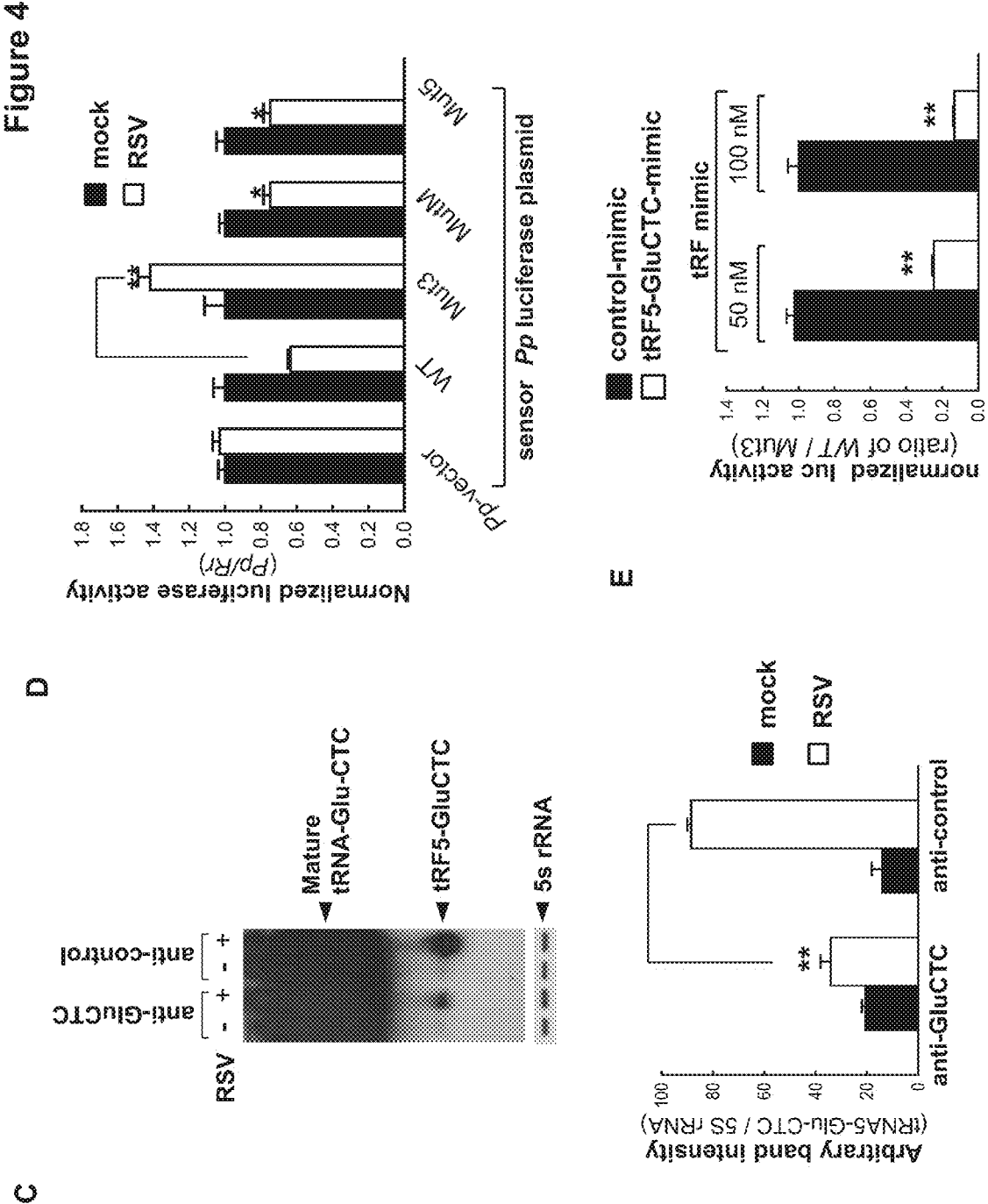

To investigate the effect of RSV-induced tRF5-GluCTC on mRNA expression, A549 cells were co-transfected with Pp-anti_GluCTC sensor plasmids (firefly plasmids), pRL-CMV plasmids expressing Rr (renilla luciferase), and anti-GluCTC oligonucleotides, using Lipofetamine 2000 according to the manufacturer's instruction (Invitrogen). Pp-vector plasmids and/or anti-control oligonucleotides were used as negative controls. After 2 h of transfection, the cells were infected with mock or RSV. At 6 h post infection (p.i.), cells were lysed for luciferase assays using a Dual-luciferase kit (Promega, Madison, Wis.). Data processing and normalization was described in FIG. 4 legend. For this experiment, synthetic anti-GluCTC oligonucleotides were purchased from Integrated DNA Technologies (Coralville, Iowa). They were 20-nt mixed oligonucleotides which contain a backbone phosphorothioate and have 5 nts on each end substituted with 2'-O-methyl ribonucleotides (Yoo et al., (2004) Nucleic Acids Res 32:2008-2016, Ideue et al., (2009) RNA 15:1578-1587). The sequence of "anti-GluCTC" is shown in FIG. 4A and that of "anti-control" is 5'-CCGCUGAGCTAAAGCCAGCC (SEQ ID NO:78).

To identify the functional domain(s) of tRF5-GluCTC, A549 cells were co-transfected with Pp-anti_GluCTC sensor plasmids or their mutants, and Rr expressing plasmids for 24 h, followed by mock or RSV infection (MOI of 1). Cells were lysed for luciferase assays at 15 h post infection.

For ectopic expression of tRF5-GluCTC, dsRNAs with blunt ends were designed (FIG. 4A) and synthesized by Sigma. "Control-mimic" was purchased also from Sigma. A549 cells were co-transfected with the mimics and luciferase sensor plasmids using Lipofectamine 2000. Cells were harvested for dual-luciferase assays at 40 h post transfection. All other descriptions, such as the concentrations of oligonucleotides and plasmids were described in FIGS. 4E and 5E-F.

Protein synthesis assay. Confluent A549 cells, treated with/without antisense oligoribonucleotide and/or RSV infection, were incubated with [$^{35}$S]-methionine (4 µCi in 2 ml of Dulbecco's Modified Eagle Medium containing dialyzed FBS, but no L-glutamine, L-methionine, and L-cystine). Cells were harvested and lysed after 1 hr incubation. The cell lysates were precipitated with 10% trichloroacetic acid, resuspended in 1×SDS-PAGE loading buffer, and loaded onto a 10% SDS-polyacrylamide gel. The gel was stained with Coomassie brilliant blue, dried, and visualized by autoradiography.

RNA interference. siRNAs were purchased from Sigma or Invitrogen. 100 nM of siRNA was transfected into A549 cells, by using Mirus (Madison, Wis.) according to the manufacturer's recommendations. 40 h later, A549 cells were mock- or RSV-infected for 6 h at a MOI of 3.

Quantitative real-time PCR (Q-RT-PCR). Total cellular RNAs were extracted using TRIzol® reagents and viral RNAs released in supernatant were extracted using QIAamp viral RNA kit (Qiagen, Alameda, Calif.). First strand cDNA was synthesized by using TaqMan reverse transcription (RT) reagents (ABI, Carlsbad, Calif.). The RT reaction was performed under the following conditions: 25° C., 10 min; 48° C., 30 min; 95° C., 5 min. Q-RT-PCR amplification was performed by using SYBR Sequence information on green labeled primers for target genes and internal control 18S rRNA is available upon request. QPCR reactions were performed with the FastStart Universal SYBR Green Master (ROX) (Roche, San Francisco, Calif.) in the ABI 7500 Sequence Detection System using following conditions: initial steps: 50° C., 2 min; and 95° C., 10 min; PCR steps: 95° C., 15 sec; and, 60° C., 1 min for 40 cycles. The RT primer to measure the transcription of RSV N gene is:

(SEQ ID NO: 79)
5'-CTGCGATGAGTGGCAGGCTTTTTTTTTTTTAACTAAAGCTC;

Primers were designed to incorporate a "tag" (underlined letters) as part of the assay due to self priming exhibited by RSV viral RNA (Bannister et al., (2010) Virol J 7:250). The tag sequence was derived from the bacterial chloroamphenicol resistance (Cmr) gene. Sequence with bold letters is complementary to poly A tails of transcribed RSV N gene. Sequence in italic is N gene specific. At 25° C. annealing temperature, the N specific sequences would not be sufficient for a stable efficient priming of cDNA from an antigenome of RSV (positive strand). PCR primers for N gene transcription assays are:

(Forward)
(SEQ ID NO: 80)
5'-ACTACAGTGTATTAGACTTRACAGCAGAAG
and (Reverse)
(SEQ ID NO: 81)
5'-CTGCGATGAGTGGCAGGC.

Statistical Analysis. Statistical significance was analyzed using analysis of variance (ANOVA). P value of less than 0.05 was considered significant. Mean±standard error (SE) is shown.

Results

Figure 1:
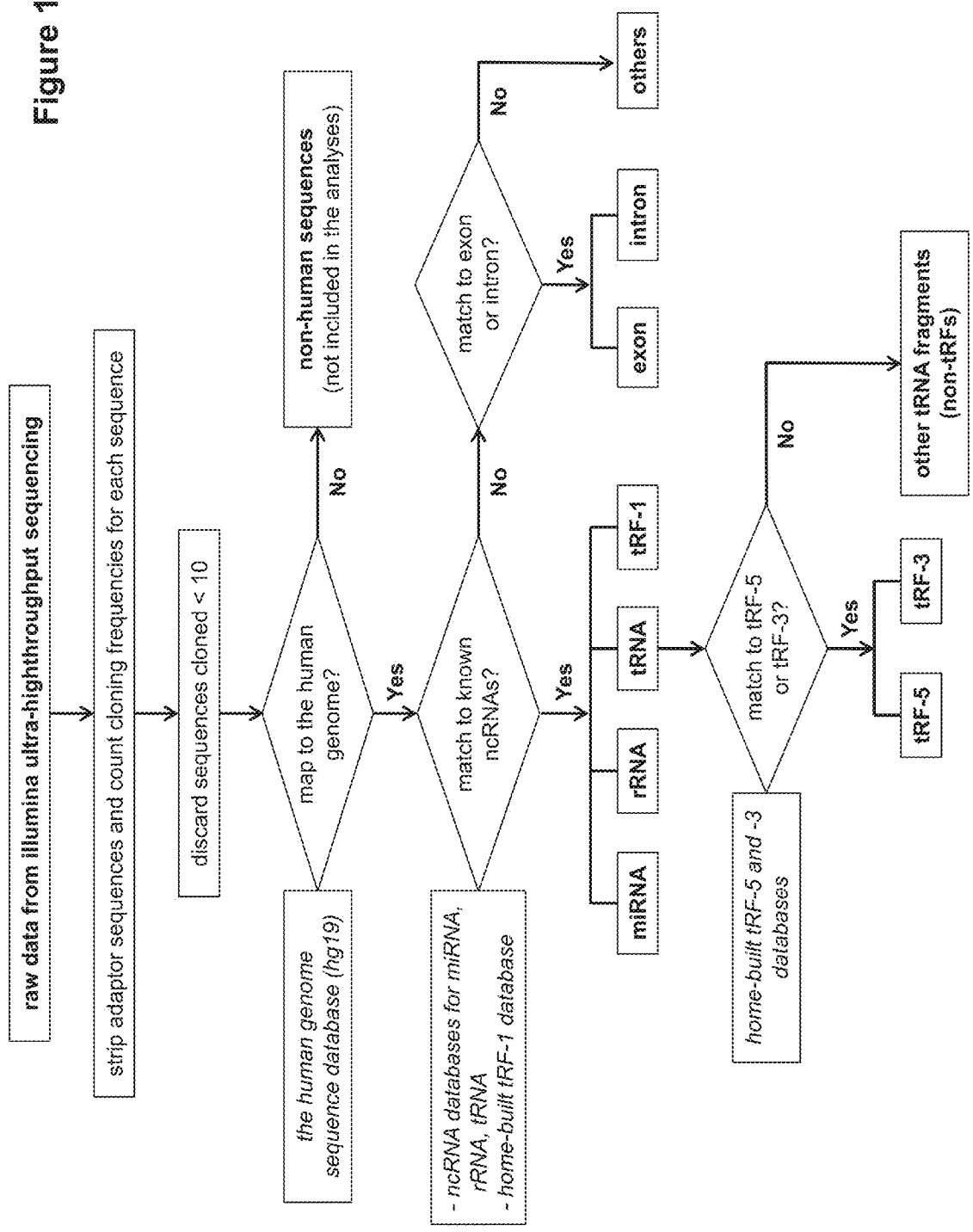
FIG. 1. Pipeline of analyses of Illumina high-throughput sequencing data. Flowchart of the sequencing data analyses is depicted. miRNA, microRNA; ncRNA, noncoding RNA; rRNA, ribosomal RNA; tRF, tRNA-derived RNA fragment; tRNA, transfer RNA.
Figure 8:
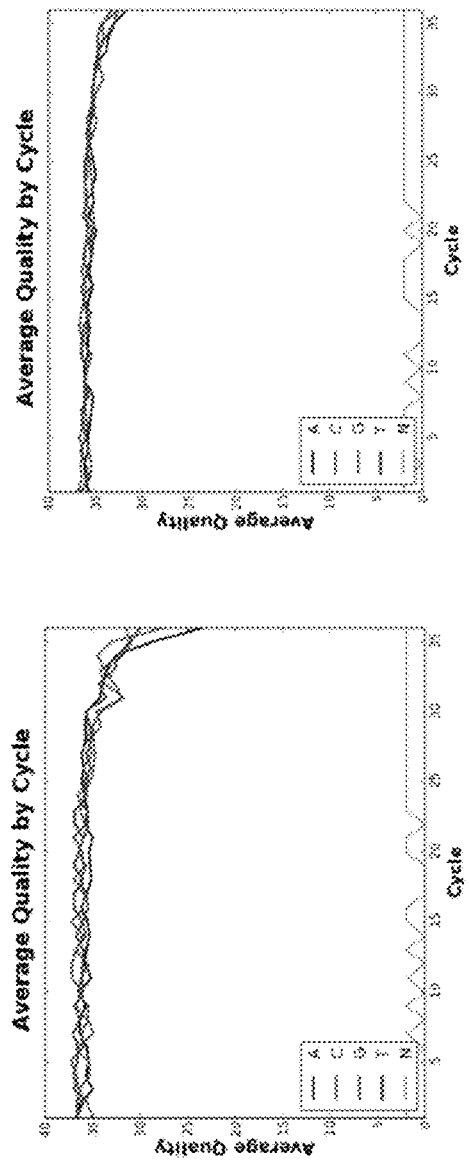
FIG. 8. The average sequencing quality score.

Global sncRNA profile in RSV-infected airway epithelial cells. To obtain a global sncRNA expression profile, small RNAs from mock- or RSV-infected A549 cells were subjected to Illumina ultra-high-throughput sequencing. A total of 32,332,590 sequence reads were generated without significant quality issues (FIG. 8). These raw data were further processed as depicted in FIG. 1. After adaptor sequences were stripped, individual sequences with cloning frequency (read numbers)≥10 were sorted by mapping them to different databases. In brief, the sequences were first mapped to the human genome (hg19, available through the world wide web at the UCSC Genome Browser, hgdownload.cse.ucsc.edu/downloads.html) to eliminate non-human sequences, such as those derived from RSV. The filtered human sncRNA sequences were classified by comparing them to the miRNA database (available through the world wide web at miRBase; www.mirbase.org), the rRNA database (available through the world wide web at RDP 10.28; rdp.cme.ms-u.edu/misc/rel10info.jsp), the tRNA database (available through the world wide web at GtRNAdb; gtrnadb.ucsc.edu/), and the Exon-Intron Database (available through the world wide web at EID; mcb.harvard.edu/gilbert/EID).

Figure 2:
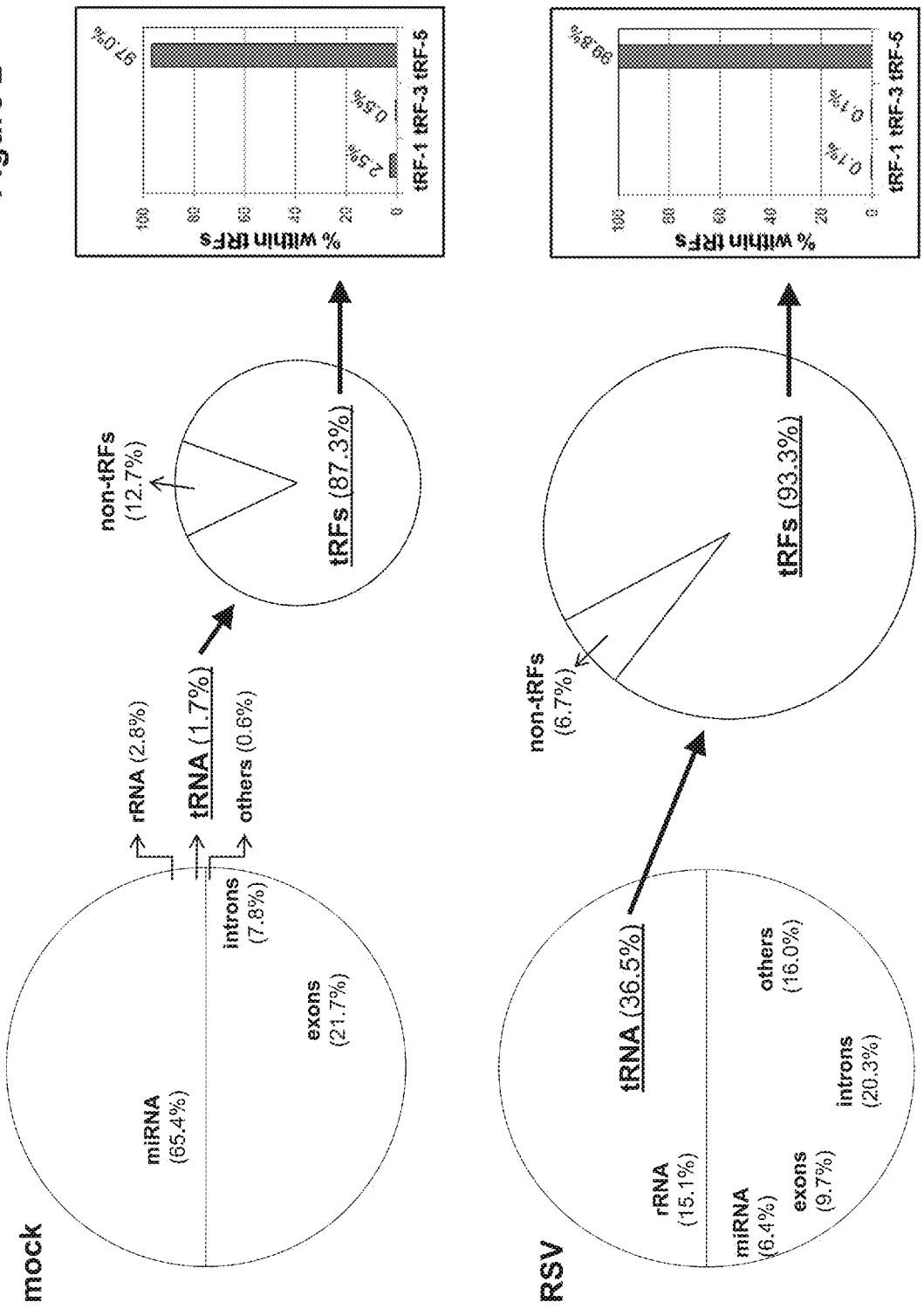
FIG. 2. Classification of sncRNAs. Human genome-derived sncRNAs were sorted according to their origins, and their relative abundance (calculated from read numbers) was depicted in pie charts (left two charts). tRNA-derived sncRNAs were divided into non-tRFs and tRFs (middle two charts). tRFs were further sorted into tRF-1, 3, and 5 series (bar graphs on the right). The definition of tRFs and the sub-types (-1, -3, and -5 series) is described in the text and depicted in FIG. 9. miRNA, microRNA; sncRNA, small noncoding RNA; rRNA, ribosomal RNA; RSV, respiratory syncytial virus; tRF, tRNA-derived RNA fragment; tRNA, transfer RNA.
Figure 3:
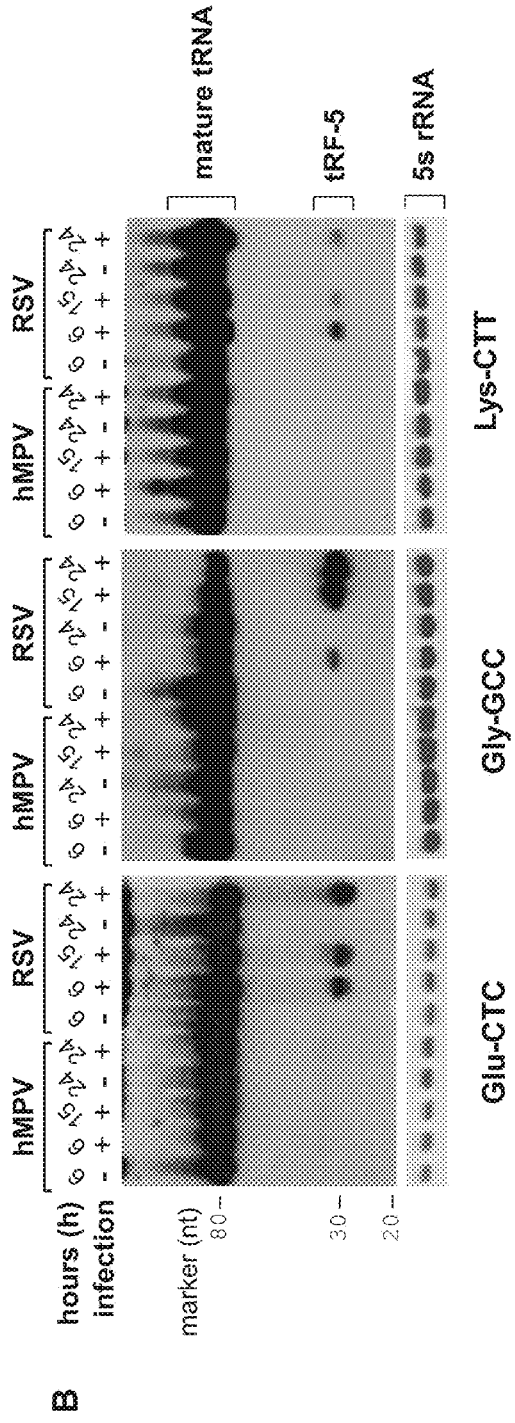
FIG. 3. Experimental validation and characterization of tRF-5s. A. Sequence alignment of tRF-5s with their parental mature tRNAs and Northern probes. The length of each sequence is indicated in parentheses. CCA sequence that is post-transcriptionally added to the 3'-end of tRNA is indicated in brackets. B. Total RNA from indicated treatments in A549 cells was loaded to a denaturing polyacrylamide gel for Northern hybridization using probes indicated in panel A. 5S rRNA is shown for equal loading. The positions of tRF-5 and mature tRNA are indicated on the right; molecular size markers are indicated on the left. The blot was exposed for ≤8 h. Data are representative of 2-3 independent experiments. C. Primary cultured SAE cells were mock- or RSV-infected at MOI of 3 for various lengths of time as indicated. All other experimental conditions were similar to those described at B in FIG. 3, except that 4 µg of total RNAs were used for Northern hybridization. D. A549 cells were transfected with purified viral RNAs (lane 2), or infected with naïve or UV-inactivated RSV for 24 h (lanes 4 and 6). Cells treated with Lipofectamine 2000 (lane 1) or mock-infected (lanes 3 and 5) were used as negative controls. Northern hybridization was done as described at B in FIG. 3. E. Total, nuclear, or cytoplasmic RNAs from mock- or RSV-infected A549 cells were subjected to Northern hybridization. All other descriptions are the same as B in FIG. 3. Data are representative of 2-3 independent experiments. EtBr, ethidium bromide; hMPV, human metapneumovirus; MOI, multiplicity of infection; nt, nucleotide; rRNA, ribosomal RNA; RSV, respiratory syncytial virus; SAE, small alveolar epithelial cell; tRF, tRNA-derived RNA fragment; tRNA, transfer RNA; UV, ultraviolet. tRNA-Glu-CTC, SEQ ID NO:84; tRF5-GluCTC, SEQ ID NO:6; Northern probe for tRNA-Glu-CTC and/or tRF5-GluCTC, SEQ ID NO:85; tRNA-Gly-GCC, SEQ ID NO:86; tRF-GlyGCC, SEQ ID NO:13; Northern probe for tRNA-Gly-GCC and/or tRF-GlyGCC; SEQ ID NO:87; tRNA-Lys-CTT, SEQ ID NO:88; tRF-LysCTT, SEQ ID NO:19; Northern probe for tRNA-Lys-CTT and/or tRF-LysCTT, SEQ ID NO:89.
Figure 3:
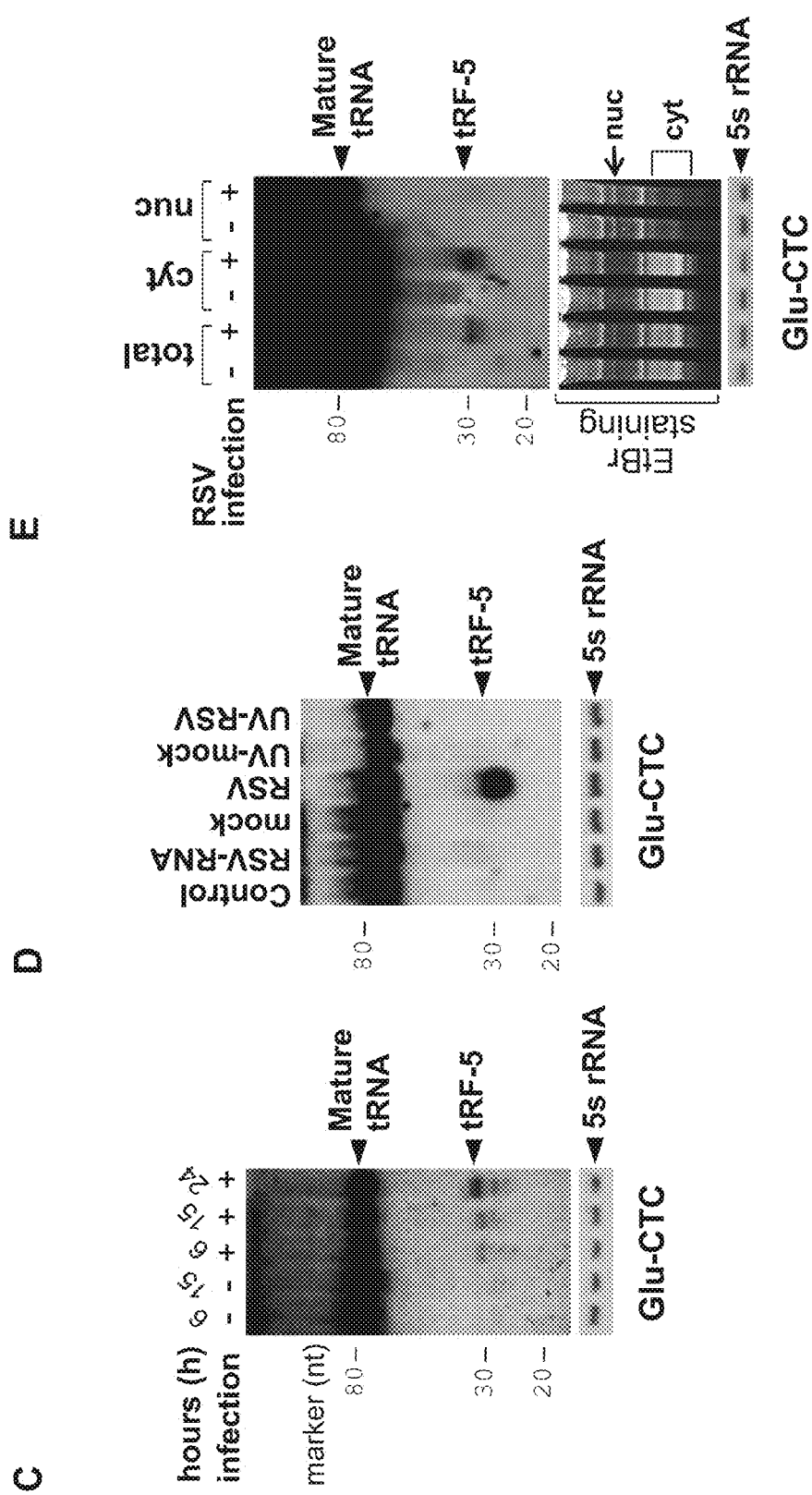

Most of sncRNAs were mapped to miRNAs, tRNAs, rRNAs, or mRNA transcripts, indicating the origin of these sncRNAs (FIG. 2). In high-throughput sequencing, the cloning frequency of a sncRNA provides a digital measure of its relative expression level. For fair comparison between mock- and RSV-infected samples, we calculated the relative sequencing frequency of each sncRNA by dividing its raw read numbers by the total read numbers of each experimental group. As shown in FIG. 2, a striking difference in sncRNA composition was observed between mock- and RSV-infected samples. In mock-infected cells (those without RSV infection), the majority of sncRNAs (65.4% of total reads) were miRNAs, while sncRNAs mapped to rRNA and tRNA only represented 2.8% and 1.7%, respectively. Following RSV infection, tRNA-derived sncRNAs became the most abundant sncRNAs (36.5% of total reads), while miRNAs were only 6.4%. Except for miRNAs that are processed from their short-lived precursors, other sncRNAs were likely derived from the cleavage of their parental stable RNAs (tRNA, rRNA, etc). However, this cleavage did not seem to be random, as the proportion of individual groups of sncRNA was not equally increased upon RSV infection, and no RNA quality issue was found, as evaluated by 5S rRNA Northern (FIG. 3B and other figures shown afterwards). Throughout this example, more evidence is provided that sncRNAs from tRNA are not by-products of random RNA degradation.

Figure 9:
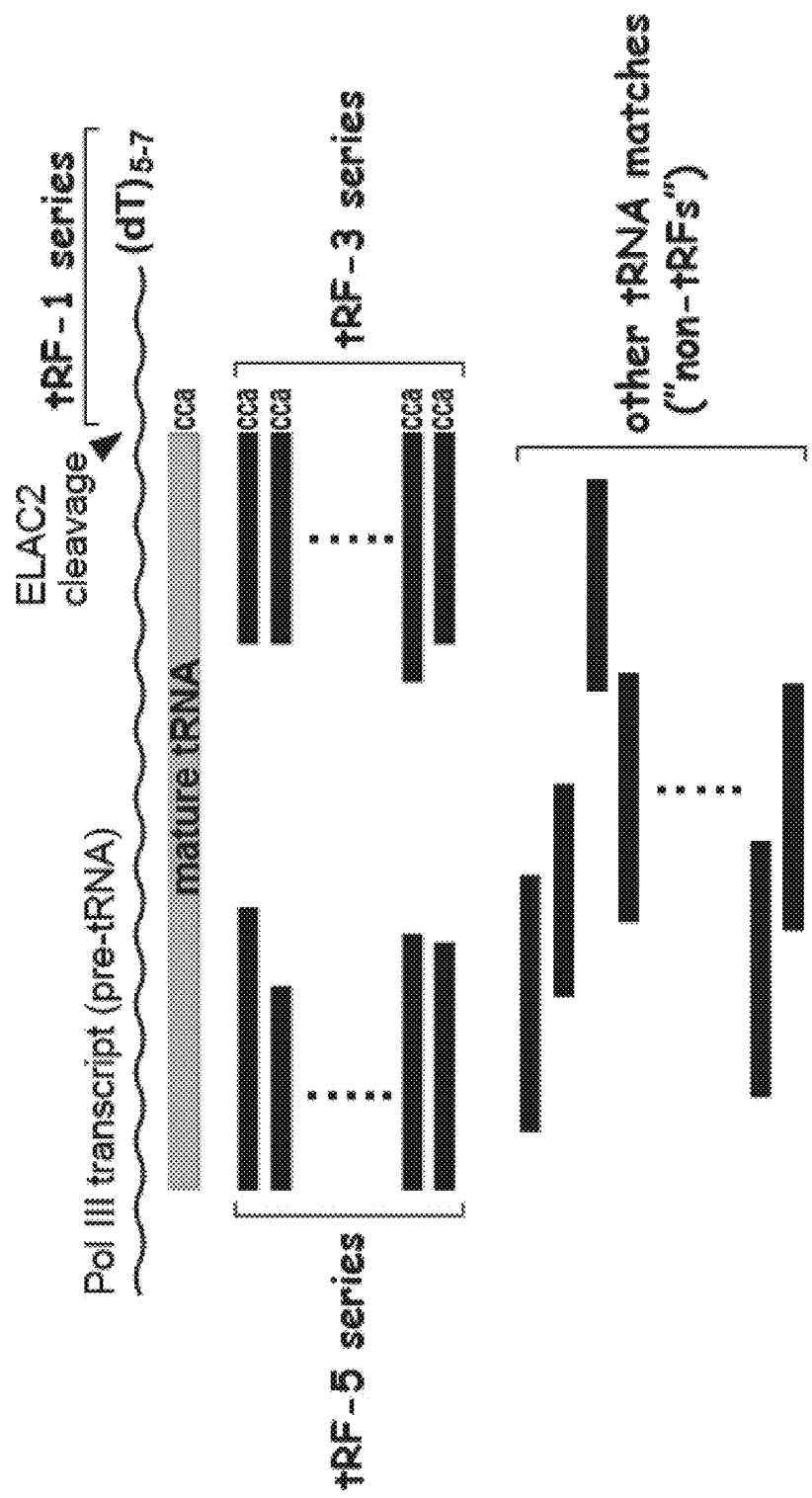
FIG. 9. Diagram of tRFs aligned at a tRNA locus (modified from ref 8).

The enrichment of tRNA-derived sncRNAs following RSV infection. As mentioned earlier, tRNA-derived sncRNAs are an emerging class of sncRNAs that play important biological functions (Emara et al., (2010) J Biol Chem 285:10959-10968, Yamasaki et al., (2009) J Cell Biol 185: 35-42, Lee et al., (2009) Genes Dev 23:2639-2649, Haussecker et al., (2010) RNA 16:673-695). Diverse tRNA-derived sncRNAs have been identified by several research groups, but a consensus nomenclature has not been finalized. Collectively from the literature, two classifications which are not exclusive of each other have been proposed. One is based on their relative location in tRNA (illustrated in FIG. 9). For those whose sequence precisely matches to the 5'- or 3'-end of mature or precursor tRNAs, they are classified into tRNA-derived RNA Fragments (tRFs). All others are grouped as non-tRFs. Further grouping defines tRF-5 and -3 series depending on which side they are located in the mature tRNA. Another subgroup is the tRF-1 series which corresponds to the 3'-trailer sequences cleaved off from precursor tRNAs during tRNA maturation (Lee et al., (2009) Genes Dev 23:2639-2649). The other classification is based on their sizes—long tRNA-derived sncRNAs of 30-40 nts (termed as "tRNA halves") versus small ones shorter than 30 nts (Emara et al., (2010) J Biol Chem 285:10959-10968, Yamasaki et al., (2009) J Cell Biol 185:35-42, Fujishima et al., (2008) PLoS ONE 3:e1622). So far, tRNA halves are known to be induced by cellular stresses and have gained significant attention. They are generated by a single cleavage by an endonuclease from mature tRNA, thus are tRFs.

We prefer the "tRF" nomenclature as this classification is more informative (Lee et al., (2009) Genes Dev 23:2639-2649). Accordingly, we sorted tRNA-derived sncRNAs by mapping them to our previously built tRF-5, -3 and -1 database (Lee et al., (2009) Genes Dev 23:2639-2649). As shown in FIG. 2, tRFs were dominant over non-tRFs, both in mock- and RSV-infected cells. Notably, the fraction of tRFs increased, while that of non-tRFs significantly decreased (from 12.7% to 6.7%) upon RSV infection. This tendency also argues against the possibility that the induction of tRFs by RSV infection was caused by random RNA degradation. Among tRFs, most of them belonged to the tRF-5 series whereas tRF-3 and -1 series were scarce (FIG. 2). Following RSV infection, tRF-5s with a cloned frequency≥1/% (1 per 1,000) are presented in Table 1, and rest of tRF-5s are listed in Table 2.

TABLE 1

Summary of tRF-5 series with a relative cloning frequency ≥1% (reads per mil) in RSV-infected sample. Listed as SEQ ID NO: 1 through SEQ ID NO: 27.

| | | Relative sequencing frequency (% of total sequencing reads) | | SEQ ID NO: |
|---|---|---|---|---|
| | | Mock | RSV | |
| GGGGGTATAGCTCAGGGGTAGAGCATTTG | CysGCA | 0.030 | 36.360 | 1 |
| GGTTCCATGGTGTAATGGTTAGCACTCTGGA | GlnCTG-1 | 0.060 | 11.130 | 2 |
| GGTTCCATGGTGTAATGGTAAGCACTCTG | GlnCTG-2 | 0.004 | 1.440 | 3 |
| GGTTCCATCGTGTAATGGTGAGCACTCTG | GlnCTG-3 | 0.003 | 1.120 | 4 |
| GGTCCCGTGGTGTAATGGTTAGCACTCTGG | GlnTTG | 0.030 | 2.540 | 5 |
| TCCCTGGTGGTCTAGTGGTTAGGATTCGGCG | GluCTC-1$^a$ | 0.122 | 51.900 | 6 |
| TCCCTGTGGTCTAGTGGTTAGGATTCGGCG | GluCTC-2 | 0.050 | 18.250 | 7 |
| TCCCTGGTGGTCTAGTGGCTAGGATTCGGCG | GluTTC-1 | 0.012 | 6.350 | 8 |
| TCCCACATGGTCTAGCGGTTAGGATTCCTG | GluTTC-2 | 0.021 | 2.910 | 9 |
| TCCCATATGGTCTAGCGGTTAGGATTCCTGG | GluTTC-3 | 0.006 | 2.200 | 10 |
| GCATGGGTGGTTCAGTGGTAGAATTCTCG | GlyGCC-1$^a$ | 2.090 | 105.700 | 11 |
| GCGCCGCTGGTGTAGTGGTATCATGCAAG | GlyCCC | 0.350 | 90.600 | 12 |
| GCATTGGTGGTTCAGTGGTAGAATTCTCG | GlyGCC-3 | 0.507 | 30.800 | 13 |
| GCATTGGTGGTTCAGTGGGAGAATTCTCG | GlyGCC-4 | <0.0005 | 3.970 | 14 |
| GCGTTGGTGGTATAGTGGTGAGCATAGCTG | GlyTCC-1 | 0.015 | 3.356 | 15 |
| GCGTTGGTGGTATAGTGGTGAGAATAGCT | GlyTCC-2 | 0.005 | 1.230 | 16 |
| GCCGTGATCGTATAGTGGTTAGTACTCTGCG | HisGTG-1 | 0.006 | 1.100 | 17 |
| GTTAAGATGGCAGAGCCCGGTAATCGCATAA | LeuTAA | 0.100 | 2.530 | 18 |
| GCCCGGCTAGCTCAGTCGGTAGAGCATGAG | LysCTT-1$^a$ | 0.037 | 14.100 | 19 |
| GCCCGGCTAGCTCAGTCGGTAGAGCATGGGA | LysCTT-2 | 0.008 | 2.200 | 20 |
| GCCCGGCTAGCTCAGTCAGTAGAGCATGGG | LysCTT-3 | 0.000 | 1.060 | 21 |
| GCCCGGATAGCTCAGTCGGTAGAGCATCAG | LysTTT | 0.090 | 3.110 | 22 |
| AGCAGAGTGGCGCAGCGGAAGCGTGCTG | MetCAT-1 | 0.003 | 3.780 | 23 |

TABLE 1-continued

Summary of tRF-5 series with a relative cloning frequency ≥1% (reads per mil) in RSV-infected sample. Listed as SEQ ID NO: 1 through SEQ ID NO: 27.

| Sequence | Origin | Relative sequencing frequency (% of total sequencing reads) Mock | RSV | SEQ ID NO: |
|---|---|---|---|---|
| GCCGAAATAGCTCAGTTGGGAGAGCTTTAGA | PheGAA | <0.0005 | 1.590 | 24 |
| GACGAGGTGGCCGAGTGGTTAAGGCAATGG | SerGCT-1 | 0.004 | 1.123 | 25 |
| GTTTCCGTAGTGTAGTGGTCATCACGTTC | ValAAC-1 | 0.010 | 2.810 | 26 |
| GTTTCCGTAGTGTAGTGGTTATCACATTC | ValCAC | 0.020 | 1.170 | 27 |

The relative cloning frequency of a tRF was calculated by dividing its read number by the total read number of each experimental group. tRFs were sorted by an alphabetical order of parental tRNA isoforms. For tRNA isoforms sharing same anticodon, they were sequentially numbered according to the abundance of tRF-5s in the RSV-infected sample.
[a] tRFs whose expression was confirmed by norhtern blot.

TABLE 2

Summary of all tRF-5 series (SEQ ID NOs: 1-72).

| Sequence | SEQ ID NO: | Origin | Relative sequencing frequency (% of total sequencing reads) Mock | RSV |
|---|---|---|---|---|
| GGGGGATTAGCTCAAATGGTAGAGCCCTC | 28 | AlaAGC-1 | <0.0005 | 0.634 |
| GGGGGATTAGCTCAAATGGTAGAGCTCTC | 29 | AlaAGC-2 | 0.002 | 0.450 |
| GGGGGTGTAGCTCAGTGGTAGAGCGCATG | 30 | AlaTGC | <0.0005 | 0.241 |
| GGGCCAGTGGCGCAATGGATAACGCCTCT | 31 | ArgACG | <0.0005 | 0.090 |
| GACCCAGTGGCCTAATGGATAAGGCATCAG | 32 | ArgCCG | 0.005 | 0.250 |
| GCCCCAGTGGCCTAATGGATAAGGCACTGCCT | 33 | ArgCCT | 0.002 | 0.110 |
| GACCGCGTGGCCTAATGGATAAGGCTTCTG | 34 | ArgTCG | 0.001 | 0.080 |
| GGCTCCGTGGCGCAATGGATAGCGCATTG | 35 | ArgTCT-1 | <0.0005 | 0.540 |
| GGCTCTGTGGCGCAATGGATAGCGCATTG | 36 | ArgTCT-2 | 0.001 | 0.408 |
| GGCTCTCTGGCGCAATGGATAGCGCATTG | 37 | ArgTCT-3 | <0.0005 | 0.188 |
| GGATCTGTGGCGCAATGGATAGCGCATTG | 38 | ArgTCT-4 | <0.0005 | 0.116 |
| GGCTCTGTAGCGCAATGGATAGCGCATTGG | 39 | ArgTCT-5 | <0.0005 | 0.073 |
| GTCTCTGTGGCGCAATCGGTTAGCGCTTTCG | 40 | AsnGTT | 0.005 | 0.020 |
| TCCTCGTTCGTATAGTGGTGAGTATCCCCG | 41 | AspGTC-1 | 0.006 | 0.940 |
| TCCTCTTTTGTATAGTGGTGAGTATCCCCGC | 42 | AspGTC-2 | 0.001 | 0.163 |
| GGGGGTATAGCTCAGGGGTAGAGCATTTG | 1 | CysGCA | 0.030 | 36.360 |
| GGTTCCATGGTGTAATGGTTAGCACTCTGGA | 2 | GlnCTG-1* | 0.060 | 11.130 |
| GGTTCCATGGTGTAATGGTAAGCACTCTG | 3 | GlnCTG-2 | 0.004 | 1.440 |
| GGTTCCATCGTGTAATGGTGAGCACTCTG | 4 | GlnCTG-3 | 0.003 | 1.120 |
| GGTTCCATCGTGTAATGGTTAGCACTCTGGA | 43 | GlnCTG-4 | 0.006 | 0.185 |

TABLE 2-continued

Summary of all tRF-5 series (SEQ ID NOs: 1-72).

| Sequence | SEQ ID NO: | Origin | Relative sequencing frequency (% of total sequencing reads) Mock | RSV |
|---|---|---|---|---|
| GGTTCCATGGTGTAACGGTTAGCACTCTGGA | 44 | GlnCTG-5 | <0.0005 | 0.170 |
| GGTTCCATTGTGTAATGGTAAGCACTCTGGA | 45 | GlnCTG-6 | 0.004 | 0.138 |
| GGTTCCATGTGTAATGGTTAGCACTCTGG | 46 | GlnCTG-7 | 0.003 | 0.109 |
| GGTCCCGTGGTGTAATGGTTAGCACTCTGG | 5 | GlnTTG | 0.030 | 2.540 |
| TCCCTGGTGGTCTAGTGGTTAGGATTCGGCG | 6 | GluCTC-1* | 0.122 | 51.900 |
| TCCCTGTGGTCTAGTGGTTAGGATTCGGCG | 7 | GluCTC-2 | 0.050 | 18.250 |
| TCCCTGGTGGTCTAGTGGCTAGGATTCGGCG | 8 | GluTTC-1 | 0.012 | 6.350 |
| TCCCACATGGTCTAGCGGTTAGGATTCCTG | 9 | GluTTC-2 | 0.021 | 2.910 |
| TCCCATATGGTCTAGCGGTTAGGATTCCTGG | 10 | GluTTC-3 | 0.006 | 2.200 |
| TCCCTGTGGTCTAGTGGCTAGGATTCGGCG | 47 | GluTTC-4 | 0.007 | 0.830 |
| GCATGGGTGGTTCAGTGGTAGAATTCTCG | 11 | GlyGCC-1* | 2.090 | 105.700 |
| GCGCCGCTGGTGTAGTGGTATCATGCAAG | 12 | GlyCCC | 0.350 | 90.600 |
| GCATTGGTGGTTCAGTGGTAGAATTCTCG | 13 | GlyGCC-3 | 0.507 | 30.800 |
| GCATTGGTGGTTCAGTGGGAGAATTCTCG | 14 | GlyGCC-4 | <0.0005 | 3.970 |
| GCGTTGGTGGTATAGTGGTGAGCATAGCTG | 15 | GlyTCC-1 | 0.015 | 3.356 |
| GCGTTGGTGGTATAGTGGTGAGAATAGCT | 16 | GlyTCC-2 | 0.005 | 1.230 |
| GCCGTGATCGTATAGTGGTTAGTACTCTGCG | 17 | HisGTG-1 | 0.006 | 1.100 |
| GCCGTAATCGTATAGTGGTTAGTACTCTGCG | 48 | HisGTG-2 | <0.0005 | 0.230 |
| GCTCCAGTGGCGCAATCGGTTAGCGCGCGG | 49 | IleTAT | <0.0005 | 0.010 |
| GGCCGGTTAGCTCAGTTGGAAGAGCGTGGTG | 50 | IleGAT | <0.0005 | 0.010 |
| GGTAGCGTGGCCGAGCGGTCTAAGGCCTGG | 51 | LeuAAG-1 | <0.0005 | 0.392 |
| GGTAGCGTGGCCGAGCGGTCTAAGGCTCTGG | 52 | LeuAAG-2 | 0.001 | 0.245 |
| GGTAGCGTGGCCGAGCGGTCTAAGGCGCTGG | 53 | LeuAAG-3 | 0.001 | 0.239 |
| GTCAGGATGGCCGAGTGGTCTAAGGCCCAGA | 54 | LeuCAA-1 | 0.006 | 0.695 |
| GTCAGGATGGCCGAGTGGTCTAAGGCGCCAG | 55 | LeuCAA-2 | 0.001 | 0.086 |
| GTCAGGATGGCCGAGCGGTCTAAGGCGCTGC | 56 | LeuCAG | 0.050 | 0.200 |
| GTTAAGATGGCAGAGCCCGGTAATCGCATAA | 18 | LeuTAA | 0.100 | 2.530 |
| GGTAGTGTGGCCGAGCGGTCTAAGGCCTGG | 57 | LeuTAG | 0.003 | 0.550 |
| GCCCGGCTAGCTCAGTCGGTAGAGCATGAG | 19 | LysCTT-1* | 0.037 | 14.100 |
| GCCCGGCTAGCTCAGTCGGTAGAGCATGGGA | 20 | LysCTT-2 | 0.008 | 2.200 |
| GCCCGGCTAGCTCAGTCAGTAGAGCATGGG | 21 | LysCTT-3 | 0.000 | 1.060 |
| GCCCGGATAGCTCAGTCGGTAGAGCATCAG | 22 | LysTTT | 0.090 | 3.110 |
| AGCAGAGTGGCGCAGCGGAAGCGTGCTG | 23 | MetCAT-1 | 0.003 | 3.780 |
| AGCAGAGGGGCGCAGCGGAAGCGTGCTG | 58 | MetCAT-2 | <0.0005 | 0.510 |

TABLE 2-continued

Summary of all tRF-5 series (SEQ ID NOs: 1-72).

| Sequence | SEQ ID NO: | Origin | Relative sequencing frequency (% of total sequencing reads) | |
|---|---|---|---|---|
| | | | Mock | RSV |
| AGCAGAGTGGCGCAGTGGAAGCGTGCTG | 59 | MetCAT-3 | <0.0005 | 0.470 |
| GCCGAAATAGCTCAGTTGGGAGAGCTTTAGA | 24 | PheGAA | <0.0005 | 1.590 |
| GGCTCGTTGGTCTAGGGGTATGATTCTCG | 60 | ProAGG | <0.0005 | 0.050 |
| GGCTCGTTAGTCTAGGGGTATGATTCTCGCTTC | 61 | ProCGG | 0.001 | 0.000 |
| GGCTCGTTGGTCTAGTGGTATGATTCTCG | 62 | ProTGG | 0.007 | 0.460 |
| GTAGTCGTGGCCGAGTGGTTAAGGCTATGG | 63 | SerAGA | 0.007 | 0.460 |
| GCTGTGATGGCCGAGTGGTTAAGGCTTTGA | 64 | SerCGA | 0.001 | 0.160 |
| GACGAGGTGGCCGAGTGGTTAAGGCAATGG | 25 | SerGCT-1 | 0.004 | 1.123 |
| GACGAGGTGGCCGAGTGGTTAAGGCTATGG | 65 | SerGCT-2 | 0.004 | 0.809 |
| GACGAGGTGGCCGAGTGGTTAAGGCGATGG | 66 | SerGCT-3 | 0.001 | 0.246 |
| GCAGCGATGGCCGAGTGGTTAAGGCTTTG | 67 | SerTGA | 0.002 | 0.030 |
| GGCGCCGTGGCTTAGTTGGTTAAAACTCCTG | 68 | ThrAGT | 0.001 | 0.130 |
| GGCGCGGTGGCCAAGTGGTAAGGCTTCGG | 69 | ThrCGT | 0.002 | 0.060 |
| CCTTCAATAGATCAGCTGGTAGAGC | 70 | TyrATA | <0.0005 | <0.0005 |
| GTTTCCGTAGTGTAGTGGTCATCACGTTC | 26 | ValAAC-1 | 0.010 | 2.810 |
| GGGGGTGTAGCTCAGTGGTAGAGCGT | 71 | ValAAC-2 | <0.0005 | 0.517 |
| GTTTCCGTAGTGTAGTGGTTATCACATTC | 27 | ValCAC | 0.020 | 1.170 |
| GTTTCCGTGGTGTAGTGGTTATCACATTC | 72 | ValTAC | 0.070 | 0.520 |

Expression validation of tRFs by Northern blot. We confirmed our sequencing data by using Northern hybridization which is the most suitable method to validate a newly identified sncRNA. It does not involve any enzymatic treatment and thus visualizes a sncRNA band at its raw size. We chose three tRF-5s that were abundantly cloned after RSV infection (Table 1 and FIG. 3A). They were derived from tRNA-Glu-CTC, -Gly-GCC, and -Lys-CTT, and thus henceforth named tRF5-GluCTC, tRF5-GlyGCC, and tRF5-LysCTT, respectively.

A band of ~30 nts was readily detectable (FIG. 3B), together with a band at ~80 nt representing the corresponding mature tRNA from which each tRF was likely derived. The tRF bands were clearly discrete and prominent along the lane, indicating a specific cleavage event during RSV infection. Most importantly, tRFs of ~30 nts were detected exclusively in the RSV-infected sample. Despite tRNA cleavage, the mature tRNAs were not significantly depleted and their bands kept intense among samples.

Figure 10:
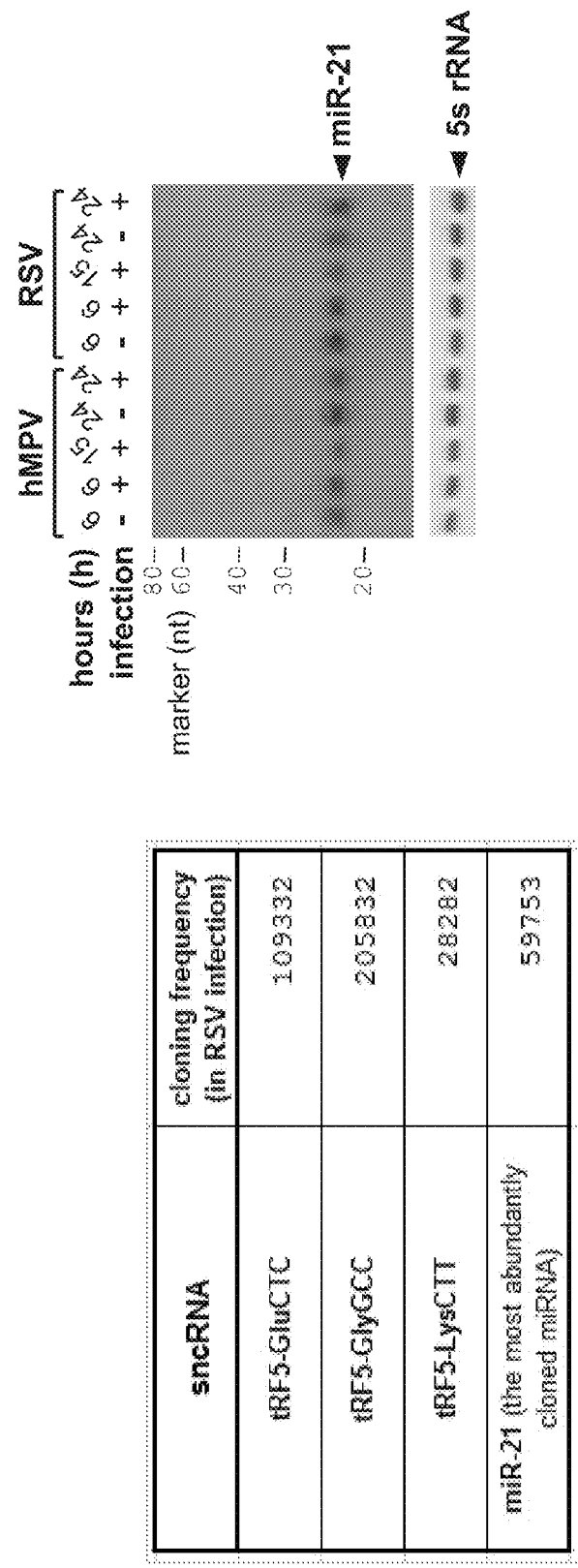
FIG. 10. Northern hybridization of miR-21.

Although the band intensity indicated that the tRF-5s were generally much less in quantity than the mature tRNAs, the expression levels of the tRF-5s after RSV infection seemed to be higher than that of the most abundant miRNA, miR-21, based on their cloning frequencies (FIG. 10A) and the signal intensity in Northern hybridization under a similar condition (FIG. 10B).

Our data also revealed that the induction of tRF-5s was virus specific. Unlike RSV infection, the infection with human metapneumovirus (hMPV), also a pneumovirus of the Paramyxoviridae family, failed to induce tRF5-GluCTC, tRF5-GlyGCC and tRF5-LysCTT (FIG. 3B), further suggesting that tRFs are not random degradation by-products. It is unlikely that the lack of tRF induction by hMPV was due to inefficient hMPV infection, as we and others have demonstrated that A549 cells are permissive to both hMPV and RSV infection, and infected cells exhibit some similar responses including enhanced surface expression of major histocompatibility complex-I (MHC-I) (Garofalo et al., (1994) Am J Respir Crit Care Med 149:A987, Ren et al., (2011) PLoS ONE 6:e24496). Collectively, our data indicated that RSV infection induced specific cleavage of tRNA, generating abundant amount of tRF-5s.

Characterization of tRF-5 from tRNA-Glu-CTC. tRF5-GluCTC was chosen for further study, as it was one of the most abundantly cloned tRF-5s (Table 1) and clearly detected by Northern hybridization (FIG. 3B). We also confirmed that tRF5-GluCTC was inducible by RSV in primary small alveolar epithelial cells (SAE) (FIG. 3C). This observation was in agreement with previous results showing A549 cells as a suitable cell model for investigating the responses of airway epithelial cells to viral infection (Bao et al., (2007) Virology 368:91-101, Zhang et al., (2001) J Virol 75:9044-9058).

To test whether the induction of tRF5-GluCTC is dependent upon RSV replication, A549 cells were transfected with purified RSV RNA, or infected with live or UV-inactivated RSV. Untreated- or mock-infected cells were used as controls. Compared to live RSV, neither purified RNA nor UV-inactivated virus induced tRF5-GluCTC (FIG. 3D), suggesting that its induction requires viral replication.

We also determined the sub-cellular localization of tRF5-GluCTC. Our nuclear/cytoplasmic fractionation indicated that tRF5-GluCTC existed exclusively in the cytoplasm (FIG. 3E). The quality of fractionation was assured by Western blot of lamin B as a nuclear marker [data not shown and Lee et al., (2009) Genes Dev 23:2639-2649, Bao et al., (2008) PLoS Pathog 4:e1000077] and ethidium bromide (EtBr) staining of fractionated RNAs. The cytoplasmic RNA was not contaminated by the nuclear RNA and vice versa, as indicated by EtBr-stained bands that were exclusively present in each of the two fractions (designated by arrow and bracket in the bottom panel of FIG. 3E).

The molecular function of tRF5-GluCTC. So far, we have demonstrated the specific induction of tRF5-GluCTC (and other tRF-5s) upon RSV infection. A more important question is whether it represents a biologically functional molecule. Given its cytoplasmic localization (FIG. 3E), one possibility is that tRF5-GluCTC incorporates into the siRNA/miRNA pathway. It was recently reported that a subset of tRFs exhibit miRNA/siRNA-like trans-silencing capacity (Haussecker et al., (2010) RNA 16:673-695).

To test this possibility, we performed an siRNA/miRNA assay using a sensor plasmid harboring a reverse complementary sequence of tRF5-GluCTC in the 3'UTR of the firefly luciferase gene (Pp) (FIG. 4A). If tRF5-GluCTC acts like an siRNA/miRNA, it would recognize the complementary sequence as a target site, therefore leading to suppressed expression of Pp (Lee et al., (2004) Cell 117:69-81). We transfected cells with a cognate sensor plasmid (designated as "Pp-anti_GluCTC_WT") or a control sensor plasmid lacking the target site (designated as "Pp-vector"), together with a plasmid expressing renilla luciferase (Rr) for normalization. The relative luciferase activity (Pp/Rr values; y-axis in FIG. 4B) was calculated and compared between treatments.

Compared to mock-infection, RSV infection significantly decreased the relative luciferase activity of "Pp-anti_GluCTC_WT" but did not affect that of "Pp-vector" (left two bars versus middle two bars in FIG. 4B), suggesting that RSV-induced tRF5-GluCTC could have a trans-silencing activity like miRNA/siRNA. Because RSV infection could lead to pleiotropic effects on the infected cells, we wanted to determine that the observed decrease of luciferase activity was tRF5-GluCTC specific. We inhibited tRF5-GluCTC by transfecting cells with 20-nt antisense oligonucleotides (see FIG. 4A for its sequence) which contained a backbone phosphorothioate and five nts on each end substituted with 2'-O-methyl ribonucleotides, as described (Yoo et al., (2004) Nucleic Acids Res 32:2008-2016, Ideue et al., (2009) RNA 15:1578-1587). Compared to a non-targeting control oligoribonucleotide (designated as "anti-control"), transfection of anti-GluCTC efficiently blocked RSV-induced tRF5-GluCTC (FIG. 4C) and accordingly restored the luciferase activity that was decreased by RSV infection (right two bars versus middle two bars in FIG. 4B).

Next, we dissected functional domains of tRF-GluCTC for its trans-silencing capacity, by introducing 3-4 nt mutations at the 3'-, middle-, or 5'-region of the tRF-GluCTC target site in the sensor plasmid "Pp-anti_GluCTC" as depicted in FIG. 4A. Contrary to Pp-anti_GluCTC_WT or the other two mutants, the luciferase activity of "Pp-anti_GluCTC_Mut3" ("Mut3" in FIG. 4D) was completely unresponsive to RSV infection, indicating that the 3'-portion of tRF-GluCTC was critical for its trans-silencing activity. The major targeting domain of tRF-GluCTC was different from that of miRNA/siRNA whose 5'-portion (called "seed sequence") is known to be important for target recognition (Esteller, (2011) Nat Rev Genet 12:861-874). Thus, the trans-silencing mechanism used by this tRF was distinct from that of canonical miRNA/siRNA.

We also attempted the ectopic expression of tRF5-GluCTC, by designing a synthetic oligoribonucleotide (designated as "tRF5-GluCTC-mimic" in FIG. 4A). Since our data shown in FIG. 4D demonstrated that tRF5-GluCTC was distinct from canonical miRNA/siRNA and its 3'-portion of was critical, we designed a duplex of 20 nts encompassing the 3'- and middle-region of tRF5-GluCTC. The mimic was designed as a duplex form to extend its stability. However, it lacked 2 nt overhangs, the signature end structure of miRNA/siRNA. Upon transfection of this mimic into A549 cells, the luciferase activity of "Pp-anti_GluCTC_WT", which was normalized by that of "Pp-anti_GluCTC_Mut3", was significantly suppressed by "tRF5-GluCTC-mimic" in a dose-dependent manner (FIG. 4E). In summary, our data demonstrated that tRF5-GluCTC suppressed target gene expression, through a mechanism distinct from miRNA/siRNA.

tRF5-GluCTC's role in controlling RSV replication. Is there a biological role for tRFs? As we developed methods to suppress or ectopically express tRF5-GluCTC, we could assess cellular phenotype after manipulating this tRF. First we examined its effect on RSV replication using microplaque immunoperoxidase detection assays to compare the yield of infectious viral particles produced by the cells, which were transfected with anti-control- or anti-GluCTC. As shown in FIG. 5A, suppression of tRF5-GluCTC led to decreased RSV yield. Two additional experiments, real-time PCR assays for viral gene transcription (FIG. 5B) and Western blot for viral protein expression (FIG. 5C), also supported the result of FIG. 5A.

Figure 5:
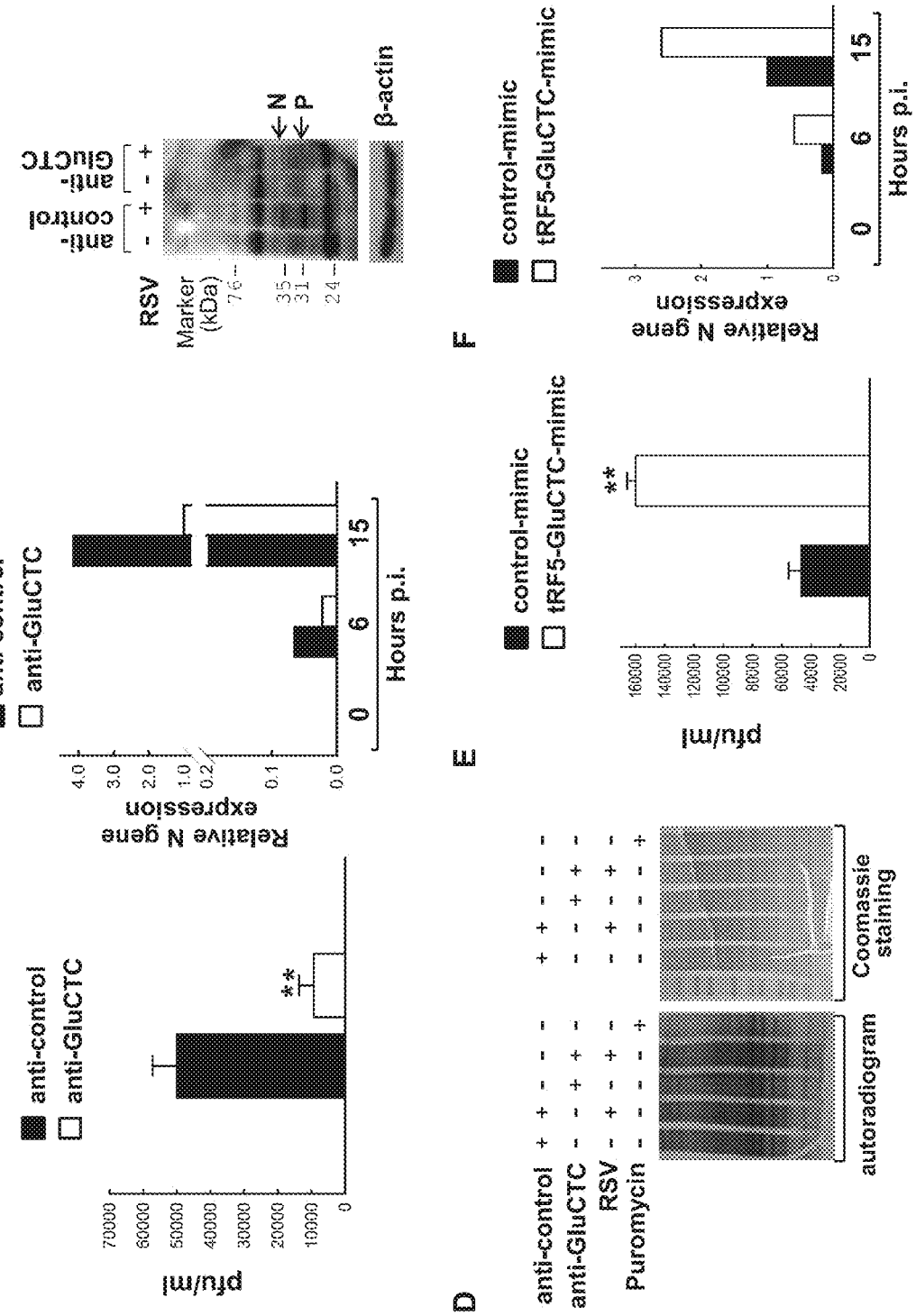
FIG. 5. tRF5-GluCTC promotes RSV replication. A-D. Knockdown of tRF5-GluCTC inhibits RSV replication. Anti-sense oligos transfection and RSV infection were performed as described at B in FIG. 4. At 15 h p.i. (panels A and C) or indicated times p.i. (panel B), viral infectious particles were measured by immunostaining (panel A). Viral gene transcription and protein synthesis were investigated by real time PCR (panel B) and Western blot (panel C) respectively. The total protein synthesis was also assayed for the groups as indicated (panel D). E-F. A549 cells were transfected with 50 nM of indicated mimic oligos. After 6 h post-transfection, cells were mock- or RSV-infected. At 15 h p.i., viral titration and viral gene expression were assayed, respectively. Data are a representative of 2-3 independent experiments. **P<0.01, relative to the black bar. pfu, plaque-forming unit; p.i., post-infection; RSV, respiratory syncytial virus; tRF, tRNA-derived RNA fragment; tRNA, transfer RNA.
Figure 11:
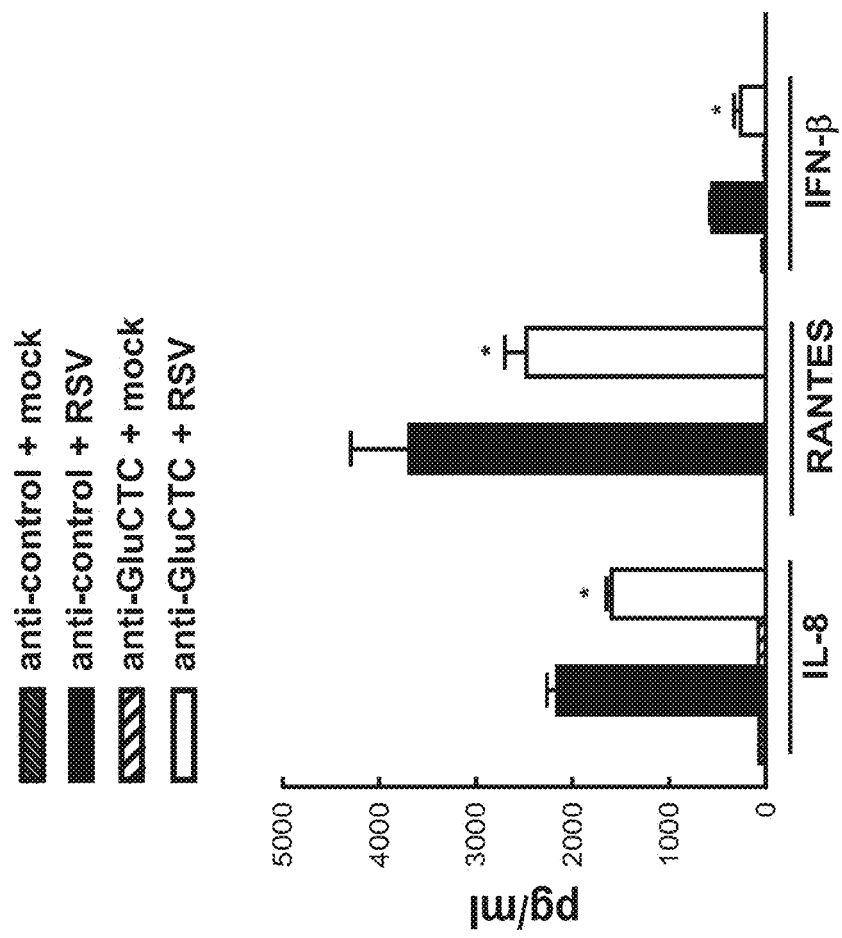
FIG. 11. Effect of tRF5-GluCTC on cytokine and chemokine secretion.

Previously, it has been shown that the induction of chemokines and cytokines by RSV infection is viral replication dependent (Haeberle et al., (2001) J Virol 75:878-890). In agreement with the data of FIG. 5, the induction of IL-8, RANTES and IFN-β by RSV was significantly decreased, when tRF5-GluCTC was inhibited by anti-GluCTC (FIG. 11). This result might have been due to side-effects of anti-GluCTC, for instance, possibly targeting the mature tRNA and thereby interfering with cellular global protein synthesis. This possibility was ruled out as we found that global protein synthesis was not affected upon transfection of anti-GluCTC. To validate our assay, we treated cells with puromycin, a known inhibitor for protein synthesis, as a control and observed the inhibition of protein synthesis as expected (FIG. 5D, lane 5). Conversely, overexpression of tRF5-GluCTC-mimic significantly enhanced RSV replication, further confirming the stimulatory role of tRF5-GluCTC in RSV replication (FIGS. 5E and F)

Figure 12:
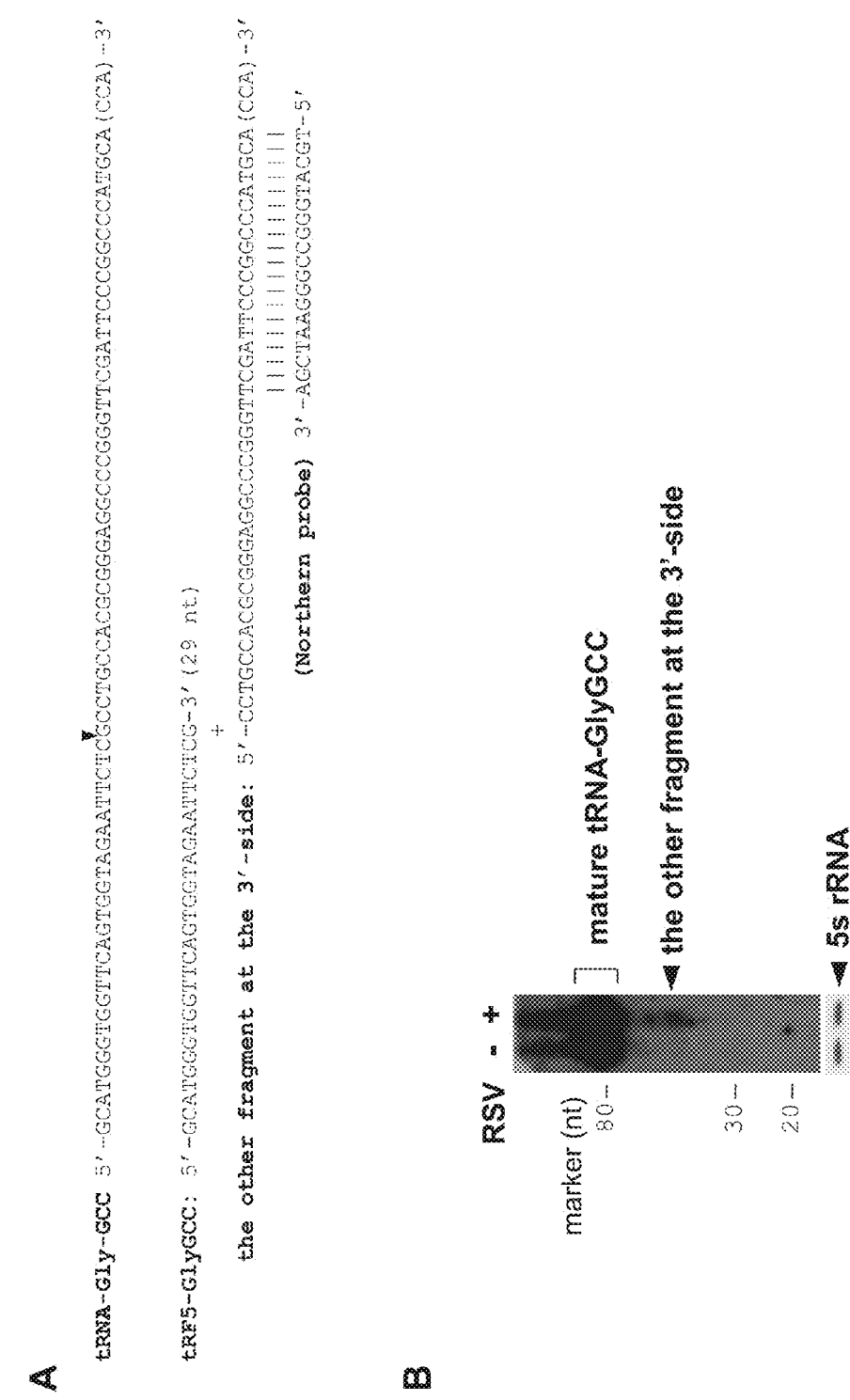
FIG. 12. Northern hybridization of 3'-end of GlyGCC tRNA. tRNA-Gly-GCC, SEQ ID NO:86; tRF-GlyGCC, SEQ ID NO:13; 45 nt fragment, SEQ ID NO:103; Northern probe, SEQ ID NO:104.

Biogenesis of tRF5-GluCTC. Next, we attempted to investigate how tRF5s were generated. There are two likely possibilities for the production of tRF-5s; one is that tRF-5s are products of endonuclease cleavage, and the other is that tRF-5s are remnants of 3'-to-5'-exonuclease digestion. As shown in FIG. 12, the 3'-side fragment was detectable by Northern blot using a probe recognizing the 3'-end, supporting the endonuclease mechanism.

Figure 6:
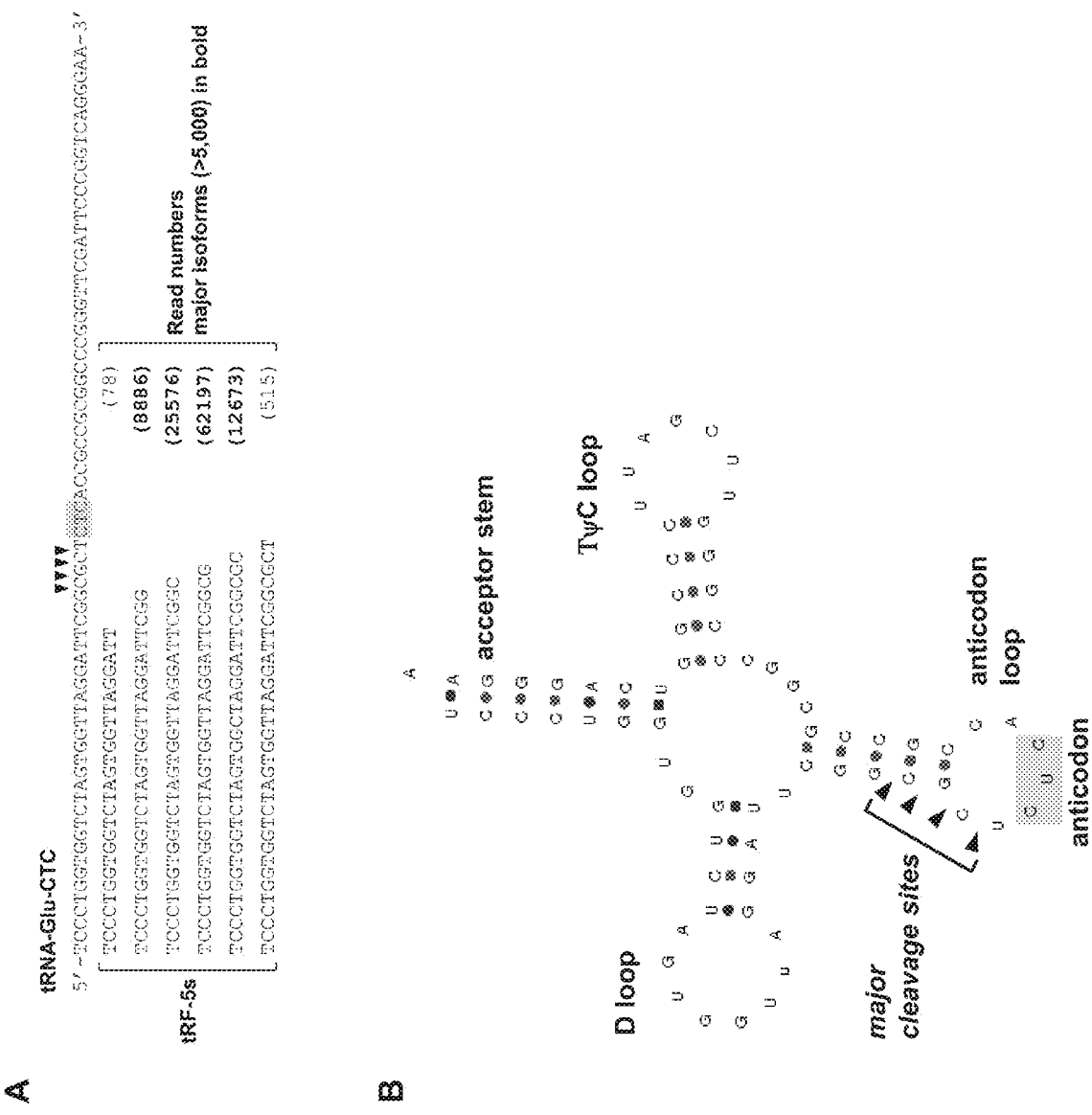
FIG. 6. Cleavage sites in tRNAs to produce tRF5-GluCTC. A. Alignment of tRF5-GluCTC isoforms (SEQ ID NO:s97-102) to their parental mature tRNA (tRNA-Glu-CTC, SEQ ID NO:96) with read numbers listed in parentheses. According to the read numbers of major isoforms (cloned reads>5000, listed in bold), cleavage sites are designated by downward arrows. The anticodon is highlighted in grey. B. Major cleavage sites and the anticodon are designated in the tRNA cloverleaf structure (SEQ ID NO:96). tRF, tRNA-derived RNA fragment; tRNA, transfer RNA.
Figure 13:
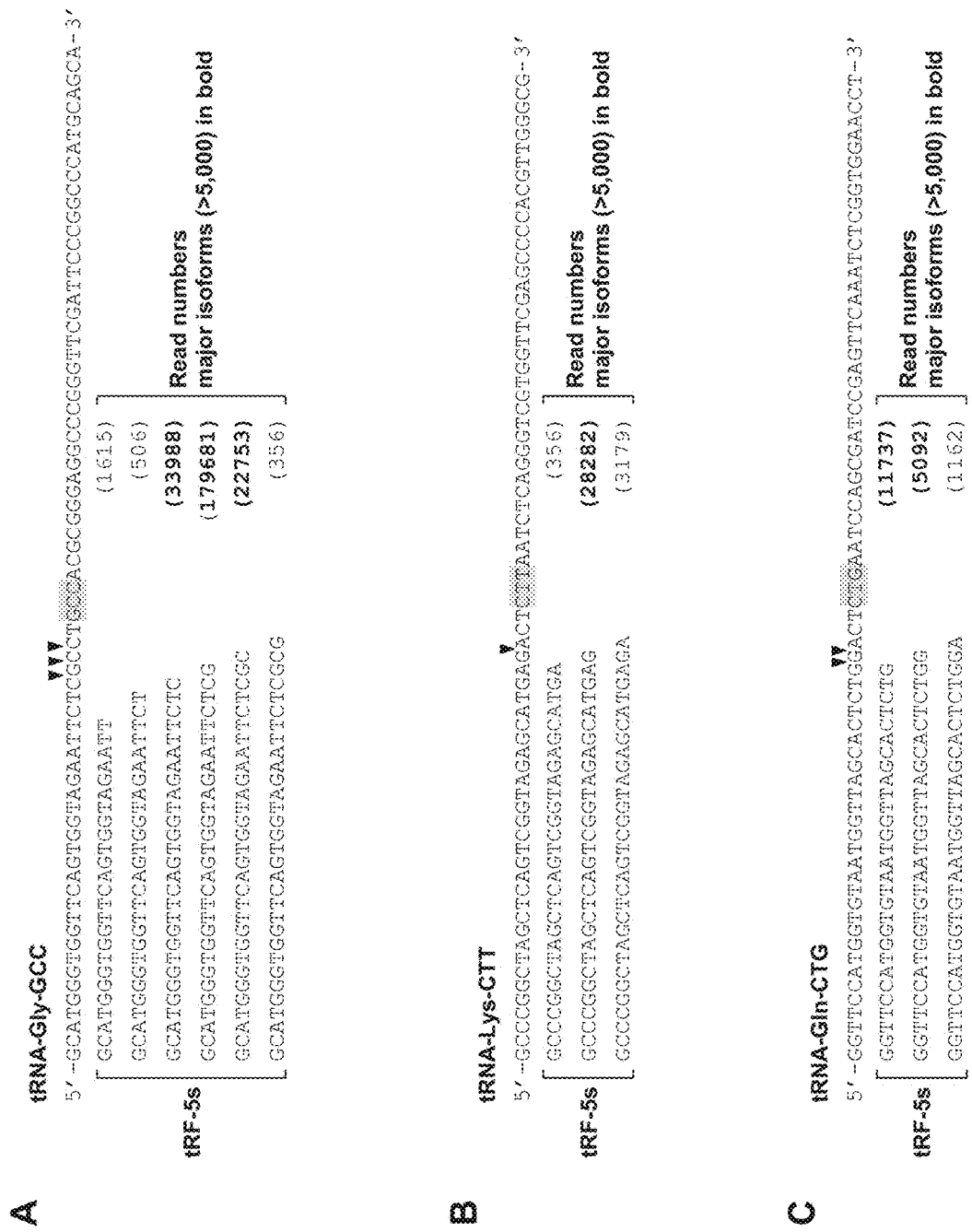
FIG. 13. Cleavage sites in mature tRNAs to produce tRF5 series. A. tRNA-Gly-GCC, SEQ ID NO:105; tRF-5s isoforms, SEQ ID NOs:106, 107, 018, 13, 109, and 110, respectively. B. tRNA-Lys-CTT, SEQ ID NO:111; tRF-5s isoforms, SEQ ID NOs: 112, 113, and 114, respectively. C. tRNA-Gln-CTG, SEQ ID NO:115; tRF-5s, SEQ ID NOs: 117, 118, and 119, respectively.

Close inspection of tRF5-GluCTC in the high-throughput data revealed several isoforms with different 3'-ends (FIGS. 6A and 13), which provided a clue to cleavage sites. In the tRNA secondary structure, they were located at the 5'-side of the anti-codon loop (FIG. 6B). Also, we noticed that the nts prior to the major cleavage sites were Gs or Cs (FIGS. 6A and 13). These preferences in nt and location further supports the notion that tRFs are not randomly generated, but produced via a specific pathway.

Figure 14:
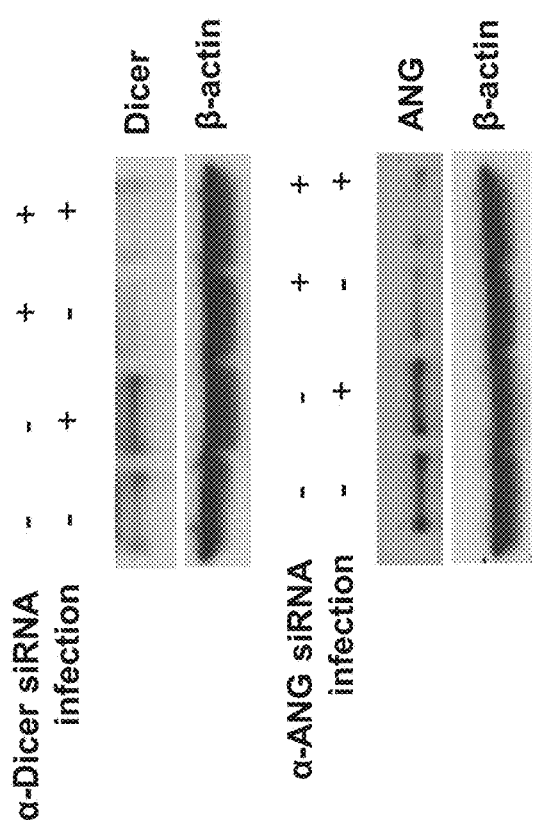
FIG. 14. Gene silencing of Dicer and ANG.

Ribonucleases targeting the tRNA anticodon loop have been found in both prokaryotes and eukaryotes (Ardelt et al., (1991) J Biol Chem 266:245-251, Kaufmann (2000) Trends Biochem Sci 25:70-74, Suhasini et al., (2006) J Biol Chem 281:12201-12209). Recently, a ribonuclease called angiogenin (ANG) has been reported to be responsible for stress-induced cleavage of tRNA at the anticodon loop in mammalian cells (Emara et al., (2010) J Biol Chem 285:10959-10968, Yamasaki et al., (2009) J Cell Biol 185:35-42). It is well known that viral infection causes cellular stresses (Akaike et al., (2000) Immunol 101:300-308, Bitko et al., (2001) J Cell Biochem 80:441-454). To test whether RSV infection produced tRF-5s through ANG induction, we suppressed ANG by a siRNA and measured tRF5-GluCTC in RSV-infected A549 cells. When ANG was suppressed by the siRNA, the induction of tRF5-GluCTC by RSV infection was significantly decreased (>50%) (FIGS. 7A and B). For comparison, knockdown experiments for other ribonucleases (Dicer, Drosha, ELAC2 and RNaseL) were performed. Dicer and Drosha are required for the generation of miRNAs (Esteller, (2011) Nat Rev Genet 12:861-874). As mentioned earlier, ELAC2 cleaves precursor tRNA to generate the tRF-1 series (see FIG. 9). RNaseL is an interferon-induced ribonuclease [reviewed in Castelli et al., (1998) Biomed Pharmacother 52:386-390]. We found that none of these ribonucleases affected the expression of tRF5-GluCTC upon RSV infection (FIG. 7A). Efficient knockdown was confirmed by qRT-PCR measurement of each mRNA (FIG. 7C) and by Western blot selectively for ANG and Dicer (FIG. 14). Notably, the induction of tRF-5-GluCTC by RSV is independent of Dicer or Drosha, reinforcing that its trans-silencing activity is distinct from that of siRNA/miRNA. Collectively, our data suggest that the production of tRF-5s upon RSV infection specifically required ANG.

Discussion tRFs were recently identified sncRNAs which have been suggested to regulate cell proliferation, stress-induced translational suppression and stress granule assembly in mammalian cells (Emara et al., (2010) J Biol Chem 285:10959-10968, Yamasaki et al., (2009) J Cell Biol 185:35-42, Lee et al., (2009) Genes Dev 23:2639-2649). Plants, such as *Cucurbita maxima, Arabidopsis thaliana* and *Arabidopsis* roots, also express tRNA-derived sncRNAs, which are present in the phloem sap or are induced under stress conditions such as oxidative stress and phosphate starvation (Hsieh et al., (2009) Plant Physiol 151:2120-2132, Zhang et al., (2009) Plant Physiol 150:378-387). Some microbes such as *Streptomyces coelicolor* and *Tetrahymena thermophila* have been reported to produce tRFs in response to starvation (Lee et al., (2005) J Biol Chem 280:42744-42749, Haiser et al., (2008) Nucleic Acids Res 36:732-741), suggesting universal expression of tRFs among different organisms.

This study is the first report of the induction and function of tRFs in response to virus infection in human airway epithelial cells. We have observed a robust induction of tRNA cleavage upon RSV infection and have provided evidence that tRFs are specifically generated and biologically functional: 1) the induction of tRFs is virus-specific (FIG. 3B); 2) not all tRNAs but a subset of tRNAs are cleaved (Table 1); 3) cleavage sites are not random but located at the tRNA anticodon loop (FIG. 6); and 4) one tRF has a gene silencing function, by a mechanism that is distinct from the gene silencing mechanism of miRNA/siRNA, and promotes RSV replication (FIG. 4-5).

It is known that a miRNA expression profile is cell type-specific and its change in response to viral infections is virus-specific (Boss et al., (2010) Curr Opin Microbiol 13:540-545). Likewise, we expect differential expression of tRFs in diverse cells/tissues. Previous high-throughput sequencing data captured tRF-5, -3, and -1 series in comparable quantities in prostate cancer cells (Lee et al., (2009) Genes Dev 23:2639-2649), while tRFs in RSV-infected cells are mostly tRF-5 series. Results shown in FIG. 3B also demonstrated that tRF regulation is virus-specific. Given accumulated evidence for the functions of tRFs, future efforts are needed to expand the repertoire of tRFs, which requires accumulation of ultra-high-throughput sequencing data and their proper archive. It should be noted that tRFs were usually filtered away as a routine step in sequencing data analyses. As shown herein, we are accumulating the knowledge and establishing techniques to explore the functions of tRFs in the context of viral infection, and we expect that these will lead us to define the roles of other tRF5s, such as tRF5-GlyGCC and tRF5-LysCTT, in response to RSV in the near future.

Recent reports have substantiated that tRNA cleavage is one mechanism of tRF biogenesis. In our data, the majority of tRFs are about 30 nts long and this size range is very similar to that of tRNA halves identified in bacteria, fungi, and plants (Lee et al., (2005) J Biol Chem 280:42744-42749, Haiser et al., (2008) Nucleic Acids Res 36:732-741, Thompson et al., (2008) RNA 14:2095-2103). In all cases, cleavage sites of these tRFs fall within the anticodon loop. However, we recognized that our tRFs are distinct from previously identified tRNA halves. For example, our cleavage sites are biased towards the 5'-side of the anticodon, whereas the cleavage sites in bacteria, fungi, and plants are distributed throughout the anticodon loop and the TψC arm. In addition, the cleavage enzymes are different. In *Saccharomyces cerevisiae*, it is Rny1p, an RNase belonging to the RNaseT2 family and induced in response to an oxidative stress (Thompson et al., (2009) J Cell Biol 185:43-50). In mammalian cells, it is an RNaseA enzyme ANG [FIG. 7 and Emara et al., (2010) J Biol Chem 285:10959-10968, Yamasaki et al., (2009) J Cell Biol 185:35-42].

Figure 7:
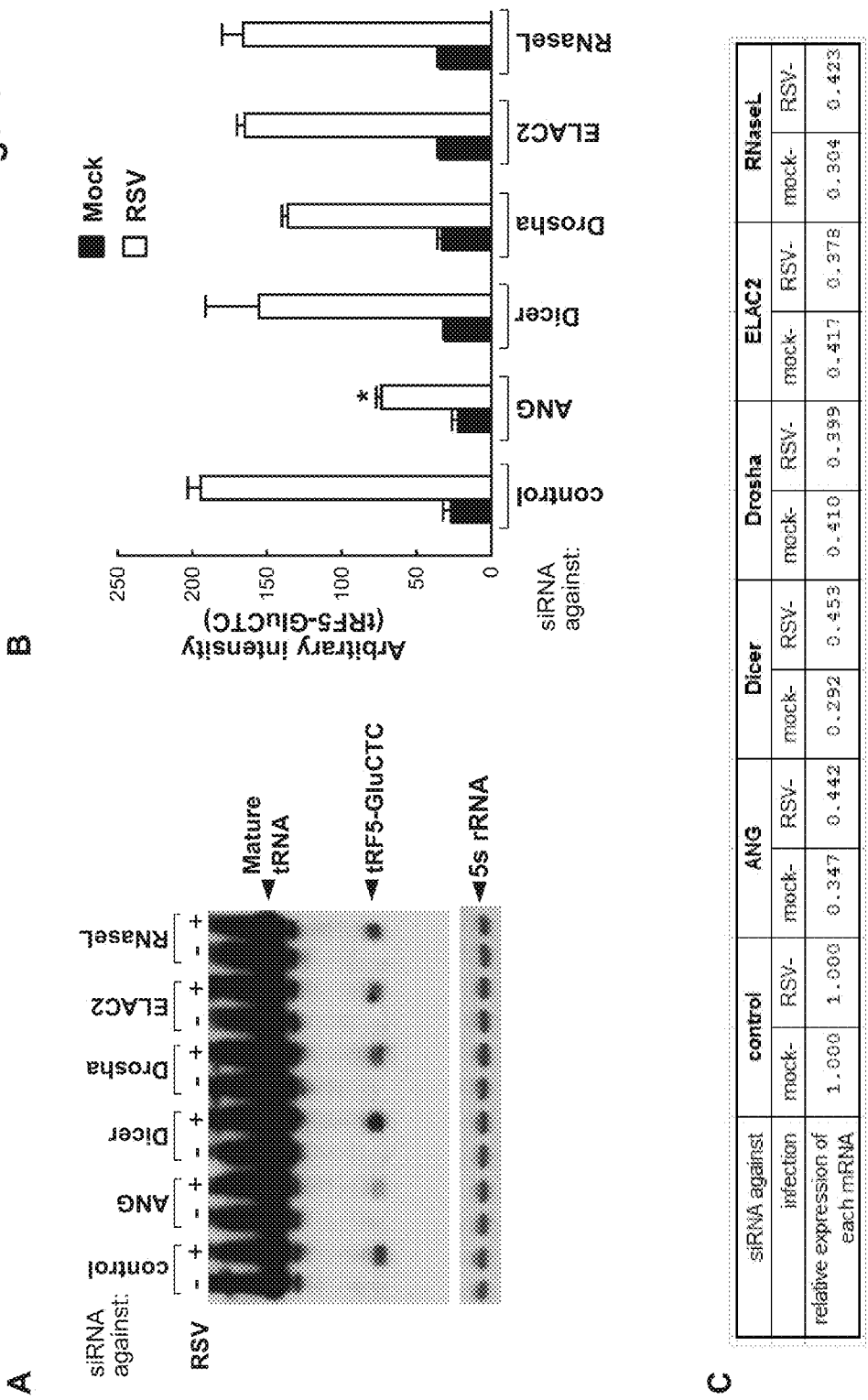
FIG. 7. tRF5-GluCTC is generated by Angiogenin. A. A549 cells were transfected with 120 nM of siRNA against indicated proteins or control siRNA as a negative control. At 40 h post-transfection, the cells were mock- or RSV-infected for 6 h. Total RNAs were then subjected to Northern hybridization as described at B in FIG. 3 (top panel). 5S rRNA expression is shown for equal loading (bottom panel). B. Densitometric analysis of band intensities of tRF5-GluCTC in panel A. Band intensity was quantified using VisionWorksLS image acquisition and analysis software from UVP. Band intensity after 5S rRNA normalization are presented as mean±SE of arbitrary units. C. The suppression of target mRNAs by each siRNA was confirmed by Q-RT-PCR measurement. The values are the relative expression levels of each mRNA, with the value of control siRNA set as one. ANG, angiogenin; qRT-PCR, quantitative reverse transcription-PCR; RSV, respiratory syncytial virus; siRNA, small-interfering RNA; tRF, tRNA-derived RNA fragment; tRNA, transfer RNA.

In the context of RSV infection, the most important aspect is tRF's biological function. In this study, we have shown that one tRF, tRF5-GluCTC, exhibited trans-silencing capability against target genes (FIG. 4). Although such activity by tRF-5s has been reported (Haussecker et al., (2010) RNA 16:673-695), the tRF-5s therein were ~21-nt thus distinct from our tRF5-GluCTC. How did the 31-nt long tRF5-GluCTC exert a suppressive effect? Given that tRF5-GluCTC was localized in the cytoplasm (FIG. 3E), it seemed to recognize complementary sequences in its target mRNAs, but not through the same mechanism used by canonical miRNA/siRNA. First, the 5'-end sequences of its target site (thus the 3'-end of tRF5-GluCTC) was most critical for their interaction (FIGS. 4A and D), which was opposite to the sequence requirement for miRNA/siRNA. Second, the processing of tRF5-GluCTC did not require Dicer (FIG. 7). Third, tRF5-GluCTC was longer than typical miRNA/siRNA. We are currently investigating the molecular mechanism(s) by which tRF5-GluCTC suppressed target gene expression.

Genes involved in host defense to viral infection are functionally important in controlling viral replication (Gerlier et al., (2011) Microbiol Mol Biol Rev 75:468-490). Our data demonstrates that tRF5-GluCTC promotes RSV replication. Therefore, it is possible that RSV-induced tRFs (at least tRF5-GluCTC) controls viral replication through suppressing the expression of host defense genes which disfavor virus propagation. Currently, we are searching for tRF5-GluCTC's target genes. This identification will be facilitated by clarifying the molecular mechanism underlying its silencing activity. It is also possible that RSV-induced tRF5-GluCTC regulates RSV replication through targeting mRNAs encoding RSV proteins. However, we think it is unlikely as viral mRNA degradation would inhibit viral replication, which is inconsistent with the results showing the promotion of RSV replication by tRF5-GluCTC (FIG. 5). tRF5-GluCTC might interact with the viral genome/antigenome and thereby provide the protection of viral genome/antigenome stability, which might favor the viral replication.

Techniques to express, inhibit, and deliver small RNAs are well developed for siRNA/miRNA-based therapy. For example, nasally inhaled siRNA against RSV genes has been recently shown to offer a fast, potent and easily administrable antiviral regimen against RSV infection in humans (Bitko et al., (2005) Nat Med 11:50-55, Zhang et al., (2005) Nat Med 11:56-62). Since tRFs, at least for tRF5-GluCTC, promotes RSV infection (FIG. 5), co-administration of a siRNA (DeVincenzo et al., PNAS USA, 2010, 107:8800-8805) and anti-tRF oligonucleotide may promote stronger antiviral effects, suggesting a potential translational application for this study.

EXAMPLE 2

Use of t-RFs to Promote RSV Replication in Mice

The tRF tRF5-GluCTC promotes RSV replication in mice. Anti-tRF5-GluCTC (anti-GluCTC, see FIG. 4a) or control (CN) oligo (5 nmol/mice) was mixed with 5 µl TransIT-TKO transfection reagent (Mirus, Madison, Wis.) in 50 µl Opti-MEM (Invitrogen), followed by intranasal inoculation into BALB/c mice (n=3/group). After 4 h, mice were mock-infected or infected with RSV at $10^7$ pfu/mouse. RSV replication in the lungs was determined on day 2 p.i. (A). * denotes p<0.05, relative to anti-GluCTC-treated mice. (B) Lung RNAs were also extracted, followed by Northern Blot to detect tRF5-GluCTC. The results are shown in FIG. 15.

Figure 15:
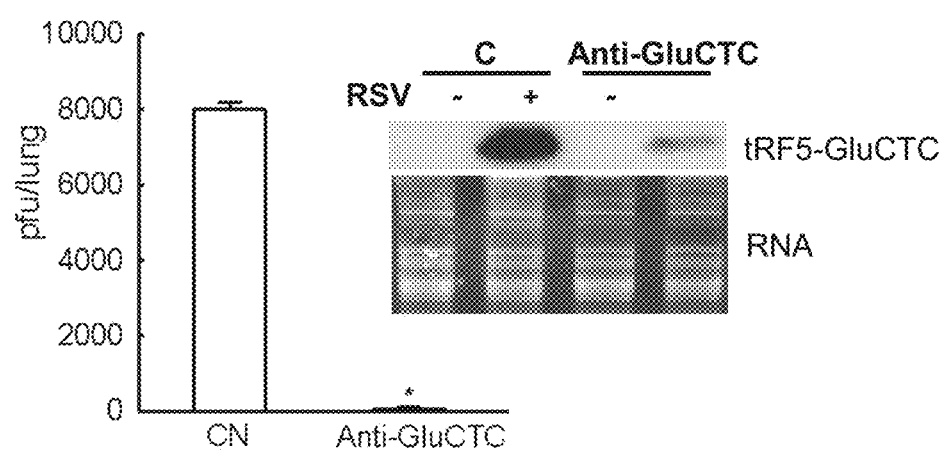
FIG. 15. tRF5-GluCTC promotes RSV replication in mice, and an antisense-tRF5-GluCTC inhibits RSV replication in mice. (A). plaque-forming units of RSV in lung on day 2 p.i; * denotes p<0.05, relative to anti-GluCTC-treated mice. (B) Lung RNAs showing detected tRF5-GluCTC. CN, control oligo; Anti-GluCTC, inhibitor oligo.

As shown in FIG. 15, RSV replication was significantly inhibited by the antisense treatment.

EXAMPLE 3

Respiratory Syncytial Virus Utilizes a tRNA 5'-End Fragment to Suppress the Host Antiviral Response Through a Novel Targeting Mechanism Small non-coding RNAs (sncRNAs) are non-protein-coding RNAs of length≤200 nucleotides (nts). A major advance in understanding the significance sncRNAs was the discovery of microRNAs (miRNAs) and their functions in many diseases, followed by identification of other classes of sncRNAs. However, very little is known about the biological roles of newly discovered sncRNAs, including tRNA-derived RNA Fragments (tRFs). Our recent publication demonstrated that tRFs are abundantly induced by respiratory syncytial virus (RSV), the single most important cause of lower respiratory tract infection (LRTI) during infancy and early childhood, and a tRF called tRF5-GluCTC promotes RSV replication, with underlying mechanism(s) completely unknown. Here, we show that tRF5-GluCTC favors RSV replication via suppressing apolipoprotein E receptor 2 (ApoER2), an anti-RSV protein newly identified in this study. ApoER2 is also known as LRP-8. tRF5-GluCTC interacts with 3'-untranslated region (UTR) of ApoER2 in a sequence-specific manner, leading to ApoER2 mRNA degradation. However, unlike miRNAs, the 3'-portion of tRF-GluCTC is the most critical region for its trans-silencing activity. Our report is the first example that RSV utilizes a host sncRNA to favor its replication and identifies a new mode of sncRNA-target interaction. The new knowledge and methodology obtained from this study will directly facilitate the development of therapeutic molecules to reduce the morbidity and mortality associated with RSV infections.

In a recent effort in identifying key ncRNA signatures in response to RSV infection, we found that tRNA-derived RNA Fragments (tRFs), a recently identified family of sncRNAs, are significantly induced by RSV infection. Compared to miRNA, the best characterized sncRNAs with gene trans-silencing function, the induction magnitude of tRFs are much higher. The induction of many tRFs exceeds more than 50-fold, demonstrating the need to broaden the research scope on sncRNAs beyond miRNAs. As emerging sncRNAs, the functions of tRFs are largely unknown. A critical advance in tRF studies is our identification of a novel role of a tRF derived from 5'-end of mature tRNA (tRF5-GluCTC) in promoting RSV replication and gene trans-silencing, which is mechanistically distinct from miRNA (Example 1). However, whether there is any association between viral replication and the host gene-regulatory functions of tRFs is completely unknown.

To address this, we focused on identifying the endogenous targets of tRF5-GluCTC, using cutting-edge genome-wide high-throughput sequencing of RNAs associated with biotinylated tRF5-GluCTC in a combination of mutagenesis studies. Among targets, we particularly investigated the target specificity of apolipoprotein E receptor-2 (APOER2) because 1) the Basic Local Alignment Search Tool (BLAST) indicates targets matching the query sequence by ≥15 nts with scores>25 (Altschul et al., Nucleic Acids Res. 1997, 25 (17), 3389-3402; Altschul et al., J. Mol. Biol. 1990, 215 (3), 403-410), and 2) published microarray data demonstrated a significant suppression of APOER2 by RSV infection, which consistent to our previous finding on the gene trans-silencing function of tRF5'-GluCTC (Example 1, Zhang et al., J. Virol. 2001, 75 (19), 9044-9058). We found that RSV infection suppressed APOER2 expression, which was inversely recovered by antisense oligonucleotides against tRF5-GluCTC, suggesting tRF5-GluCTC-mediated APOER2 expression by RSV. Consistent to what we have recently published (Example 1), our site-directed mutagenesis studies demonstrated that the 3'-portion of tRF-GluCTC is the most critical region for the gene trans-silencing of APOER2. Since tRF5-GluCTC favors RSV replication, if APOER2 is the target of tRF5-GluCTC, it is logical to deduce that they are antiviral molecules. Our results demonstrated that APOER2 indeed played a significant role in inhibiting RSV replication, likely through interacting with the phosphoprotein (P protein) RSV. In summary, our report identified a new antiviral molecule APOER2 against RSV infection and a new mode of tRF-target interaction. The new knowledge and methodology obtained from this study will directly facilitate the development of therapeutic molecules to reduce the morbidity and mortality associated with RSV infections.

Materials and Methods

Cell lines, virus and antibody. HEp-2 and A549, human alveolar type II-like epithelial cells (both from ATCC, Manassas, Va.) were maintained as we previously described (Example 1; Ren et al., J. Gen. Virol. 2011, 92 (Pt 9), 2153-2159). RSV A2 strain was grown in HEp-2 cells and purified by sucrose gradient as described (Example 1; Ren et al., J. Gen. Virol. 2011, 92 (Pt 9), 2153-2159). Viral titer was determined by immunostaining in HEp-2 cells using polyclonal biotin-conjugated goat anti-RSV antibody (Ad direct, Barberton, Ohio) and streptavidin peroxidase polymer (Sigma, St Louis, Mo.) sequentially, as described (Example 1; Ren et al., J. Gen. Virol. 2011, 92 (Pt 9), 2153-2159).

RNA pull-down. Biotin-labeled tRF5-GluCTC mimic or its control (Sigma, St. Louis, Mo.) were transfected into A549 cells in 10-cm dishes using lipofectamine 2000 (Life Technologies, Grand Island, N.Y.) according to the manufacturer's instruction. At 8 h post transfection, cells were treated with UV crosslinking (UV Stratalinker 1800, Stratagene/Agilent, Santa Clara, Calif.) at 6 h post infection (p.i.) and then harvested using RNase inhibitor supplemented cell lysis buffer from Roche (Cat No: 11719394001, Indianapolis, Ind.). Streptavidin beads (Pierce, Rockford, Ill.) were added to pull down biotinylated oligonucleotides, followed by bead washing twice. The washing buffer was detergent free lysis buffer. The pull-down complex was then treated with protease K (New England BioLabs, Ipswich, Mass.), followed by RNA extraction using Trizol (Life Technologies) following the manufacturer's instruction.

Library construction and RNA sequencing. The library construction and RNA sequencing were performed by the Next Generation Sequencing Core at the University of Texas Medical Branch. In brief, ribosomal RNA was removed from 1 ug of total RNA using Ribo-Zero biotinylated, target-specific oligos (Epicentre, Madison, Wis.). Poly-A$^+$ RNA was removed using poly dT~ magnetic beads and the bound RNA containing predominantly adenylated mRNAs and some ncRNA (poly A$^+$ and start codon) was fragmented by incubation at 94° C. for eight minutes in 19.5 ul of fragmentation buffer (15016648, Illumina, San Diego, Calif.). First strand synthesis was performed using reverse transcriptase (Superscript II, Life Technologies) and random primers. Second strand synthesis using DNA polymerase I and RNAse H was performed using a deoxyribonucleotide mix that had dUTP substituted for dTTP. End polishing, addition of 5' phosphates and 3' adenylation and adapter ligation were performed as prescribed by the Illumina TruSeq Stranded protocol. Samples were tracked using "index tags" incorporated into the adapters. Library quality was evaluated using an Agilent DNA-1000 chip on an Agilent 2100 Bioanalyzer. Quantitation of library DNA templates was performed using qPCR and a known-size reference standard.

Cluster formation of the library DNA templates was performed using the TruSeq PE Cluster Kit v3 (Illumina) and the Illumina cBot workstation using conditions recommended by the manufacturer. Template input was adjusted to obtain a cluster density of 700-850 K/mm2. Paired end 50 base sequencing by synthesis was performed using TruSeq SBS kit v3 (Illumina) on an Illumina HiSeq 1000 using protocols defined by the manufacturer.

Northern blot. Northern hybridization for sncRNAs were performed as we previously described (Example 1; Lee et al., Genes Dev. 2009, 23 (22), 2639-2649). Briefly, RNA was separated in 15% denaturing polyacrylamide gel with 7M urea and then transferred to a positively charged nylon membrane (Amersham Biosciences, Piscataway, N.J.). The membrane was hybridized with $^{32}$P-labeled probes in ULTRAhyb®-Oligo solution (Life Technologies, Grand Island, N.Y.), followed by washing according to the manufacturer's instruction.

Western blot. The total cellular extracts of uninfected and infected cells were prepared using RIPA buffer (New England) supplied with protease inhibitor cocktail (Roche). The lysates were collected and quantified with a protein quantification kit from Bio-Rad and fractionated by SDS-PAGE, and transferred to polyvinylidene difluoride membranes. Membranes were blocked with 5% milk in TBS-Tween 20 and incubated with the proper primary antibodies according to manufacturer's instruction. As mentioned, goat anti-RSV antibody was from Ad direct. Anti-APOER2 and β-actin antibodies were obtained from Abcam (Cambridge, Mass.) and Sigma (St Louis, Mo.) respectively.

Construction of luciferase sensor plasmids and luciferase assays. The sensor plasmid "Pp-APOER2-WT" was constructed by inserting an oligonucleotide, which was complementary to APOER2's three prime untranslated region (3'-UTR) matching to tRF5-GluCTC (FIGS. 16D and 18A), into EcoRI/XhoI sites of pcDNA3.1-Zeo(+)-Pp as described (Lee et al., RNA. 2011, 17 (6), 1076-1089). Paired primers used for insertion were: 5'-AATTGTTCTGCCACTTACTC-CCACTAGACAACCAGGGA-3' (SEQ ID NO:82) and 5'-TCGATCCCTGGTTGTCTAGTGGGAGTAAGTG-GCAGAAC-3' (SEQ ID NO:83) (bold letters represent extra nts to generate EcoRI/XhoI overhangs). Three mutant plasmids were constructed in the same manner (their mutated sequences shown in FIG. 18A). An empty pcDNA3.1-Zeo (+)-Pp vector was used as a control.

To investigate the effect of RSV-induced tRF5-GluCTC on APOER2 mRNA expression, A549 cells were co-transfected with Pp-APOER2-WT sensor plasmids (firefly plasmids), pRL-CMV plasmids expressing Rr (renilla luciferase), and anti-GluCTC oligonucleotides, using Lipofetamine 2000 according to the manufacturer's instruction (Invitrogen). Empty Pp plasmids and/or anti-control oligonucleotides were used as negative controls. After 2 h of transfection, the cells were infected with mock or RSV. At 15 h post infection (p.i.), cells were lysed for luciferase assays using a Dual-luciferase kit (Promega, Madison, Wis.). Data processing and normalization was described in the legend to FIG. 18B. For this experiment, synthetic anti-GluCTC oligonucleotides which contain a backbone phosphorothioate and have 5 nts on each end substituted with 2'-O-methyl ribonucleotides were used to effectively suppress RSV-induced tRF5-GluCTC as we previously described (Example 1).

To identify the targeting specificity of tRF5-GluCTC, A549 cells were co-transfected with Pp-APOER2-WT sensor plasmids or their mutants, and Rr expressing plasmids for 24 h, followed by mock or RSV infection (MOI of 1). Cells were lysed for luciferase assays at 15 h post infection (FIG. 18C). Similarly, cells transfected with Pp-APOER2-WT or -mutant were also co-transfected with tRF5-GluCTC mimic or its control oligo using Lipofectamine 2000 to confirm the targeting specificity (FIG. 18D). Specificity was further investigated by investigating whether the luciferase suppression by the mimic is impaired by mimic mutant. In brief, cells were A549 cells were co-transfected with Pp-APOER2-WT sensor plasmids, Rr expressing plasmids, and mimic or its mutant for 15 h, followed by luciferase assays. All other descriptions, such as the concentrations of oligonucleotides and plasmids are described in FIG. 18.

RNA interference. siRNAs were purchased from Sigma or Invitrogen. 100 nM of siRNA was transfected into A549 cells, by using lipofectamine 2000 (Life Technologies), according to the manufacturer's recommendations. After 48 hours, A549 cells were mock- or RSV-infected for 6 h at a MOI of 1.

Quantitative real-time PCR (Q-RT-PCR). Total cellular RNAs were extracted using TRIzol® reagents. Q-RT-PCR for viral replication and gene transcription was performed by using SYBR as we previously described (Example 1; Ren et al., J. Virol. 2012, 86 (23), 13049-13061).

Coimmunoprecipitation (Co-IP). Logarithmically growing A549 cells in 6-well plates were cotransfected with 2 μg of PCDNA3 containing Flag-tagged APOER2 or the empty vector. Cells were mock infected or infected with RSV at MOI of 1 for 6 h, followed by cell lysis immunoprecipitation using immunoprecipitation kit from Roche (Cat#11719386001), similarly as we previously described (Ren et al., J. Virol. 2012, 86 (23), 13049-13061; Ren et al., PLoS. ONE. 2014, 9 (3), e91865). In brief, 6×10$^6$ cells were lysed using 1.5 ml of lysis buffer, followed by a preclearing. Precleared samples were exposed to 5 μg of antibody against Flag antibody, for 1 h at 4° C. 50 μl of the protein A/G-agarose were added to the samples and incubated overnight at 4° C. The immunoprecipitated (IP) complexes were recovered by centrifugation and washed three times using buffers provided by the kit. The IP complexes were eluted from the beads and subjected to SDS-PAGE followed by Western blot analysis using anti-RSV antibody. The membrane was scripted and reprobed with an anti-Flag antibody to ensure the proper IP process.

Statistical Analysis. Statistical significance was analyzed using analysis of variance (ANOVA). P value of less than 0.05 was considered significant. Mean±standard error (SE) is shown.

Results

RNAs associated with tRF5-GluCTC. tRFs are in three families: the tRF-1, -3 and -5 series. The tRF-1 series, corresponds to the 3'-trailer sequences cleaved off from precursor tRNAs, and plays a significant role in cell proliferation (Lee et al., Genes Dev. 2009, 23 (22), 2639-2649). The tRF-3 and -5 series are derived from the 3'- and 5'-ends of mature tRNAs, respectively. The functions of tRF-3 are not clear, while the expression of tRF-5 series is associated with cell development and cellular responses to stress and infection (Example 1; Gong et al., BMC. Infect. Dis. 2013, 13, 285; Emara et al., J. Biol. Chem. 2010, 285 (14), 10959-10968; Haiser et al., Nucleic Acids Res. 2008, 36 (3), 732-741; Hsieh et al., Plant Signal. Behav. 2010, 5 (5); Lee et al., J. Biol. Chem. 2005, 280 (52), 42744-42749; Loss-Morais et al., Biol. Direct. 2013, 8, 6; Peng et al., Cell Res. 2012, 22 (11), 1609-1612). However, due to the recent discovery of tRFs, only few of them have been functionally characterized and the regulatory mechanisms contributing to their function are completely unexplored.

In this study, we focused on molecular mechanisms contributing to the stimulating role of tRF5-GluCTC in RSV replication. Since tRF5-GluCTC has a gene trans-silencing function, we started our studies by identifying whether tRF5-GluCTC targets genes important for viral replication. To address that, we first used biotin-labeled tRF5-GluCTC mimic to pull down its associated targets followed by RNA sequencing. We called it HITS-ABT (high-throughput sequencing of RNAs associated with biotinylated tRF). This method has several advantages. 1) It can be used as a general method for target identification regardless of whether the regulatory functions of ncRNAs depend on certain platforms important for ncRNA-target interaction; 2) it can detect targets in a broad spectrum. As shown in FIGS. 16A (pie) and 25 (mRNA list) and Table 3 (lncRNA lists), it not only pulled down many associated mRNAs, but also lncRNAs, suggesting ncRNA-ncRNA interaction; 3) it provides an opportunity to discover new immune or antiviral genes; And 4) the target identification resolution of HITS-ABT is remarkably high. For instance, one isoform of APOER2 NM 033300, which does not have sequences at its 5'-UTR to be targeted by tRF5-GluCTC, did not bind to biotinylated tRF5-GluCTC, while other isoforms did (FIG. 16B). RT-PCR confirmed the formation of APOER2-tRF5-GluCTC complex (FIG. 16C). We have previously demonstrated that tRF5-GluCTC has a gene trans-silencing activity (Example 1), we therefore investigated whether RNA molecules bound to tRF5-GluCTC are downregulated by RSV infection to identify the targets. We identified 34 targets which have more than 9 fold reduction in expression according to the previous microarray report (Zhang et al., J. Virol. 2001, 75 (19), 9044-9058) and more than a log in tRF binding (FIG. 25). Among the list, we chose APOER2 for the experimental confirmation as it has sequence match score>25, revealed by BLAST search (Altschul et al., Nucleic Acids Res. 1997, 25 (17), 3389-3402; Altschul et al., J. Mol. Biol. 1990, 215 (3), 403-410). As shown in FIGS. 17A and B, both Northern and Western blot revealed that the expression of APOER2 was significantly inhibited by RSV infection, and RSV-suppressed expression was reversed by the treatment of antisense oligonucleotides against tRF5-GluCTC suggesting that RSV-suppressed APOER2 expression was via tRF5-GluCTC. On the other hand, the expression of APOER2 was significantly inhibited by the mimic of tRF5-GluCTC, confirming a role of tRF5-GluCTC in targeting APOER2 (FIG. 17C). The regulatory effect of tRF5-GluCTC on APOER2 is specific as the expression of TRIM 5, which has less BLAST match score than APOER2, was not inhibited by RSV infection and sensitive to antisense oligonucleotide treatment (FIG. 19).

TABLE 3

| lncRNA | Fold increase in binding |
| --- | --- |
| NR_003573_utr5_0_0_c hr9_33624223_f | 1.7 |
| NR_003662_utr5_3_0_c hr19_24009872_f | 2.5 |
| linc-ARF6-1 | 2.6 |
| linc-EPHA6-1 | 5.9 |
| linc-DHFRL1-4 | 6.0 |
| linc-FCGR1B-7 | 7.0 |

Figure 16:
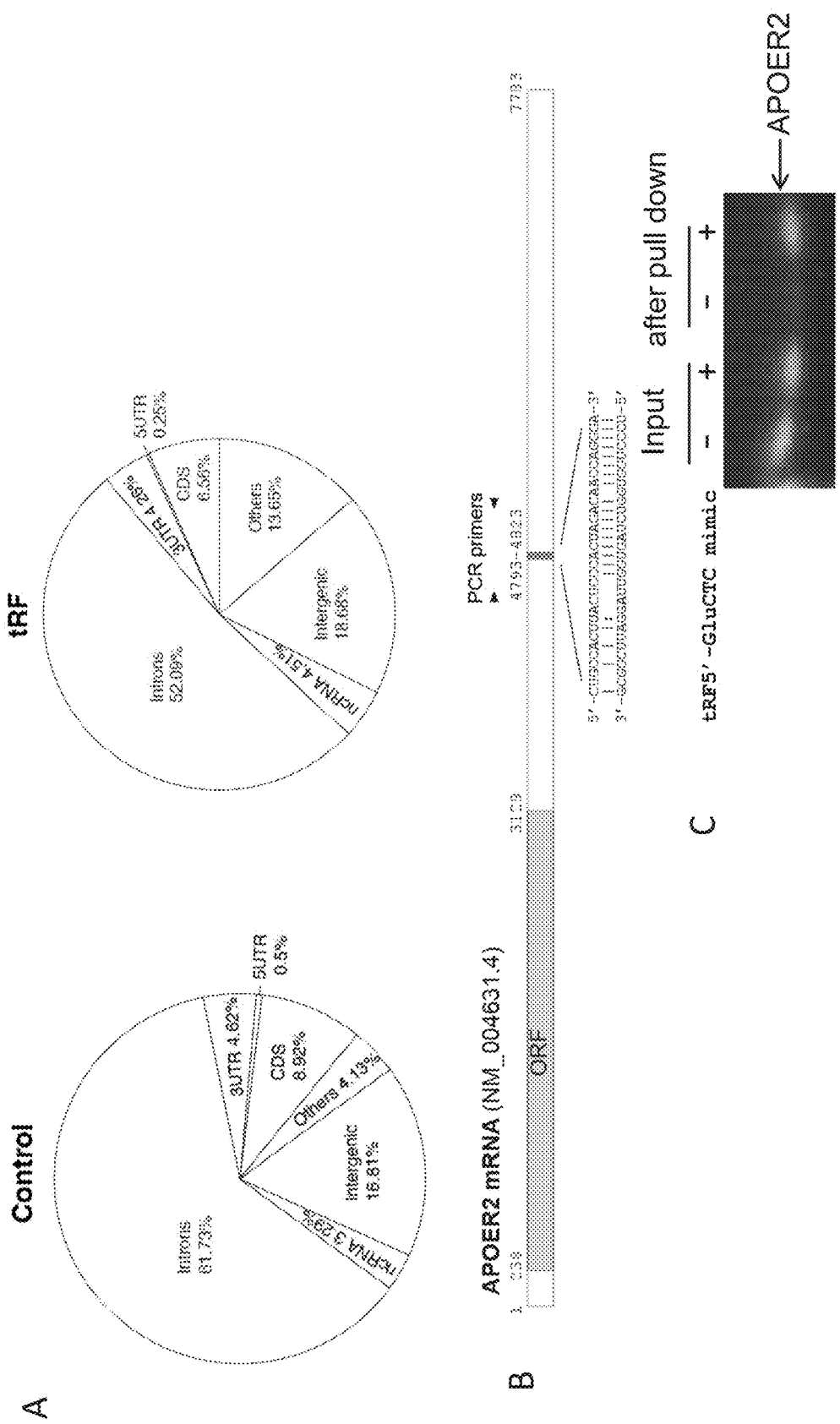
FIG. 16. A subset of genes associated with tRF5-GluCTC. (A) Classification of tRF5-GluCTC-bound RNAs. Identified human RNAs were sorted according to their origins, and their relative abundance (calculated from read numbers) was depicted in pie charts. (B) Sequence alignment of tRF5-GluCTC with APOER2. The interactive region was identified by both RNAhybrid and the binding assays. Target (WT), SEQ ID NO:120; tRF5-GluCTC, SEQ ID NO:6; (C)

To further confirm the target specificity of tRF5-GluCTC on APOER2, we take advantage of our recently developed luciferase report system for tRF's gene trans-silencing assay (Example 1). We transfected cells with a cognate sensor plasmid (designated as "Pp-APOER2-WT"), together with a plasmid expressing renilla luciferase (Rr) for normalization. The cognate sites are based on RNAhybrid analysis (Kruger et al., Nucleic Acids Res. 2006, 34 (Web Server issue), W451-W454; Rehmsmeier et al., RNA. 2004, 10 (10), 1507-1517) and also our binding results (FIG. 16). The relative luciferase activity (Pp/Rr values in y-axis) was calculated and compared between treatments. We found that the luciferase expression from a control sensor plasmid lacking the target site was not affected by RSV infection.

However, compared to mock-infection, RSV infection significantly decreased the relative luciferase activity of Pp-APOER2-WT (first black bar versus first white bar in FIG. 18B). Because RSV infection could lead to pleiotropic effects on the infected cells, we wanted to determine that the observed decrease of luciferase activity was tRF5-GluCTC specific. We therefore inhibited tRF5-GluCTC by transfecting cells with antisense oligonucleotides as we previously described (Example 1), and found that the tRF5-GluCTC suppression restored the luciferase activity that was decreased by RSV infection (right two bars versus left two bars in FIG. 18B).

Targeting specificity of tRF5-GluCTC was further investigated and confirmed by mutagenesis. In brief, we introduced 3-5 nt mutations at the 3'-, middle-, or 5'-region of the tRF-GluCTC target site in the sensor plasmid "Pp-APOER2-WT" as depicted in FIG. 18A. Contrary to Pp-APOER2-WT, the luciferase activity of Pp-APOER2-Mut 3, which lacks interactive sites with 3'-portion of tRF5-GluCTC, was completely unresponsive to RSV infection, indicating that imperfect sequence match between 3'-portion of tRF5-GluCTC and the 5'-portion of APOER2 targeted domain was critical for the gene trans-silencing activity of tRF5-GluCTC (FIG. 18C). This is also consistent to our previous finding in distinct major targeting domain of tRF5-GluCTC and miRNA/siRNA, whose 5'-portion (called "seed sequence") is known to be important for target recognition (Example 1, Esteller, Nat. Rev. Genet. 2011, 12 (12), 861-874). Besides the 3'-portion, the 5'-portion of tRF5-GluCTC also plays a role in recognizing APOER2, but in a less extension than its 5'-end. We also used the ectopic expression of tRF5-GluCTC to confirm importance of two ends of targets for the recognition by tRF5-GluCTC. As shown in FIG. 18D, upon transfection the mimic into A549 cells, the luciferase activity of "Pp-APOER2-WT" was significantly suppressed by tRF-GluCTC mimic, while mutants. In addition, the luciferase expression of "Pp-APOER2-WT" could not be inhibited by the mimic mutant completely lacking matching nts in the 3'-end of mimic (FIG. 18E), confirming that tRF5-GluCTC targets APOER2 in a sequence specific manner.

Antiviral function of APOER2. We have previously shown that tRF5-GluCTC promotes RSV replication in airway epithelial cells. Since tRNA GluCTC is conserved between human and mouse and the cleavage was also observed in infected mice (FIG. 20), the stimulatory effect of tRF5-GluCTC was also investigated in vivo. As shown in FIG. 20, pulmonary RSV replication, in mice was significantly suppressed by anti-tRF5-GluCTC oligo, both at day 2 when viral replication starts to be detectable and day 5 when RSV replication reaches its peak, confirming that tRF5-GluCTC promotes pulmonary RSV replication.

Since tRF5-GluCTC promotes RSV replication and targeted APOER2, it is reasonable to hypothesize that APOER2 is an antiviral protein and RSV targets APOER2 to enhance its survival in cells. Therefore, we examined the effect of APOER2 on RSV replication using microplaque immunoperoxidase detection assays to compare the yield of infectious viral particles produced by the cells, which were transfected with anti-control- or anti-APOER2 siRNAs. As shown in FIG. 21A, suppression of APOER2 led to enhanced RSV yield. In addition, real-time PCR assay for viral gene transcription (FIG. 21B) supported the result of FIG. 21A.

Previously, it has been shown that the induction of chemokines and cytokines by RSV infection is viral replication dependent (Haeberle et al., J Virol 2001, 75 (2), 878-890). In agreement with the data of FIG. 21A, the induction of IL-8 was significantly increased when RSV replication was enhanced by APOER2 silencing (FIG. 21C). Conversely, overexpression of APOER2 significantly inhibited RSV replication and reduced associated chemokine induction, further confirming the antiviral role of APOER2 in RSV replication (FIG. 22). We also found that the suppression of RSV replication by APOER2 is dose dependent (FIG. 23).

Antiviral mechanism of APOER2. Since APOER2 affected the viral RNA replication (FIGS. 21 and 22), we investigated whether it interacts with any RSV component(s) which are important for controlling viral RNA synthesis. To investigate that, cells transfected with/without Flag-tagged APOER2 were mock infected or infected with RSV for 6 h. Cells were lysed followed by immunoprecipitation using an anti-Flag antibody to pull down APOER2 complex. The immunoprecipitated complex was separated on 4-20% SDS-PAGE and transferred onto a PVDF membrane. Western blot using an anti-RSV antibody revealed that RSV P protein was co-precipitated with APOER2, demonstrating the APOER2·P interaction (FIG. 24A). Since the P protein is a key component of RNA-dependent RNA polymerases of RSV (Lu et al., J. Virol. 2002, 76 (21), 10776-10784), this result suggested that APOER2 targeted RSV P protein to achieve its antiviral function. To confirm that APOER2 achieve its antiviral function via suppressing the function of RSV P, we exogenously supplemented the P protein into APOER2 expressing cells and found P protein reversed the inhibition of APOER2 on RSV replication (FIG. 24B). Overall, all these results demonstrated that APOER2 likely targets the P protein of RSV leading to decreased viral replication.

Discussion tRNA-derived RNA Fragments (tRFs) are a recently discovered sncRNA family, ubiquitously expressed in organisms ranging from prokaryotes to humans (Lee et al., Genes Dev. 2009, 23 (22), 2639-2649; Hsieh et al., Plant Signal. Behav. 2010, 5 (5); Peng et al., Cell Res. 2012, 22 (11), 1609-1612; Wang et al., Mol. Ther. 2012; Franzen et al., PLoS. Negl. Trop. Dis. 2011, 5 (8), e1283; Hsieh et al., Plant Physiol 2009, 151 (4), 2120-2132; Kaufmann, Trends Biochem. Sci. 2000, 25 (2), 70-74), yet their biological functions and the mechanism(s) underlying their functions are largely unknown. Studies by our group have shown that RSV abundantly induces functional tRFs and one of significant induced isoform tRF5-GluCTC is involved in the regulation of RSV replication (Example 1). Following our observation, there are two more reports demonstrating a role of tRFs in human T-cell leukemia virus and rickettsia infection (Gong et al., BMC. Infect. Dis. 2013, 13, 285; Ruggero et al., J. Virol. 2014, 88 (7), 3612-3622). However the tRF species induced by these pathogens are different, suggesting the tRF pattern induction is pathogen specific. However, the mechanism(s) contributing to their function in infectious diseases are completely unknown.

Non-tRF sncRNAs can regulate viral replication via targeting host genes (Asirvatham et al., Cytokine 2009, 45 (2), 58-69; Boss et al., 2010, 13 (4), 540-545; Haasnoot et al., Methods Mol. Biol. 2011, 721, 23-41). Compared to miRNAs, tRF5-GluCTC's silencing activity has unique features—Dicer-independence and sequence requirements beyond the seed sequence (Example 1). Despite the lack of a specific target prediction algorithm for tRFs, we found a candidate of tRF5-GluCTC by a novel approach: a BLAST and RNAhybrid analysis combined with data analyses on gene transcription in response to RSV infection and RNA sequencing of the tRF5-GluCTC complex (Zhang et al., J. Virol. 2001, 75 (19), 9044-9058) In our previous study, we also demonstrate that tRF5-GluCTC has a gene trans-silencing function which is distinct from miRNA (Example 1). We therefore investigated whether tRF5-GluCTC targets any endogenous antiviral molecule(s) to achieve its stimulatory role in RSV replication. Our experiment results including those from RNA sequencing of tRF5-GluCTC bound RNAs, BLAST search and RNAhybrid prediction, and the APOER2 regulation by tRF5-GluCTC demonstrated that APOER2 is the target of tRF5-GluCTC. The interaction of APOER2 and tRF5-GluCTC is direct as their interplay is sequence specific. In this study, we also identified that APOER2 is an antiviral protein as cells with downregulated APOER2 had more aggressive RSV replication, while cells with APOER2 overexpression had significant less replication. All of these facts highlighted the importance of tRF5-GluCTC in controlling RSV replication.

APOER2, an low-density lipoprotein receptor, has been reported to mediate the endocytosis of flaviviridae viruses (Agnello et al., Proc. Natl. Acad. Sci. U.S.A 1999, 96 (22), 12766-12771). The lack of detectable APOER2 on cells are known to be resistant to Flaviviridae viruses infection. Other than that, the biological roles of APOER2 in infectious disease have not been explored. However, APOER2 seemed not necessary for the entry of RSV, as suppressed APOER2 expression led to enhanced RSV replication (FIG. 21). Since APOER2 suppressed the viral RNA replication, we therefore investigate whether APOER2 functions as an antiviral molecule via targeting any viral components involved in RSV RNA synthesis. We found that APOER2 interacts with RSV phosphoprotein P, a viral RNA polymerase, possibly leading to suppressed viral replication.

Other than APOER2, there are several targets which were found to be associated with tRF5-GluCTC and suppressed by RSV infection (FIG. 25 and Table 3). In the future, we will continue investigate whether they are targets of tRF5-GluCTC. Among those, some were lncRNAs. Given the emerging role of lncRNAs viral infections (Gomez et al., Cell 2013, 152 (4), 743-754; Josset et al., RNA. Biol. 2014, 11 (7); Peng et al., MBio. 2010, 1 (5)), these results suggest a potential role of these lncRNAs in RSV replication. Overall, the evidence of the induction of tRFs in the infectious diseases is emerging and accumulating, whether and how they function is important to understand the changes in tRF profiles by pathogens. The role of tRF5-GluCTC in gene expression regulation, which is distinct from miRNA, also provides a novel gene regulatory network for future RSV replication control strategies.

EXAMPLE 4

Respiratory Syncytial Virus (RSV) is the most leading cause of lower respiratory tract infection (LRTI) in children from infancy up to early childhood. RSV is a negative sense, single-stranded RNA virus, belonging to the Paramoxiviridae. Recently, it has been demonstrated that RSV infection results in changes to host cellular small non-coding RNA (sncRNA) expression. With RSV infections, the predominately sncRNA expressions are tRNA-derived RNA fragments (tRFs), as a results of endonuclease ANG cleavage at a specific site. The tRFs function and role they play in viral and host interaction are still unknown. Herein, we examined the role of tRFs derived the 5'-end of mature tRF GlyCCC, tRNA LysCTT and tRNA CysGCA (named as tRF5-GlyGCC, GlyCCC, LysCTT and CysGCA respectively) in controlling RSV replication and associated chemokine/cytokine induction. We found that cells transfected with an anti-tRF5-GlyGCC or anti-tRF5-CysGCA oligos did not lead to significant changes in RSV replication compared to the cells transfected with control antisense oligo, while RSV replication in anti-tRF5-GlyCCC- or anti-tRF5-LysCTT-transfected cells was remarkably suppressed (more than a log). In addition, the inhibited viral replication led to impaired cytokines/chemokines induction. Vice versa, cells supplemented with tRF5-GlyCCC and tRF5-LysCTT mimics significantly enhanced RSV replication, confirming these two tRFs are important for RSV replication. Further investigations are needed to unravel the molecular mechanisms underlying the functions of tRF5-GlyCCC and tRF5-LysCTT.

Material and Methods

Cell Lines. A549, human alveolar type II-like epithelial cells, were used for infection assays and were maintained in F12-K media containing 10% FBS, 1% penicillin, and 1% streptomycin by volume. HEp-2 cells used for growing RSV and determining viral titer were maintained in minimal essential medium containing 10% FBS, 1% penicillin, and 1% streptomycin by volume.

Transfection. Confluent A549 cells were transfected with an antisense oligo (final concentration: 100 nM) against a specific tRF or a control α-oligo by lipofectamine 2000 [100 nM]. At 2 h post transfection, Cells were then infected or mock-infected with RSV at MOI of 1 for 15 hours at 37° C. Samples were then collected in separate supernatant and cell fractions or as both cell and supernatant mixtures.

Viral Titer. Fractions containing only the supernatant of transfected cells (Super.) or the supernatant combined with the intracellular portion obtained through sonication (Total) were collected. HEp-2 cells in 96-well plates were then infected with a serial dilution of these virus-containing fractions and immunostained with biotinylated anti-RSV antibody followed by streptavidin peroxidase and 3-amino-9-ethyl-carbazole substrate. Viral plaques were then assessed with light microscopy.

ELISA. Enzyme-linked immunosorbent assays (ELISA) for both IL-8 and RANTES chemokines were performed on supernatant fractions using DuoSet ELISA kits.

Western Blot (WB). Protein samples extracted from cells were suspended were loaded into a 10% PAGE gel, followed by WB to detect RSV proteins using a primary antibody against RSV and corresponding secondary antibody, then visualized using Pierce ECL Western Blotting substrate with UV photography. Membranes were then stripped and re-probed for β-actin.

Dual Luciferase. Confluent A549 cells in twenty-four-well plates were incubated at 37 C for 2 hours in 0.5 mL/well 10% FBS F12-K followed by transfection of 0.1 µg of a synthetic Firefly-linked tRF oligo (tRF5-GlyCCC or tRF5-LysCTT), 0.01 µg of a Renilla oligo, 1.5 µL of tRF5-GlyCCC α-oligo [100 nM] or a control α-oligo [100 nM]. Plates were then infected or mock-infected with RSV at MOI=2 in 1.0 mL 0% FBS F12-K and incubated for 24 hours at 37 C. Samples were then assessed using Dual-Glo Luciferase Assay System.

Bio-plex Assay. Bio-plex assays were performed for the induction of cytokines and chemokines by RSV.

Statistical Analysis. Statistical significance was established by using Student's t-test (p≤0.05).

Results

Anti-Sence and Their Effect on Viral Replication. Viral titers were assessed of the supernatants of transfected cells with α-tRF oligo (α-tRF5-GlyCCC, α-tRF5-LysCTT, and α-tRF5-CysGCA) or scramble oligo as a control that were infected with RSV at a mode of infection (MOI) of 1. The results are shown in FIG. 26 is an average of three separate experiments. Antisense oligos to tRF5-GlyCCC, and tRF5-LysCTT reduced RSV replication, and an antisense oligo to tRF5-CysGCA had no effect under to conditions tested.

tRF5-GlyCCC specifically inhibits Viral Protein Production. Western Blot was carried out on mock- or RSV-infected cells transfected with antisense oligo specifically against tRFs or with a scrambled control oligo. As shown in FIG. 27, an antisense oligo to the tRF5-GlyCCC sequence inhibited production of viral protein. The two antisense oligos varied at four bases (see positions 3, 4, 5, and 7 of the nucleotides shown in FIG. 27, suggesting the inhibition is specific.

Cells, transfected with antisense oligos as indicated in FIG. 28 were infected with RSV at MOI of 1 for 15 h. Mock infection was used as a negative control. The supernatants were harvested and cytokines/chemokines were measured by Bio-plex assays or ELISA. As shown in FIG. 28, cytokines/chemokines were reduced when RSV replication was reduced when the antisense oligos for tRF5-GlyCCC and tRF5-LysCTT were used.

Effects of tRF5-GlyCCC and tRF5-LysCTT on Viral Replication. Viral titers were assessed for cells transfected with mimic oligos for tRF5-GlyCCC, tRF5-LysCTT or a scrambled control oligo. The result is a presentative of two separated experiments. As shown in FIG. 29, cytokines/chemokines were increased when RSV replication was increased through the use of oligos that were mimics of tRF5-GlyCCC and tRF5-LysCTT.

Dual-Luciferase assay of gene trans-silencing function of tRF5-LysCTT. Cells were co-transfected with firefly luciferase reporters containing the complementary sequence of tRF5-GlyGCC (tRF5-GlyGCC-luc) or tRF5-LysCTT (tRF5-LysCTT) and antisense oligos which are specifically against corresponding tRF5 or CN. After 15 h, cells were harvested for luciferase activity measurement. Renilla luciferase reporters were also transfected for the normalization. As shown in FIG. 30, tRF5-LysCTT has a gene trans-silencing function Conclusions tRF5-GlyCCC and tRF5-LysCTT are functional molecules induced by RSV infection that leads to increased viral replication. This is evidenced by the decreased in viral titers and subsequent inhibited viral protein expression when sequence specific antisense oligos are used (FIGS. 26 and 27). Since most cytokines and chemokines are viral replication dependent, it was not surprising to observe the reduction of cytokines/chemokines when RSV replication was decreased by tRF downregulation (FIG. 28). Vice versa, the mimics for tRF5-GlyCCC and tRF5-LysCTT respectively enhanced the RSV replication (FIG. 29), confirming these two tRFs are important in regulating RSV replication. Our dual-luciferase assay of tRFs and tRFs knockdown revealed that tRF5-LysCTT has gene regulatory functions in RSV replication (FIG. 30).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for decreasing Respiratory Syncytial Virus (RSV) replication in a cell, comprising:
- introducing a polynucleotide into a cell that comprises RSV, wherein the polynucleotide comprises a nucleotide sequence that is substantially identical to the complement of a reference sequence,
- wherein the reference sequence is at least 20 consecutive nucleotides selected from the first 31 nucleotides of a mature tRNA that specifies glutamic acid and has the anticodon CTC,
- wherein the first 31 nucleotides at the 5' end of the mature tRNA are 5'-TCCCTGGTGGTCTAGTGGTTAGGATTCGGCG (SEQ ID NO:6),
- and further wherein the reference sequence includes at least a portion of the 3' domain of SEQ ID NO:6, and
- wherein the number of non-complementary nucleotides between the polynucleotide and the reference sequence is no greater than 2.

2. The method of claim 1 wherein the polynucleotide comprises a nucleotide sequence that is identical to the complement of the reference sequence.

3. The method of claim 1 wherein the cell is an ex vivo cell.

4. The method of claim 3 wherein the ex vivo cell is a primary cell.

5. The method of claim 4 wherein the ex vivo cell is a cultured cell.

6. The method of claim 1 wherein the cell is an in vivo cell.

7. The method of claim 6 wherein the in vivo cell is present in an animal selected from a human, a chimpanzee, a cow, a sheep, a cotton rat, and a mouse.

8. The method of claim 6 wherein the in vivo cell is present in a human.

9. The method of claim 7 wherein the human is between 0 and 24 months of age.

10. The method of claim 1 wherein at least 2 polynucleotides are introduced into the cell.

11. The method of claim 1 wherein the polynucleotide comprises RNA.

12. The method of claim 1 wherein the introducing comprises introducing a vector into the cell, wherein the vector encodes the polynucleotide.

13. A method for treating a subject, comprising:
- administering to the respiratory tract of a subject in need thereof a composition comprising a polynucleotide that comprises a nucleotide sequence that is substantially identical to the complement of a reference sequence,
- wherein the reference sequence is at least 20 consecutive nucleotides selected from the first 31 nucleotides at the 5' end of a mature tRNA, wherein the mature tRNA is a tRNA that specifies glutamic acid and has the anticodon CTC,
- wherein the first 31 nucleotides at the 5' end of the mature tRNA are 5'-TCCCTGGTGGTCTAGTGGTTAGGATTCGGCG (SEQ ID NO:6),
- wherein the reference sequence includes at least a portion of the 3' domain of SEQ ID NO:6,
- wherein the subject has an RSV infection, and
- wherein the number of non-complementary nucleotides between the polynucleotide and the reference sequence is no greater than 2.

14. The method of claim 13 wherein the method further comprises administering an antiviral agent.

15. The method of claim 13 wherein the subject is an animal selected from a human, a chimpanzee, a cow, a sheep, a cotton rat, and a mouse.

16. The method of claim 13 wherein the subject is a human between 0 and 24 months of age.

17. The method of claim 15 wherein the human has symptoms of bronchiolitis, pneumonia, or the combination thereof.

18. The method of claim 1 wherein the nucleotide sequence of the polynucleotide that comprises a nucleotide sequence substantially identical to the complement of the first 31 nucleotides of SEQ ID NO:6 comprises GAAUCCTAACCACTAGACCA (SEQ ID NO:90).

19. The method of claim 13 wherein the polynucleotide comprises a nucleotide sequence that is identical to the complement of the reference sequence.

20. The method of claim 1 wherein the cell that comprises RSV is a cell present in the respiratory tract of a subject.

21. The method of claim 1 wherein the cell that comprises RSV is a respiratory cell selected from a superficial cell of a respiratory epithelium, a ciliated cell of a small bronchiole, and a type 1 pneumocyte of an alveolus.

22. The method of claim 1 wherein the cell that comprises RSV is selected from an A549 cell, a 293 cell, and a HEp-2 cell.

* * * * *

SEQUENCE LISTING

<160> NUMBER OF SEQ ID NOS: 126

<210> SEQ ID NO 1
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 1
gggggtatag ctcaggggta gagcatttg                                   29

<210> SEQ ID NO 2

-continued

```
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 2
ggttccatgg tgtaatggtt agcactctgg a                               31

<210> SEQ ID NO 3
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 3
ggttccatgg tgtaatggta agcactctg                                  29

<210> SEQ ID NO 4
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 4
ggttccatcg tgtaatggtg agcactctg                                  29

<210> SEQ ID NO 5
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 5
ggtcccgtgg tgtaatggtt agcactctgg                                 30

<210> SEQ ID NO 6
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 6
tccctggtgg tctagtggtt aggattcggc g                               31

<210> SEQ ID NO 7
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 7
tccctgtggt ctagtggtta ggattcggcg                                 30

<210> SEQ ID NO 8
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 8
```

```
tccctggtgg tctagtggct aggattcggc g                                          31

<210> SEQ ID NO 9
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 9
tcccacatgg tctagcggtt aggattcctg                                            30

<210> SEQ ID NO 10
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 10
tcccatatgg tctagcggtt aggattcctg g                                          31

<210> SEQ ID NO 11
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 11
gcatgggtgg ttcagtggta gaattctcg                                             29

<210> SEQ ID NO 12
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 12
gcgccgctgg tgtagtggta tcatgcaag                                             29

<210> SEQ ID NO 13
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 13
gcattggtgg ttcagtggta gaattctcg                                             29

<210> SEQ ID NO 14
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 14
gcattggtgg ttcagtggga gaattctcg                                             29

<210> SEQ ID NO 15
<211> LENGTH: 30
<212> TYPE: DNA
```

```
<213> ORGANISM: artificial
<220> FEATURE:
<223> OTHER INFORMATION: tRNA-derived RNA fragment (tRF)

<400> SEQUENCE: 15
gcgttggtgg tatagtggtg agcatagctg                                    30

<210> SEQ ID NO 16
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 16
gcgttggtgg tatagtggtg agaatagct                                     29

<210> SEQ ID NO 17
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 17
gccgtgatcg tatagtggtt agtactctgc g                                  31

<210> SEQ ID NO 18
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 18
gttaagatgg cagagcccgg taatcgcata a                                  31

<210> SEQ ID NO 19
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 19
gcccggctag ctcagtcggt agagcatgag                                    30

<210> SEQ ID NO 20
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 20
gcccggctag ctcagtcggt agagcatggg a                                  31

<210> SEQ ID NO 21
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 21
gcccggctag ctcagtcagt agagcatggg                                    30
```

<210> SEQ ID NO 22
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 22
gcccggatag ctcagtcggt agagcatcag                                       30

<210> SEQ ID NO 23
<211> LENGTH: 28
<212> TYPE: DNA
<213> ORGANISM: artificial
<220> FEATURE:
<223> OTHER INFORMATION: tRNA-derived RNA fragment (tRF)

<400> SEQUENCE: 23
agcagagtgg cgcagcggaa gcgtgctg                                         28

<210> SEQ ID NO 24
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 24
gccgaaatag ctcagttggg agagctttag a                                     31

<210> SEQ ID NO 25
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 25
gacgaggtgg ccgagtggtt aaggcaatgg                                       30

<210> SEQ ID NO 26
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 26
gtttccgtag tgtagtggtc atcacgttc                                        29

<210> SEQ ID NO 27
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 27
gtttccgtag tgtagtggtt atcacattc                                        29

<210> SEQ ID NO 28
<211> LENGTH: 29
<212> TYPE: DNA
<213> ORGANISM: artificial
<220> FEATURE:

-continued

<223> OTHER INFORMATION: tRNA-derived RNA fragment (tRF)

<400> SEQUENCE: 28
gggggattag ctcaaatggt agagccctc                                29

<210> SEQ ID NO 29
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 29
gggggattag ctcaaatggt agagctctc                                29

<210> SEQ ID NO 30
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 30
gggggtgtag ctcagtggta gagcgcatg                                29

<210> SEQ ID NO 31
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 31
gggccagtgg cgcaatggat aacgcctct                                29

<210> SEQ ID NO 32
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 32
gacccagtgg cctaatggat aaggcatcag                               30

<210> SEQ ID NO 33
<211> LENGTH: 32
<212> TYPE: DNA
<213> ORGANISM: artificial
<220> FEATURE:
<223> OTHER INFORMATION: tRNA-derived RNA fragment (tRF)

<400> SEQUENCE: 33
gccccagtgg cctaatggat aaggcactgc ct                            32

<210> SEQ ID NO 34
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 34
gaccgcgtgg cctaatggat aaggcttctg                               30

-continued

```
<210> SEQ ID NO 35
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 35
ggctccgtgg cgcaatggat agcgcattg                                    29

<210> SEQ ID NO 36
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 36
ggctctgtgg cgcaatggat agcgcattg                                    29

<210> SEQ ID NO 37
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 37
ggctctctgg cgcaatggat agcgcattg                                    29

<210> SEQ ID NO 38
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 38
ggatctgtgg cgcaatggat agcgcattg                                    29

<210> SEQ ID NO 39
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 39
ggctctgtag cgcaatggat agcgcattgg                                   30

<210> SEQ ID NO 40
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 40
gtctctgtgg cgcaatcggt tagcgctttc g                                 31

<210> SEQ ID NO 41
<211> LENGTH: 30
<212> TYPE: DNA
<213> ORGANISM: artificial
<220> FEATURE:
<223> OTHER INFORMATION: tRNA-derived RNA fragment (tRF)
```

```
<400> SEQUENCE: 41
tcctcgttcg tatagtggtg agtatccccg                                    30

<210> SEQ ID NO 42
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 42
tcctcttttg tatagtggtg agtatccccg c                                  31

<210> SEQ ID NO 43
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 43
ggttccatcg tgtaatggtt agcactctgg a                                  31

<210> SEQ ID NO 44
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 44
ggttccatgg tgtaacggtt agcactctgg a                                  31

<210> SEQ ID NO 45
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 45
ggttccattg tgtaatggta agcactctgg a                                  31

<210> SEQ ID NO 46
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 46
ggttccatgt gtaatggtta gcactctgg                                     29

<210> SEQ ID NO 47
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 47
tccctgtggt ctagtggcta ggattcggcg                                    30

<210> SEQ ID NO 48
<211> LENGTH: 31
```

```
<212> TYPE: DNA
<213> ORGANISM: artificial
<220> FEATURE:
<223> OTHER INFORMATION: tRNA-derived RNA fragment (tRF)

<400> SEQUENCE: 48
gccgtaatcg tatagtggtt agtactctgc g                             31

<210> SEQ ID NO 49
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 49
gctccagtgg cgcaatcggt tagcgcgcgg                               30

<210> SEQ ID NO 50
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 50
ggccggttag ctcagttgga agagcgtggt g                             31

<210> SEQ ID NO 51
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 51
ggtagcgtgg ccgagcggtc taaggcctgg                               30

<210> SEQ ID NO 52
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 52
ggtagcgtgg ccgagcggtc taaggctctg g                             31

<210> SEQ ID NO 53
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 53
ggtagcgtgg ccgagcggtc taaggcgctg g                             31

<210> SEQ ID NO 54
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 54
```

```
gtcaggatgg ccgagtggtc taaggcccag a                              31

<210> SEQ ID NO 55
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 55
gtcaggatgg ccgagtggtc taaggcgcca g                              31

<210> SEQ ID NO 56
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 56
gtcaggatgg ccgagcggtc taaggcgctg c                              31

<210> SEQ ID NO 57
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 57
ggtagtgtgg ccgagcggtc taaggcctgg                                30

<210> SEQ ID NO 58
<211> LENGTH: 28
<212> TYPE: DNA
<213> ORGANISM: artificial
<220> FEATURE:
<223> OTHER INFORMATION: tRNA-derived RNA fragment (tRF)

<400> SEQUENCE: 58
agcagagggg cgcagcggaa gcgtgctg                                  28

<210> SEQ ID NO 59
<211> LENGTH: 28
<212> TYPE: DNA
<213> ORGANISM: artificial
<220> FEATURE:
<223> OTHER INFORMATION: tRNA-derived RNA fragment (tRF)

<400> SEQUENCE: 59
agcagagtgg cgcagtggaa gcgtgctg                                  28

<210> SEQ ID NO 60
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 60
ggctcgttgg tctaggggta tgattctcg                                 29

<210> SEQ ID NO 61
<211> LENGTH: 33
<212> TYPE: DNA
<213> ORGANISM: artificial
```

<220> FEATURE:
<223> OTHER INFORMATION: tRNA-derived RNA fragment (tRF)

<400> SEQUENCE: 61
ggctcgttag tctagggta tgattctcgc ttc         33

<210> SEQ ID NO 62
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 62
ggctcgttgg tctagtggta tgattctcg         29

<210> SEQ ID NO 63
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 63
gtagtcgtgg ccgagtggtt aaggctatgg         30

<210> SEQ ID NO 64
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 64
gctgtgatgg ccgagtggtt aaggctttgg a         31

<210> SEQ ID NO 65
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 65
gacgaggtgg ccgagtggtt aaggctatgg         30

<210> SEQ ID NO 66
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 66
gacgaggtgg ccgagtggtt aaggcgatgg         30

<210> SEQ ID NO 67
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 67
gcagcgatgg ccgagtggtt aaggctttg         29

```
<210> SEQ ID NO 68
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 68
ggcgccgtgg cttagttggt taaaactcct g                              31

<210> SEQ ID NO 69
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 69
ggcgcggtgg ccaagtggta aggcttcgg                                 29

<210> SEQ ID NO 70
<211> LENGTH: 25
<212> TYPE: DNA
<213> ORGANISM: artificial
<220> FEATURE:
<223> OTHER INFORMATION: tRNA-derived RNA fragment (tRF)

<400> SEQUENCE: 70
ccttcaatag atcagctggt agagc                                     25

<210> SEQ ID NO 71
<211> LENGTH: 26
<212> TYPE: DNA
<213> ORGANISM: artificial
<220> FEATURE:
<223> OTHER INFORMATION: tRNA-derived RNA fragment (tRF)

<400> SEQUENCE: 71
gggggtgtag ctcagtggta gagcgt                                    26

<210> SEQ ID NO 72
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 72
gtttccgtgg tgtagtggtt atcacattc                                 29

<210> SEQ ID NO 73
<211> LENGTH: 21
<212> TYPE: DNA
<213> ORGANISM: artificial
<220> FEATURE:
<223> OTHER INFORMATION: antisense fragment of tRNA-derived RNA fragment
      (tRF) specifying gluatmic acid

<400> SEQUENCE: 73
taaccactag accaccaggg a                                         21

<210> SEQ ID NO 74
<211> LENGTH: 23
<212> TYPE: DNA
<213> ORGANISM: artificial
<220> FEATURE:
```

```
<223> OTHER INFORMATION: antisense fragment of tRNA-derived RNA fragment
      (tRF) specifying gluatmic acid

<400> SEQUENCE: 74
gccgaatcct aaccactaga cca                                              23

<210> SEQ ID NO 75
<211> LENGTH: 27
<212> TYPE: DNA
<213> ORGANISM: artificial
<220> FEATURE:
<223> OTHER INFORMATION: antisense fragment of tRNA-derived RNA fragment
      (tRF) specifying gluatmic acid

<400> SEQUENCE: 75
cgccgaatcc taaccactag accacca                                          27

<210> SEQ ID NO 76
<211> LENGTH: 35
<212> TYPE: DNA
<213> ORGANISM: artificial
<220> FEATURE:
<223> OTHER INFORMATION: oligonucleotide primer

<400> SEQUENCE: 76
aattcgccga atcctaacca ctagaccacc aggga                                 35

<210> SEQ ID NO 77
<211> LENGTH: 35
<212> TYPE: DNA
<213> ORGANISM: artificial
<220> FEATURE:
<223> OTHER INFORMATION: oligonucleotide primer

<400> SEQUENCE: 77
tcgatccctg gtggtctagt ggttaggatt cggcg                                 35

<210> SEQ ID NO 78
<211> LENGTH: 20
<212> TYPE: DNA
<213> ORGANISM: artificial
<220> FEATURE:
<223> OTHER INFORMATION: antisense non-targeting control oligonucleotide

<400> SEQUENCE: 78
ccgcugagct aaagccagcc                                                  20

<210> SEQ ID NO 79
<211> LENGTH: 41
<212> TYPE: DNA
<213> ORGANISM: artificial
<220> FEATURE:
<223> OTHER INFORMATION: oligonucleotide primer

<400> SEQUENCE: 79
ctgcgatgag tggcaggctt ttttttttt aactaaagct c                           41

<210> SEQ ID NO 80
<211> LENGTH: 30
<212> TYPE: DNA
<213> ORGANISM: artificial
<220> FEATURE:
<223> OTHER INFORMATION: oligonucleotide primer

<400> SEQUENCE: 80
actacagtgt attagacttr acagcagaag                                       30
```

<210> SEQ ID NO 81
<211> LENGTH: 18
<212> TYPE: DNA
<213> ORGANISM: artificial
<220> FEATURE:
<223> OTHER INFORMATION: oligonucleotide primer

<400> SEQUENCE: 81
ctgcgatgag tggcaggc                                                    18

<210> SEQ ID NO 82
<211> LENGTH: 38
<212> TYPE: DNA
<213> ORGANISM: artificial
<220> FEATURE:
<223> OTHER INFORMATION: oligonucleotide primer

<400> SEQUENCE: 82
aattgttctg ccacttactc ccactagaca accaggga                              38

<210> SEQ ID NO 83
<211> LENGTH: 38
<212> TYPE: DNA
<213> ORGANISM: artificial
<220> FEATURE:
<223> OTHER INFORMATION: oligonucleotide primer

<400> SEQUENCE: 83
tcgatccctg gttgtctagt gggagtaagt ggcagaac                              38

<210> SEQ ID NO 84
<211> LENGTH: 75
<212> TYPE: DNA
<213> ORGANISM: artificial
<220> FEATURE:
<223> OTHER INFORMATION: tRNA-derived RNA fragment (tRF)

<400> SEQUENCE: 84
tccctggtgg tctagtggtt aggattcggc gctctcaccg ccgcggcccg ggttcgattc      60
ccggtcaggg aacca                                                      75

<210> SEQ ID NO 85
<211> LENGTH: 27
<212> TYPE: DNA
<213> ORGANISM: artificial
<220> FEATURE:
<223> OTHER INFORMATION: oligonucleotide probe

<400> SEQUENCE: 85
cgccgaatcc taaccactag accacca                                         27

<210> SEQ ID NO 86
<211> LENGTH: 74
<212> TYPE: DNA
<213> ORGANISM: artificial
<220> FEATURE:
<223> OTHER INFORMATION: tRNA-derived RNA fragment (tRF)

<400> SEQUENCE: 86
gcatgggtgg ttcagtggta gaattctcgc ctgccacgcg ggaggcccgg gttcgattcc      60
cggcccatgc acca                                                       74

<210> SEQ ID NO 87

```
<211> LENGTH: 21
<212> TYPE: DNA
<213> ORGANISM: artificial
<220> FEATURE:
<223> OTHER INFORMATION: oligonucleotide probe

<400> SEQUENCE: 87
gagaattcta ccactgaacc a                                              21

<210> SEQ ID NO 88
<211> LENGTH: 76
<212> TYPE: DNA
<213> ORGANISM: artificial
<220> FEATURE:
<223> OTHER INFORMATION: tRNA-derived RNA fragment (tRF)

<400> SEQUENCE: 88
gcccggctag ctcagtcggt agagcatgag actcttaatc tcagggtcgt gggttcgagc    60
cccacgttgg gcgcca                                                    76

<210> SEQ ID NO 89
<211> LENGTH: 20
<212> TYPE: DNA
<213> ORGANISM: artificial
<220> FEATURE:
<223> OTHER INFORMATION: oligonucleotide probe

<400> SEQUENCE: 89
accgactgag ctagccgggc                                                20

<210> SEQ ID NO 90
<211> LENGTH: 20
<212> TYPE: DNA
<213> ORGANISM: artificial
<220> FEATURE:
<223> OTHER INFORMATION: tRNA-derived RNA fragment (tRF)

<400> SEQUENCE: 90
gaaucctaac cactagacca                                                20

<210> SEQ ID NO 91
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 91
cgccgaatcc taaccactag accaccaggg a                                   31

<210> SEQ ID NO 92
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 92
cgcggtatgc taaccactag accaccaggg a                                   31

<210> SEQ ID NO 93
<211> LENGTH: 31
<212> TYPE: DNA
<213> ORGANISM: artificial
<220> FEATURE:
<223> OTHER INFORMATION: tRNA-derived RNA fragment (tRF)
```

```
<400> SEQUENCE: 93
cgccgaatcc aaaccgcaac accaccaggg a                              31

<210> SEQ ID NO 94
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 94
cgccgaatcc taaccactag accacaatgc a                              31

<210> SEQ ID NO 95
<211> LENGTH: 21
<212> TYPE: DNA
<213> ORGANISM: artificial
<220> FEATURE:
<223> OTHER INFORMATION: tRNA-derived RNA fragment (tRF)

<400> SEQUENCE: 95
ucuagugguu aggauucggc g                                         21

<210> SEQ ID NO 96
<211> LENGTH: 72
<212> TYPE: DNA
<213> ORGANISM: artificial
<220> FEATURE:
<223> OTHER INFORMATION: tRNA-derived RNA fragment (tRF)

<400> SEQUENCE: 96
tccctggtgg tctagtggtt aggattcggc gctctcaccg ccgcggcccg ggttcgattc    60
ccggtcaggg aa                                                       72

<210> SEQ ID NO 97
<211> LENGTH: 26
<212> TYPE: DNA
<213> ORGANISM: artificial
<220> FEATURE:
<223> OTHER INFORMATION: tRNA-derived RNA fragment (tRF)

<400> SEQUENCE: 97
tccctggtgg tctagtggtt aggatt                                    26

<210> SEQ ID NO 98
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 98
tccctggtgg tctagtggtt aggattcgg                                 29

<210> SEQ ID NO 99
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 99
tccctggtgg tctagtggtt aggattcggc                                30
```

```
<210> SEQ ID NO 100
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 100
tccctggtgg tctagtggtt aggattcggc g                                31

<210> SEQ ID NO 101
<211> LENGTH: 32
<212> TYPE: DNA
<213> ORGANISM: artificial
<220> FEATURE:
<223> OTHER INFORMATION: tRNA-derived RNA fragment (tRF)

<400> SEQUENCE: 101
tccctggtgg tctagtggct aggattcggc gc                               32

<210> SEQ ID NO 102
<211> LENGTH: 33
<212> TYPE: DNA
<213> ORGANISM: artificial
<220> FEATURE:
<223> OTHER INFORMATION: tRNA-derived RNA fragment (tRF)

<400> SEQUENCE: 102
tccctggtgg tctagtggtt aggattcggc gct                              33

<210> SEQ ID NO 103
<211> LENGTH: 45
<212> TYPE: DNA
<213> ORGANISM: artificial
<220> FEATURE:
<223> OTHER INFORMATION: tRNA-derived RNA fragment (tRF)

<400> SEQUENCE: 103
cctgccacgc gggaggcccg ggttcgattc ccggcccatg cacca                 45

<210> SEQ ID NO 104
<211> LENGTH: 19
<212> TYPE: DNA
<213> ORGANISM: artificial
<220> FEATURE:
<223> OTHER INFORMATION: tRNA-derived RNA fragment (tRF)

<400> SEQUENCE: 104
tgcatgggcc gggaatcga                                              19

<210> SEQ ID NO 105
<211> LENGTH: 74
<212> TYPE: DNA
<213> ORGANISM: artificial
<220> FEATURE:
<223> OTHER INFORMATION: tRNA-derived RNA fragment (tRF)

<400> SEQUENCE: 105
gcatgggtgg ttcagtggta gaattctcgc ctgccacgcg ggaggcccgg gttcgattcc    60
cggcccatgc agca                                                   74

<210> SEQ ID NO 106
<211> LENGTH: 25
<212> TYPE: DNA
<213> ORGANISM: artificial
```

```
<220> FEATURE:
<223> OTHER INFORMATION: tRNA-derived RNA fragment (tRF)

<400> SEQUENCE: 106
gcatgggtgg ttcagtggta gaatt                                           25

<210> SEQ ID NO 107
<211> LENGTH: 27
<212> TYPE: DNA
<213> ORGANISM: artificial
<220> FEATURE:
<223> OTHER INFORMATION: tRNA-derived RNA fragment (tRF)

<400> SEQUENCE: 107
gcatgggtgg ttcagtggta gaattct                                         27

<210> SEQ ID NO 108
<211> LENGTH: 28
<212> TYPE: DNA
<213> ORGANISM: artificial
<220> FEATURE:
<223> OTHER INFORMATION: tRNA-derived RNA fragment (tRF)

<400> SEQUENCE: 108
gcatgggtgg ttcagtggta gaattctc                                        28

<210> SEQ ID NO 109
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 109
gcatgggtgg ttcagtggta gaattctcgc                                      30

<210> SEQ ID NO 110
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 110
gcatgggtgg ttcagtggta gaattctcgc g                                    31

<210> SEQ ID NO 111
<211> LENGTH: 72
<212> TYPE: DNA
<213> ORGANISM: artificial
<220> FEATURE:
<223> OTHER INFORMATION: tRNA-derived RNA fragment (tRF)

<400> SEQUENCE: 111
gcccggctag ctcagtcggt agagcatgag actcttaatc tcagggtcgt ggttcgagcc     60
ccacgttggg cg                                                         72

<210> SEQ ID NO 112
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 112
```

```
gcccggctag ctcagtcggt agagcatga                                           29

<210> SEQ ID NO 113
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 113
gcccggctag ctcagtcggt agagcatgag                                          30

<210> SEQ ID NO 114
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 114
gcccggctag ctcagtcggt agagcatgag a                                        31

<210> SEQ ID NO 115
<211> LENGTH: 72
<212> TYPE: DNA
<213> ORGANISM: artificial
<220> FEATURE:
<223> OTHER INFORMATION: tRNA-derived RNA fragment (tRF)

<400> SEQUENCE: 115
ggttccatgg tgtaatggtt agcactctgg actctgaatc cagcgatccg agttcaaatc         60
tcggtggaac ct                                                             72

<210> SEQ ID NO 116
<211> LENGTH: 0
<212> TYPE: DNA
<213> ORGANISM: artificial
<220> FEATURE:
<223> OTHER INFORMATION: tRNA-derived RNA fragment (tRF)

<400> SEQUENCE: 116

000

<210> SEQ ID NO 117
<211> LENGTH: 29
<212> TYPE: DNA
<213> ORGANISM: artificial
<220> FEATURE:
<223> OTHER INFORMATION: tRNA-derived RNA fragment (tRF)

<400> SEQUENCE: 117
ggttccatgg tgtaatggtt agcactctg                                           29

<210> SEQ ID NO 118
<211> LENGTH: 30
<212> TYPE: DNA
<213> ORGANISM: artificial
<220> FEATURE:
<223> OTHER INFORMATION: tRNA-derived RNA fragment (tRF)

<400> SEQUENCE: 118
ggttccatgg tgtaatggtt agcactctgg                                          30

<210> SEQ ID NO 119
<211> LENGTH: 31
```

```
<212> TYPE: DNA
<213> ORGANISM: artificial
<220> FEATURE:
<223> OTHER INFORMATION: tRNA-derived RNA fragment (tRF)

<400> SEQUENCE: 119
ggttccatgg tgtaatggtt agcactctgg a                              31

<210> SEQ ID NO 120
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 120
cugccacuua cucccacuag acaaccaggg a                              31

<210> SEQ ID NO 121
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 121
ucccuggugg ucuagugguu aggauucggc g                              31

<210> SEQ ID NO 122
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 122
cugccacuua cucccacuag acaaccaggg a                              31

<210> SEQ ID NO 123
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 123
guggcucaua cucccacuag acaaccaggg a                              31

<210> SEQ ID NO 124
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 124
cugccacuua cucggacaug ugaaccaggg a                              31

<210> SEQ ID NO 125
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 125
```

-continued

```
cugccacuua cucccacuag acaaggaccc a                                 31

<210> SEQ ID NO 126
<211> LENGTH: 31
<212> TYPE: DNA
<213> ORGANISM: artificial
<220> FEATURE:
<223> OTHER INFORMATION: tRNA-derived RNA fragment (tRF)

<400> SEQUENCE: 126
ucccuggugg ucuagugguu agguuaccgc c                                 31
```